US011399727B2

(12) United States Patent
Yaniv et al.

(10) Patent No.: US 11,399,727 B2
(45) Date of Patent: Aug. 2, 2022

(54) NON-INVASIVE ANALYSIS OF SINOATRIAL NODE AND AUTONOMIC NERVOUS INPUT TO HEART FUNCTION

(71) Applicant: TECHNION RESEARCH & DEVELOPMENT FOUNDATION LIMITED, Haifa (IL)

(72) Inventors: Yael Yaniv, Haifa (IL); Aviv Rosenberg, Kiryat Tivon (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 141 days.

(21) Appl. No.: 16/763,437

(22) PCT Filed: Nov. 14, 2018

(86) PCT No.: PCT/IL2018/051226
§ 371 (c)(1),
(2) Date: May 12, 2020

(87) PCT Pub. No.: WO2019/097509
PCT Pub. Date: May 23, 2019

(65) Prior Publication Data
US 2020/0305734 A1    Oct. 1, 2020

Related U.S. Application Data

(60) Provisional application No. 62/586,406, filed on Nov. 15, 2017.

(51) Int. Cl.
*A61B 5/024*    (2006.01)
*G16H 50/20*    (2018.01)
(Continued)

(52) U.S. Cl.
CPC .......... *A61B 5/02405* (2013.01); *A61B 5/316* (2021.01); *A61B 5/364* (2021.01);
(Continued)

(58) Field of Classification Search
CPC .. G16H 50/20; A61K 31/519; A61B 5/02405; A61B 5/364; A61B 5/316; A61B 5/4836; A61B 5/7278
See application file for complete search history.

(56) References Cited

U.S. PATENT DOCUMENTS

2004/0230252 A1* 11/2004 Kullok ................. A61M 21/00
607/48
2014/0364756 A1* 12/2014 Brockway ............ G06K 9/0053
600/513

(Continued)

FOREIGN PATENT DOCUMENTS

JP      2006150065 A    6/2006

OTHER PUBLICATIONS

George E. Billman, "Heart rate variability—a historical perspective", Frontiers in Physiology, pp. 1-13, Nov. 29, 2011.
(Continued)

*Primary Examiner* — Catherine M Voorhees
*Assistant Examiner* — Roland Dinga
(74) *Attorney, Agent, or Firm* — The Roy Gross Law Firm, LLC; Roy Gross

(57) ABSTRACT

A method for evaluating heart function, comprising receiving a digitized cardiac signal, computing a power spectral density (PSD) or multiscale entropy (MSE) of the digitized cardiac signal, and evaluating heart function based on the PSD or MSE is provided. Systems and computer program products for doing same are also provided.

19 Claims, 30 Drawing Sheets
(9 of 30 Drawing Sheet(s) Filed in Color)

(51) Int. Cl.
 A61B 5/00 (2006.01)
 A61K 31/519 (2006.01)
 A61B 5/316 (2021.01)
 A61B 5/364 (2021.01)
(52) U.S. Cl.
 CPC .......... *A61B 5/4836* (2013.01); *A61B 5/7278* (2013.01); *A61K 31/519* (2013.01); *G16H 50/20* (2018.01)

(56) References Cited

U.S. PATENT DOCUMENTS

2015/0272456 A1  10/2015  Kyal et al.
2016/0000349 A1  1/2016  Sullivan et al.
2017/0265818 A1  9/2017  Kanada

OTHER PUBLICATIONS

Fred Shaffer et al., "A healthy heart is not a metronome: an integrative review of the heart's anatomy and heart rate variability", Frontiers in Psychology, vol. 5 p. 1040, Sep. 2014.
Claude E. Shannon, "A mathematical theory of communication", The Bell System Technical Journal, pp. 379-423, 1948.
J. L. A. Carvalho et al., "Study on the Optimal Order for the Auto-Regressive Time-Frequency Analysis of Heart Rate Variability", Spectrum, pp. 2621-2625, Oct. 2003.
Lennart Bergfeldt and Yoshiyuki Haga, "Power spectral and Poincaré plot characteristics in sinus node dysfunction", Journal of Applied Physiology, vol. 94 Issue 6 pp. 2217-2224, 2003.
Chung-Kang Peng et al. "Quantification of scaling exponents and crossover phenomena in nonstationary heartbeat time series", Chaos, vol. 5 Issue 1 pp. 82-87, 1995.
Plamen Ch. Ivanov et al., "Scaling and universality in heart rate variability distributions", Physica A, vol. 249 pp. 587-593, 1998.
Benoit B. Mandelbrot, "How Long Is the Coast of Britain? Statistical Self-Similarity and Fractional Dimension", Science, vol. 156 Issue 3775 pp. 636-638, 1967.
Yi-Cheng Zhang, "Complexity and 1/f noise. A phase space approach", Journal de Physique I, EDP Sciences, vol. 1 Issue 7 pp. 971-977, 1991.
Thomas M. Cover and Joy A. Thomas, "Elements of Information", Theory, Wiley, Second edition, pp. 1-748, 2005.
Steven M. Pincus, "Assessing serial irregularity and its implications for health", Annals of the New York Academy of Sciences, vol. 954 Issue 1 pp. 245-267, 2001.
Joshua S. Richman and J. Randall Moorman, "Physiological time-series analysis using approximate entropy and sample entropy", American Journal of Physiology Heart and Circulatory Physiology, vol. 278 Issue 6 pp. H2039-H2049, 2000.
Madalena D. Costa et al., "Multiscale entropy analysis of complex physiologic time series", Physical Review Letters, vol. 89 Issue 6 p. 068102, 2002.
George E. Billman et al., "An introduction to heart rate variability: methodological considerations and clinical applications", Front Physiol, vol. 6 Issue 55, 2015.
Stefanie Hillebrand et al., "Heart rate variability and first cardiovascular event in populations without known cardiovascular disease: meta-analysis and dose-response meta-regression", Europace, vol. 5 pp. 742-749, 2013.
Yael Yaniv et al., "Impaired Signaling Intrinsic to Sinoatrial Node Pacemaker Cells Affects Heart Rate Variability during Cardiac Disease", J. Clin. Trials, vol. 4 Issue 1 p. 152, 2013.
Ju-Yi Chen et al., "Cardiac autonomic functions derived from short-term heart rate variability recordings associated with heart rate recovery after treadmill exercise test in young individuals", Hear Vessels, vol. 26 Issue 3 pp. 282-288, 2011.
Richard P. Sloan et al., "Cardiac autonomic control and the effects of age, race, and sex: the CARDIA study", Auton Neurosci, vol. 139 Issue 1-2 pp. 78-85, 2008.

A. D. Jose and D. Collison, "The normal range and determinants of the intrinsic heart rate in man" Cardiovasc Res, vol. 4 Issue 2 pp. 160-167, 1970.
J. T. Bigger Jr. et al., "Power law behavior of RR-interval variability in healthy middle-aged persons, patients with recent acute myocardial infarction, and patients with heart transplants", Circulation, vol. 15 Issue pp. 2142-2151, 1996.
Yael Yaniv et al., "Stochasticity intrinsic to coupled-clock mechanisms underlies beat-to-beat variability of spontaneous action potential firing in sinoatrial node pacemaker cells", J Mol Cell Cardiol, vol. 77 pp. 1-10, 2014.
Meital Ben-Ari et al., "From beat rate variability in induced pluripotent stem cell-derived pacemaker cells to heart rate variability in human subjects", Hear Rhythm, vol. 11 Issue 10 pp. 1808-1818, 2014.
International Search Report of PCT/IL2018/051226 Completed Mar. 11, 2019; dated Mar. 12, 2019 3 pages.
Written Opinion of PCT/IL2018/051226 Completed Mar. 11, 2019; dated Mar. 12, 2019 6 pages.
Madalena Costa et al., "Multiscale entropy of biological signals", Physical Review, vol. 71 Issue (2 Pt 1) p. 021906, 2005.
Yael Yaniv et al., "Impaired Signaling Intrinsic to Sinoatrial Node Pacemaker Cells Affects Heart Rate Variability during Cardiac Disease", J Clin Trials, Issue 4 vol. 1 p. 152, 2014.
Fredric Shaffer and J. P. Ginsberg, "An Overview of Heart Rate Variability Metrics and Norms", Frontiers in Public Health, vol. 5 Article 258, 2017.
Joachim A. Behar et al., "A Universal Scaling Relation for Defining Power Spectral Bands in Mammalian Heart Rate Variability Analysis", Front. Physiol., vol. 9 Issue 1001, 2018.
Ofer Binah et al., "Integrating beat rate variability: From single cells to hearts", Heart rhythm: the official journal of the Heart Rhythm Society, vol. 10 Issue 6, 2013.
Yael Yaniv et al., "Synchronization of sinoatrial node pacemaker cell clocks and its autonomic modulation impart complexity to heart beating intervals", Heart rhythm: the official journal of the Heart Rhythm Society, vol. 11 Issue 7, 2014.
Yael Yaniv et al., "Deterioration of autonomic neuronal receptor signaling and mechanisms intrinsic to heart pacemaker cells contribute to age-associated alterations in heart rate variability in vivo", Aging Cell, vol. 15 Issue 4, 2016.
George Billman, "The effect of heart rate on the heart rate variability response to autonomic interventions", Frontiers in Physiology, vol. 4 Article 222, 2013.
Chung-Kang Peng et al., "Mosaic organization of DNA nucleotides", Physical review, E, Statistical physics, plasmas, fluids, and related interdisciplinary topics, vol. 49 Issue 2 pp. 1685-1689, 1994.
Matteo E Mangoni and Joël Nargeot. "Genesis and regulation of the heart automaticity", Physiological Reviews, vol. 88 Issue pp. 919-982, 2008.
Dario DiFrancesco, "The cardiac hyperpolarizing-activated current, if. Origins and developments", Progress in Biophysics and Molecular Biology, vol. 46 Issue 3 pp. 163-183, 1985.
Dario DiFrancesco, "Pacemaker mechanisms in cardiac tissue", Annual Review of Physiology, vol. 55 pp. 455-472, 1993.
Tatiana M. Vinogradova et al., "Rhythmic Ryanodine Receptor Ca2+ Releases during Diastolic Depolarization of Sinoatrial Pacemaker Cells Do Not Require Membrane Depolarization", Circulation Research, vol. 94 Issue 6 pp. 802-809, 2004.
Edward G. Lakatta et al., "Cardiac Impulse Is Initiated by a Coupled System of Membrane Ion Channels and Ca2+ Cycling Proteins", Sixth Edition, Cardiac Electrophysiology Elsevier Inc., pp. 243-252, 2014.
Donald M. Bers, "Cardiac excitation-contraction coupling", Nature, vol. 415 Issue 6868 pp. 198-205, 2014.
Matthew N. Levy, "Sympathetic-Parasympathetic Interactions in the Heart", Circulation Research, vol. 29 Issue 5 pp. 437-445, 1971.
Yael Yaniv et al., "The Fractal-like Complexity of Heart Rate Variability beyond Neurotransmitters and Autonomic Receptors: Signaling Intrinsic to Sinoatrial Node Pacemaker Cells", Cardiovascular Pharmacology, vol. 2 Issue 111, 2013.

(56) References Cited

OTHER PUBLICATIONS

Marek Malik et al., "Heart rate variability. Standards of measurement, physiological interpretation, and clinical use", European Heart Journal, vol. 17 Issue 3 pp. 354-381, 1996.
Stefano Guzzetti et al., "Non-linear dynamics and chaotic indices in heart rate variability of normal subjects and heart-transplanted patients", Cardiovascular Research, vol. 31 Issue 3 pp. 441-446, 1996.
Ary L. Goldberger et al. "Fractal dynamics in physiology: Alterations with disease and aging", Proceedings of the National Academy of Sciences, vol. 99 Supplement 1 pp. 2466-2472, 2002.
Madalena D. Costa et al., "Multiscale analysis of heart rate dynamics: Entropy and time irreversibility measures", Cardiovascular Engineering, vol. 8 Issue 2 pp. 88-93, 2008.
Ary L. Goldberger et al., "PhysioBank, PhysioToolkit, and PhysioNet: components of a new research resource for complex physiologic signals", Circulation, vol. 101 Issue 23 pages E215-E220, 2000.
Ary L. Goldberger et al., "On a mechanism of cardiac electrical stability. The fractal hypothesis", Biophysical Journal, vol. 48 Issue 3 pp. 525-528, 1985.
Ary L. Goldberger et al., "Chaos and fractals in human physiology", Scientific American, vol. 262 Issue 2 pp. 42-49, 1990.
Chung-Kang Peng et al., "Fractal mechanisms in neuronal control: human heartbeat and gait dynamics in health and disease", in Book published by Cambridge University Press, pp. 66-96, 2000.
Yael Mandel et al., "Human embryonic and induced pluripotent stem cell-derived cardiomyocytes exhibit beat rate variability and power-law behavior", Circulation, vol. 125 Issue 7 pp. 883-893, 2012.
Ofer Binah et al., "Integrating beat rate variability: from single cells to hearts", Heart Rhythm, vol. 10 Issue 6 pp. 928-932, 2013.
Anthony D. Jose, "Effect of combined sympathetic and parasympathetic blockade on heart rate and cardiac function in man". The American Journal of Cardiology, vol. 18 Issue 3, pp. 476-478, 1966.
Anthony D. Jose et al., "The effects of exercise and changes in body temperature on the intrinsic heart rate in man", American Heart Journal, vol. 79 Issue 4 pp. 488-498, 1970.
G. R. Cumming and G. H. Mir, "Heart rate and haemodynamics after autonomic blockade in infants and children" British Heart Journal, vol. 32 Issue 6 pp. 766-770, 1970.
Yael Yaniv et al., "Deterioration of autonomic neuronal receptor signaling and mechanisms intrinsic to heart pacemaker cells contribute to age-associated alterations in heart rate variability in vivo", Aging Cell, vol. 15 Issue 4 pp. 716-724, 2016.
George E. Billman et al., "Exercise training-induced bradycardia: evidence for enhanced parasympathetic regulation without changes in intrinsic sinoatrial node function", Journal of Applied Physiology, vol. 118 Issue 11 pp. 1344-1355, 1985.
Mariano Llamedo and Juan Pablo Martinez, "QRS Detectors Performance Comparison in Public Databases", Computing in Cardiology, pp. 357-360, 2014.
Alistair E. W. Johnson et al., "Multimodal heart beat detection using signal quality indices", Physiological Measurement, vol. 36 Issue 8 pp. 1665-1677, 2015.
George Moody et al., "Robust Detection of Heart Beats in Multimodal Data: The PhysioNet/Computing in Cardiology Challenge 2014", Cambridge, MA, Computing in Cardiology, pp. 549-552, 2014.
Joachim Behar et al., "A comparison of single channel fetal ECG extraction methods", Annals of Biomedical Engineering, vol. 42 Issue 6 pp. 1340-1353, 2014.
Gari D. Clifford, "Signal Processing Methods for Heart Rate Variability", Thesis in Department of Engineering Science, University of Oxford, pp. 1-218, 2002.
George B. Moody. "Spectral analysis of heart rate without resampling", IEEE, Proceedings of Computers in Cardiology Conference London, pp. 7-10, 1993.
Michael Brennan et al., "Do existing measures of Poincaré plot geometry reflect nonlinear features of heart rate variability?", IEEE Transactions on Biomedical Engineering, vol. 48 Issue 11 pp. 1342-1347, 2001.
Jaroslaw Piskorski and Przemyslaw Guzik, "Filtering Poincaré plots", Computational Methods in Science and Technology, vol. 11 Issue 1 pp. 39-48, 2005.
Joseph E. Mietus and Ary L. Goldberger, "Heart Rate Variability Analysis with the HRV Toolkit", Basic Time and Frequency Domain Measures, 2011, retrieved from: "https://archive.physionet.org/tutorials/hrv-toolkit/index2.shtml".
Nikhil Iyengar et al., "Age-related alterations in the fractal scaling of cardiac interbeat interval dynamics", The American Journal of Physiology, Am J Physiol, vol. 271 Issue 4 Pt 2, pp. R1078-1084, 1996.
Jaroslaw Piskorski and Przemyslaw Guzik, "Geometry of the Poincaré plot of RR intervals and its asymmetry in healthy adults", Physiological Measurement, vol. 28 Issue 3 pp. 287-300, 2007.
Michael Brennan et al., "Poincaré plot interpretation using a physiological model of HRV based on a network of oscillators", American journal of physiology Heart and Circulatory Physiology, vol. 283 Issue 5 pp. H1873-H1886, 2002.
Roy D. Yates et al., "Probability and Stochastic Processes", John Wiley and Sons Inc., Second edition pp. 9-51, 2005.
N. R. Lomb, "Least-squares frequency analysis of unequally spaced data", Astrophysics and Space Science, vol. 39 Issue 2 pp. 447-462, 1976.
J. D. Scargle, "Studies in astronomical time series analysis. II. Statistical aspects of spectral analysis of unevenly spaced data", The Astrophysical Journal, vol. 263 pp. 835-853, 1982.
Solange Akselrod et al., "Power Spectrum Analysis of Heart Rate Fluctuation: A Quantitative Probe of Beat-to-Beat Cardiovascular Control", Sciencem vol. 213 Issue 4504 pp. 220-223, 1981.
P. E. McSharry et al., "A dynamical model for generating synthetic electrocardiogram signals", IEEE Transactions on Biomedical Engineering, vol. 50 No 3 pp. 289-294, Mar. 2003.

* cited by examiner

Spatial Self-Similarity       Temporal Self-Similarity

NON-INVASIVE ANALYSIS OF SINOATRIAL NODE AND AUTONOMIC NERVOUS INPUT TO HEART FUNCTION

CROSS REFERENCE TO RELATED APPLICATIONS

This application is a national phase PCT Patent Application No. PCT/IL2018/051226 having International filing date of Nov. 14, 2018, which claims the benefit of priority of U.S. Provisional Patent Application No. 62/586,406, filed Nov. 15, 2017, entitled "NON-INVASIVE ANALYSIS OF SINOATRIAL NODE FUNCTION." The contents of the above applications are all incorporated by reference as if fully set forth herein in their entirety.

FIELD OF THE INVENTION

The invention relates to the field of automated heart diagnostics.

BACKGROUND OF THE INVENTION

A multitude of complex processes control heart rate (HR) and its beat to beat changes. Thus, heart rate variability (HRV) signals are essentially some non-linear function of both neural stimulation by the autonomic nervous system (ANS) and the sinoatrial node cells' (SANC)-intrinsic coupled-clock system. For this reason it is not currently possible to tell whether an in-vivo change in HR or HRV is caused by functional changes of the intrinsic SANC mechanisms or by changes in ANS stimulation. It was previously shown that even in the case of single isolated SANC, complex fractal dynamics are present in the beat rate variability (BRV, as opposed to HRV for an in-vivo heart) of these cells. This leads to speculation on whether the origin of HRV lies in fact within the BRV of these single SAN cells. Evidence has been shown to suggest that this is the case, and that HRV is created and influenced at three biological 'levels' of integration: the single SAN cell, which generates complex BRV without external stimulation, the SAN tissue level which modifies BRV due to intra-cellular coupling interactions and finally the level of the in-situ heart which adds extracardial modulation via the ANS (Binah et al., Integrating beat rate variability: From single cells to hearts, Heart Rhythm, 2013).

Studying the origins of HRV at the SANC and tissue levels requires isolation of these cells from the autonomic nervous system. A useful approach to separate the SANC-intrinsic effects from the ANS effects on heart rate is to study the HR/HRV during pharmacological denervation by administering drugs which act as antagonists for the adrenergic and cholinergic receptors of the SANC, effectively abolishing the sympathetic and parasympathetic influence on these cells (respectively). Examples of such drugs are propranolol, a beta-blocker, and atropine which blocks the muscarinic receptors. Both these drugs can be administered together to achieve complete pharmacological denervation of the heart, also referred to as a double blockade. Additionally, they are FDA approved for use on humans, and have a limited duration to their effect which make them an invaluable clinical tool for studying HRV, especially in the context of the heart's intrinsic function.

Instantaneous heart rate measured under pharmacological denervation has been called "intrinsic heart rate" (IHR) It has been shown that the IHR is dynamic and responds to external body conditions such as temperature and exercise in a way similar to the normal heart rate. Studies of IHR in children of various ages have shown that both the HR and the IHR are correlated strongly with age, indicating that the HR reduction in aging is not only due to different levels of autonomic function at different ages (Cummings and Mir, Heart rate and haemodynamics after autonomic blockade in infants and children, British Heart Journal, 1970). These studies used pharmacological denervation as a clinical tool, and have shown that there must be regulatory mechanisms beyond the ANS which determine heart rate.

Pharmacological denervation has also been used to study SANC in animal models. Yaniv et. al. (Yaniv et al., Synchronization of sinoatrial node pacemaker cell clocks and its autonomic modulation impart complexity to heart beating intervals, Heart Rhythm, 2014) studied the properties of heart- and beat-rate variability in rabbits at various levels of integration: heart in vivo (basal state), heart in vivo during double blockade (intrinsic state), isolated SAN tissue and single SAN cell. FIGS. 8A-B shows beating interval duration (FIG. 8A) and distribution (FIG. 8B) of rabbit SANC at different levels of integration, from a full beating heart to a single cell. This study shows similarity in fractal properties of the HRV signals when comparing the intrinsic state and the isolated SAN tissue.

In a more recent study, mouse SAN was studied in the first three integration levels to better understand the cause of HRV reduction with age (Yaniv et al., Deterioration of autonomic neuronal receptor signaling and mechanisms intrinsic to heart pacemaker cells contribute to age-associated alterations in heart rate variability in vivo, Aging Cell, 2016). Again, when comparing the dynamics of the HRV/BRV in the intrinsic and isolated cases, a noticeable similarity can be observed. In a related study, canine pacemaker function was investigated to find the effect of the heart rate itself on HRV, and pharmacological denervation was used for studying HRV in absence of autonomic regulation (Billman, The effect of heart rate on the heart rate variability response to autonomic interventions, Fron. In Physiology, 2013). While these studies focused on different issues, they all provide data to support the use of double blockade as a clinical tool for the analysis of intrinsic pacemaker mechanisms.

The contribution to heart rate from SANC and ANS is still unclear. However, due to the complex nonlinear nature of the heart rate, careful analysis of heart data (ECG for example) using advanced signal processing techniques could hopefully reveal "hidden" information relating to the complex mechanisms behind HRV, and perhaps lead to understanding and quantifying these contributing factors. The ability to separately monitor SANC input and ANS input as it relates to heart healthy would greatly improve the ability to diagnosis and treat the root cause of heart problems.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

According to a first aspect, there is provided a method for evaluating heart function, the method comprising:

receiving a digitized cardiac signal from the heart;
computing a power spectral density (PSD) or multiscale entropy (MSE) of the digitized cardiac signal; and
evaluating at least one of:
a) sinoatrial node (SAN) function of the heart based on the PSD within a frequency range of 0.003 to 0.1 Hertz (Hz), wherein a PSD within the frequency range of 0.003 to 0.1 Hz below a predetermined threshold indicates impaired SAN function;
b) SAN function of the heart based on the MSE within a scale range of 10 to 20, wherein an MSE within the scale range of 10 to 20 below a predetermined threshold indicates impaired SAN function;
c) autonomic nervous system (ANS) input to the heart based on the PSD within a frequency above 0.1 Hz, wherein a PSD within the frequency range of above 0.1 Hz below a predetermined threshold indicates impaired ANS input to the heart; and
d) ANS input to the heart based on the MSE within a scale range of 1 to 10, wherein an MSE within the scale range of 1 to 10 below a predetermined threshold indicates impaired ANS input to the heart;
thereby evaluating heart function.

According to another aspect, there is provided a system configured to:
acquire a digitized cardiac signal;
compute a power spectral density (PSD) or multiscale entropy (MSE) of the digitized cardiac signal; and
evaluate at least one of:
a) sinoatrial node (SAN) function of the heart based on the PSD within a frequency range of 0.003 to 0.1 Hertz (Hz), wherein a PSD within the frequency range of 0.003 to 0.1 Hz below a predetermined threshold indicates impaired SAN function;
b) SAN function of the heart based on the MSE within a scale range of 10 to 20, wherein an MSE within the scale range of 10 to 20 below a predetermined threshold indicates impaired SAN function;
c) autonomic nervous system (ANS) input to the heart based on the PSD within a frequency above 0.1 Hz, wherein a PSD within the frequency range of above 0.1 Hz below a predetermined threshold indicates impaired ANS input to the heart; and
d) ANS input to the heart based on the MSE within a scale range of 1 to 10, wherein an MSE within the scale range of 1 to 10 below a predetermined threshold indicates impaired ANS input to the heart.

According to another aspect, there is provided a computer program product for evaluating heart function, the computer program product comprising a non-transitory computer-readable storage medium having program code embodied therewith, the program code executable by at least one hardware processor to
receive a digitized cardiac signal from the heart;
compute a power spectral density (PSD) or multiscale entropy (MSE) of the digitized cardiac signal; and
evaluate at least one of:
a) sinoatrial node (SAN) function of the heart based on the PSD within a frequency range of 0.003 to 0.1 Hertz (Hz), wherein a PSD within the frequency range of 0.003 to 0.1 Hz below a predetermined threshold indicates impaired SAN function;
b) SAN function of the heart based on the MSE within a scale range of 10 to 20, wherein an MSE within the scale range of 10 to 20 below a predetermined threshold indicates impaired SAN function;
c) autonomic nervous system (ANS) input to the heart based on the PSD within a frequency above 0.1 Hz, wherein a PSD within the frequency range of above 0.1 Hz below a predetermined threshold indicates impaired ANS input to the heart; and
d) ANS input to the heart based on the MSE within a scale range of 1 to 10, wherein an MSE within the scale range of 1 to 10 below a predetermined threshold indicates impaired ANS input to the heart.

According to some embodiments, the digitized cardiac signal comprises temporal data of more than one heart beat.

According to some embodiments, the digitized cardiac signal is an electrocardiogram (ECG) signal.

According to some embodiments, the heart is from a subject at risk of developing, or suffering from, heart disease.

According to some embodiments, the frequency above 0.1 Hz is 0.1 to 0.4 Hz.

According to some embodiments, the computing a PSD or an MSE comprises calculating heart rate variability (HRV) in the digitized cardiac signal.

According to some embodiments, the calculating HRV comprises filtering out ectopic heart beats.

According to some embodiments, the heart function is SAN function, and the method comprises evaluating (a), (b) or both.

According to some embodiments, the heart function is ANS input to the heart, and the method comprises evaluating (c), (d) or both.

According to some embodiments, the method further comprises at least one of:
administering to the subject a SAN medication when the evaluating indicates impaired SAN function, and
administering to the subject an ANS medication when the evaluating indicates impaired ANS function.

According to some embodiments, the SAN medication is selected from a phosphodiesterase inhibitor, and a calcium blocker. According to some embodiments, the phosphodiesterase inhibitor is selected from 3-isobutyl-1-methylxanthine (IBMX) and sildenafil.

According to some embodiments, the ANS medication is a beta blocker.

According to some embodiments, the system comprises an electrocardiograph or heart rate monitor configured to acquire a digitized cardiac signal.

According to some embodiments, the system is further configured to output a diagnosis selected from: healthy heart function, impaired SAN function, impaired ANS input to the heart, and impaired SAN function and impaired ANS input to the heart.

In addition to the exemplary aspects and embodiments described above, further aspects and embodiments will become apparent by reference to the figures and by study of the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION OF THE INVENTION

Figure 1:
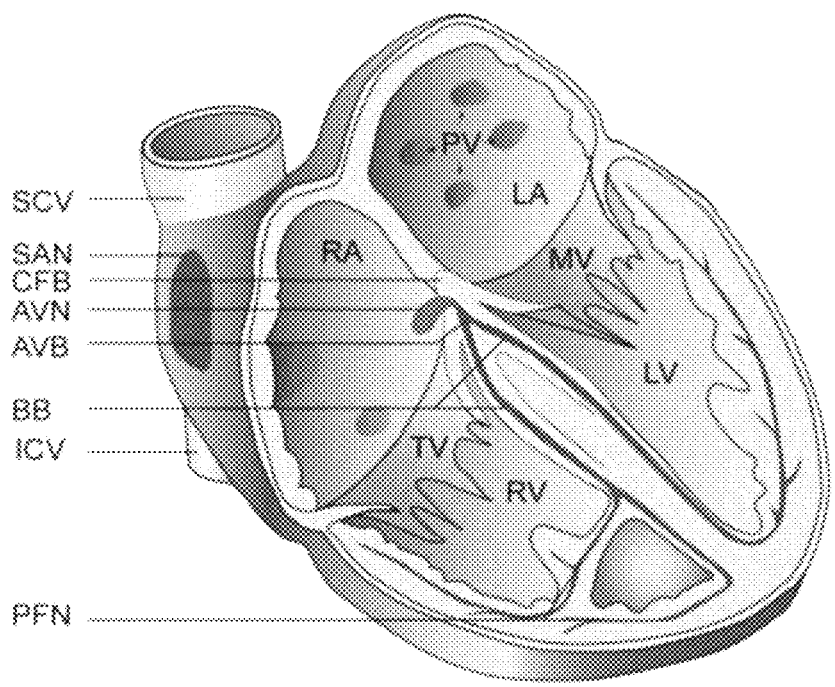
FIG. 1 illustrates the anatomy of the heart, indicating the location of the Sino-Atrial node (SAN), AV node (AVN) and Purkinje fibers (PFN).

Disclosed herein are methods, systems, and computer program products for evaluating heart function; specifically, sinoatrial node (SAN) function and autonomic nervous system (ANS) input to the hearth. The evaluation is performed on the basis of a digitized cardiac signal, and comprises evaluating the power spectral density (PSD) or multiscale entropy (MSE) of the digitized cardiac signal.

According to a first aspect, there is provided a method comprising: receiving a digitized cardiac signal from a heart; computing a power spectral density (PSD) or multiscale entropy (MSE) of the digitized cardiac signal; and evaluating at least one of:
  a) sinoatrial node (SAN) function of the heart based on the PSD within a frequency range of 0.003 to 0.1 Hertz (Hz), wherein a PSD within the frequency range of 0.003 to 0.1 Hz below a predetermined threshold indicates impaired SAN function;
  b) SAN function of the heart based on the MSE within a scale range of 10 to 20, wherein an MSE within the scale range of 10 to 20 below a predetermined threshold indicates impaired SAN function;
  c) autonomic nervous system (ANS) input to the heart based on the PSD within a frequency above 0.1 Hz, wherein a PSD within the frequency range of above 0.1 Hz below a predetermined threshold indicates impaired ANS input to the heart;
  d) ANS input to the heart based on the MSE within a scale range of 1 to 10, wherein an MSE within the scale range of 1 to 10 below a predetermined threshold indicates impaired ANS input to the heart.

In some embodiments, the method is for evaluating heart function. In some embodiments, the method is for evaluating SAN function. In some embodiments, the method is for evaluating ANS function. In some embodiments, the method is for evaluating ANS input to the heart. In some embodiments, the method is for distinguishing the factor causing a cardiac condition, wherein the factor is selected from SAN function and ANS input to the heart.

In some embodiments, the method is for evaluating SAN function and comprises: receiving a digitized cardiac signal from a heart; computing a power spectral density (PSD) or multiscale entropy (MSE) of the digitized cardiac signal; and evaluating at least one of:
a) sinoatrial node (SAN) function of the heart based on the PSD within a frequency range of 0.003 to 0.1 Hertz (Hz), wherein a PSD within the frequency range of 0.003 to 0.1 Hz below a predetermined threshold indicates impaired SAN function; and
b) SAN function of the heart based on the MSE within a scale range of 10 to 20, wherein an MSE within the scale range of 10 to 20 below a predetermined threshold indicates impaired SAN function.

In some embodiments, the method is for evaluating MSE input to the heart and comprises: receiving a digitized cardiac signal from a heart; computing a power spectral density (PSD) or multiscale entropy (MSE) of the digitized cardiac signal; and evaluating at least one of:
a) ANS input to the heart based on the PSD within a frequency above 0.1 Hz, wherein a PSD within the frequency range of above 0.1 Hz below a predetermined threshold indicates impaired ANS input to the heart; and
b) ANS input to the heart based on the MSE within a scale range of 1 to 10, wherein an MSE within the scale range of 1 to 10 below a predetermined threshold indicates impaired ANS input to the heart.

According to another aspect, there is provided a system configured to perform a method of the invention.

According to another aspect, there is provided a computer program product for performing a method of the invention, the computer program product comprising a non-transitory computer-readable storage medium having program code embodied therewith, the program code executable by at least one hardware processor to perform a method of the invention.

In some embodiments, a power spectral density (PSD) of the digitized cardiac signal is computed. In some embodiments, the sinoatrial node function is evaluated based on the PSD within a frequency range of 0.003 to 0.1 Hertz. This range was discovered by the inventors to be unexpectedly advantageous as the sinoatrial node contributes power in the very low frequency (VLF) band, specifically 0.003 to 0.1 Hertz. In some embodiments, the autonomic nervous system input to the heart is evaluated based on PSD within frequency range higher than 0.1 Hz. This range was discovered by the inventors to be unexpectedly advantageous as the ANS contributes power in the low and high frequency (LF and HF) bands.

In some embodiments, a multiscale entropy (MSE) of the digitized cardiac signal is computed. In some embodiments, the sinoatrial node function is evaluated based on the MSE within a scale range of 10 to 20. This range was discovered by the inventors to be unexpectedly advantageous as the sinoatrial node contributes pseudo-random noise which is observable mainly in the lower scales of the MSE. In some embodiments, the autonomic nervous system input to the heart is evaluated based on MSE within a scale range of 1 to 10. This range was discovered to be unexpectedly advantageous as the ANS contributes pseudo-random noise which is observable mainly in the lowest scales of the MSE.

The results provided herein below confirm that the power spectral density (PSD) of a cardiac signal is indicative of sinoatrial node function in the VLF range. In some embodiments, SAN function is evaluated in the VLF range. In some embodiments, the VLF range is between 0.003 to 0.1 Hertz. In some embodiments, the VLF range is between 0.003 and 0.03, 0.003 and 0.05, 0.003 and 0.07, 0.003 and 0.09, 0.003 and 0.1, 0.003 and 0.11, 0.003 and 0.12, 0.003 and 0.13, 0.003 and 0.14, 0.003 and 0.15, 0.005 and 0.03, 0.005 and 0.05, 0.005 and 0.07, 0.005 and 0.09, 0.005 and 0.1, 0.005 and 0.11, 0.005 and 0.12, 0.005 and 0.13, 0.005 and 0.14, 0.005 and 0.15, 0.007 and 0.03, 0.007 and 0.05, 0.007 and 0.07, 0.007 and 0.09, 0.007 and 0.1, 0.007 and 0.11, 0.007 and 0.12, 0.007 and 0.13, 0.007 and 0.14, 0.007 and 0.15, 0.009 and 0.03, 0.009 and 0.05, 0.009 and 0.07, 0.009 and 0.09, 0.009 and 0.1, 0.009 and 0.11, 0.009 and 0.12, 0.009 and 0.13, 0.009 and 0.14, 0.009 and 0.15, 0.011 and 0.03, 0.0011 and 0.05, 0.011 and 0.07, 0.0011 and 0.09, 0.011 and 0.1, 0.011 and 0.11, 0.011 and 0.12, 0.01 and 0.13, 0.011 and 0.14, 0.011 and 0.15, 0.013 and 0.03, 0.013 and 0.05, 0.013 and 0.07, 0.013 and 0.09, 0.013 and 0.1, 0.013 and 0.11, 0.013 and 0.12, 0.013 and 0.13, 0.013 and 0.14, 0.013 and 0.15, 0.015 and 0.03, 0.0015 and 0.05, 0.015 and 0.07, 0.015 and 0.09, 0.015 and 0.1, 0.015 and 0.11, 0.015 and 0.12, 0.015 and 0.13, 0.015 and 0.14, or 0.015 and 0.15. Each possibility represents a separate embodiment of the invention.

In some embodiments, ANS input to the heart is evaluated in the LF and/or HF range. In some embodiments, the LF and/or HF ranges from 0.1 Hertz and above. In some embodiments, the ANS input to the heart is evaluated at 0.1 Hz. In some embodiments, the ANS input to the heart is evaluated at a range 0.1, 0.11, 0.12, 0.13, 0.14, 0.15, 0.16, 0.17, 0.18, 0.19, or 0.2 and above. Each possibly represents a separate embodiment of the invention. In some embodiments, the ANS input to the heart is evaluated at a range of 0.1 to 0.4 Hz. In some embodiments, the ANS input to the heart is evaluated at a range of 0.1 to 0.2, 0.1 to 0.3, 0.1 to 0.4, 0.1 to 0.5, of 0.11 to 0.2, 0.11 to 0.3, 0.11 to 0.4, 0.11 to 0.5, of 0.12 to 0.2, 0.12 to 0.3, 0.12 to 0.4, 0.12 to 0.5, of 0.13 to 0.2, 0.13 to 0.3, 0.13 to 0.4, 0.13 to 0.5, of 0.14 to 0.2, 0.14 to 0.3, 0.14 to 0.4, 0.14 to 0.5, of 0.15 to 0.2, 0.15 to 0.3, 0.15 to 0.4, or 0.15 to 0.5 Hz. Each possibility represents a separate embodiment of the invention.

Figure 19A:
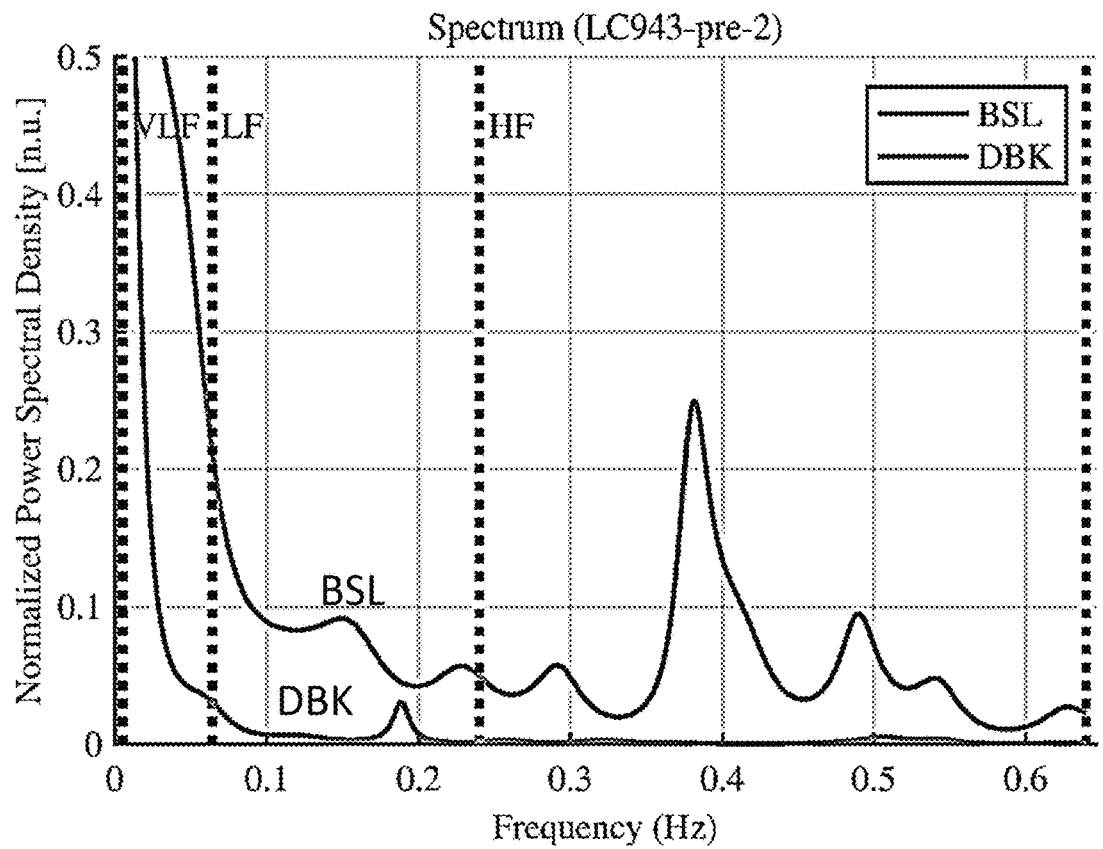
FIG. 19A shows normalized PSD as a function of frequency, before and after autonomic denervation.

In the above frequency range, a patient suffering from SAN malfunction will demonstrate a lower PSD than a healthy subject, or even zero PSD. For example, with reference to FIG. 19A, SAN malfunction may be diagnosed when the PSD values are lower than those shown by the BSL graph (BSL). In some embodiments, SAN malfunction or defect is diagnosed when the PSD values in the frequency range are below a predetermined threshold. In some embodiments, ANS input to the heart malfunction or defect is diagnosed when the PSD values in the proper frequency range are below a predetermined threshold. In some embodiments, the PDS values in the frequency range are lower than the predetermined threshold by at least 10%, 20%, 30%, 40%, 50%, 60%, 70%, 80%, 90%, 95%, 97%, 99% or 100%. In some embodiments, SAN malfunction is a cardiac disease. In some embodiments, SAN malfunction is indicative of a cardiac disease. Examples of cardiac disease include, but are not limited to atrial fibrillation, heart failure, and sick sinus syndrome.

Furthermore, the present PSD technique may also be used for diagnosing ANS pathologies, when the PSD in the LF and/or HF is lower than a threshold that was predetermined for healthy subjects. In some embodiments, the predetermined threshold is determined in healthy subjects. In some embodiments, the predetermined threshold is determined from digitized cardiac signals from healthy subjects. In some embodiments, the predetermined threshold is determined in resting subjects. In some embodiments, the predetermined threshold is determined in exercised subjects.

The results provided herein below further confirm that the multiscale entropy (MSE) of a cardiac signal is indicative of sinoatrial node function within a scale range of, 8 to 20, 9 to 20, 10 to 20, 11 to 20, 12 to 20, 13 to 20, 14 to 20, 8 to 19, 9 to 19, 10 to 19, 11 to 19, 12 to 19, 13 to 19, 14 to 19, 8 to 18, 9 to 18, 10 to 18, 11 to 18, 12 to 18, 13 to 18, 14 to 18, 8 to 17, 9 to 17, 10 to 17, 11 to 17, 12 to 17, 14 to 17, 8 to 16, 9 to 16, 10 to 16, 11 to 16, 12 to 16, 13 to 16, 14 to 16, 8 to 15, 9 to 15, 10 to 15, 11 to 15, 12 to 15, 13 to 15 or 14 to 15. Each possibility represents a separate embodiment of the invention, and ending at scale 19, 18, 17, 16, or 15. In some embodiments, a lower scale range in the MSE is indicative of sinoatrial node function.

In some embodiments, the present MSE technique may also be used for diagnosing ANS pathologies and/or ANS input to the heart, wherein the MSE in lower scales is lower than a threshold that was predetermined for healthy subjects. In some embodiments, lower scales are between 1 and 10, 1 and 9, 1 and 8, 1 and 7, 1 and 6, 1 and 5, 2 and 10, 2 and 9, 2 and 8, 2 and 7, 2 and 6, 2 and 5, 3 and 10, 3 and 9, 3 and 8, 3 and 7, 3 and 6, 3 and 5, 4 and 10, 4 and 9, 4 and 8, 4 and 7, 4 and 6 or 4 and 5. Each possibility represents a separate embodiment of the invention.

In some embodiments, atrial fibrillation may be diagnosed when the MSE curve resembles white noise. This make sense, since during atrial fibrillation electrical activity is not generated in the SAN. In some embodiments, a ANS input to the heart defect or malfunction is atrial fibrillation.

In some embodiments, congestive heart failure may be diagnosed when the MSE entropy both on the low (any range below 10) and high scales (any range above 10) is lower than in a healthy subject. In some embodiments, an MSE in a lower scale range that is lower than a predetermined threshold is indicative of congestive heart failure. In some embodiments, an MSE in a higher range (10-20 range or ranges in between) lower than a predetermined threshold is indicative of congestive heart failure. In some embodiments, MSE over any range that is lower than a predetermined threshold is indicative of congestive heart failure.

In some embodiments, computing a PSD and/or MSE comprises calculating HRV in the digitized cardiac signal. In some embodiments, calculating HRV comprises filtering ectopic heart beats. In some embodiments, calculating HRV comprises filtering out false beats. In some embodiments, an ectopic beat is an ectopic peak. In some embodiments, HRV is calculated from peak intervals, NN intervals, RR intervals or a combination thereof. In some embodiments, HRV is calculated from NN intervals. In some embodiments, peaks are determined using a 'gqrs' algorithm or detector. In some embodiments, the 'gqrs' algorithm or detector is a modified 'gqrs' algorithm or detector. In some embodiments, the modified 'gqrs' algorithm or detector is a 'rqrs' algorithm or detector.

Methods of peak detection and interval determination are described herein and are well known in the art. Any method of determining HRV known in the art may be employed to practice this invention. Methods of computing PSD and MSE are described herein and are well known in the art. Any method of computing PSD and/or MSE known in the art may be employed to practice this invention.

In some embodiments, prior to computing the PSD or the MSE, ectopic beats are removed from the digitized cardiac signal. As used herein, an "ectopic beat" is a disturbance of the cardiac rhythm frequently related to the electrical conduction system of the heart, in which beats arise from fibers or group of fibers outside the SAN. Hence, excluding these beats from the evaluation cardiac function greatly enhances accuracy.

In some embodiments, the heart is from a subject. In some embodiments, the subject is a human. In some embodiments, the subject is a mammal. In some embodiments, the subject is a canine. In some embodiments, the heart is from a subject in need of heart function evaluation. In some embodiments, the subject is at risk of developing a heart disease or condition. In some embodiments, the subject suffers from a heart disease or condition. Numerous risk factors are known for heart disease, and a subject at risk for such a disease may present with any of those risk factors. Risk factors include, but are not limited to smoking, being over weight, genetic family history of heart disease, diabetes and a preexisting heart condition.

In some embodiments, the method further comprises administering to the subject a medication for the evaluated impaired cardiac function. In some embodiments, the medication is a SAN medication and the evaluating indicates impaired SAN function. In some embodiments, the medication is an ANS medication and the evaluating indicates impaired ANS function. In some embodiments, the method further comprises treating based on the indicated impairment. In some embodiments, the method is a method of evaluating and treating.

In some embodiments, the SAN medication is selected from a phosphodiesterase inhibitor, and a calcium blocker. In some embodiments, the phosphodiesterase inhibitor is selected from 3-isobutyl-1-methylxanthine (IBMX) and sildenafil (Viagra). Medications directed to SAN or pacemaker cells are well known in the art and any such medication may be used. In some embodiments, the ANS medication is a beta-adrenergic blocking agent (beta-blocker). Beta-blockers are well known in the art and include for example acebutolol, atenolol, bisoprolol, metoprolol, nadolol, nebivolol, propranolol to name but a few.

In some embodiments, the system is an electrocardiography system. In some embodiments, the system is configured to:
acquire a digitized cardiac signal;
compute a power spectral density (PSD) or multiscale entropy (MSE) of the digitized cardiac signal; and
evaluate at least one of:
a) sinoatrial node (SAN) function of the heart based on the PSD within a frequency range of 0.003 to 0.1 Hertz (Hz), wherein a PSD within the frequency range of 0.003 to 0.1 Hz below a predetermined threshold indicates impaired SAN function;
b) SAN function of the heart based on the MSE within a scale range of 10 to 20, wherein an MSE within the scale range of 10 to 20 below a predetermined threshold indicates impaired SAN function;
c) autonomic nervous system (ANS) input to the heart based on the PSD within a frequency above 0.1 Hz, wherein a PSD within the frequency range of above 0.1 Hz below a predetermined threshold indicates impaired ANS input to the heart; and
d) ANS input to the heart based on the MSE within a scale range of 1 to 10, wherein an MSE within the scale range of 1 to 10 below a predetermined threshold indicates impaired ANS input to the heart.

The system may be embodied in an electrocardiography (ECG) system, which includes electrodes, circuitry, and a processor for acquiring electrocardiograms—as known in the art, with the addition of software for executing the present technique for evaluating SAN function. The software may run on the ECG system's own processor, or on a separate processor operatively coupled to it. In some embodiments, the system comprises an electrocardiograph.

The system may be embodied in a heart rate monitor, such as a bracelet or a wristwatch that include, inter alia, heart rate monitoring functionality, as known in the art. The present technique for evaluating SAN function may be a software program running on a processor of the heart rate monitor. Alternatively, the software program may run on a separate computerized device which receives heart rate data from the heart rate monitor, such as a personal computer, a handheld computer, or a network-accessible remote server. In some embodiments, the system comprises a heart rate monitor. In some embodiments, the heart rate monitor is configured to acquire a digitized cardiac signal. In some embodiments, the heart rate monitor is configured to acquire a cardiac signal and digitize it.

The term "digitized cardiac signal", as referred to herein, is meant to cover any cardiac signal represented digitally. In some embodiments, the digitized cardiac signal comprises temporal information of more than one heart beat. For example, the digitized cardiac signal may be beat-to-beat interval data, a time series of detected heart beats, an electrocardiogram, or the like. In some embodiments, the digitized cardiac signal comprises beat-to-beat heart data. In some embodiments, the beat-to-beat heart data is beat-to-beat interval data. In some embodiments, the digitized cardiac signal is an electrocardiography (ECG) signal. In some embodiments, the digitized cardiac signal is an ECG. In some embodiments, the digitized cardiac signal is data from a heart rate monitor.

In some embodiments, the digitized cardiac signal comprises at least 10, 20, 30, 40, 50, 60, 70, 80, 90, 100, 120, 140, 160, 180, 200, 220, 240, 260, 280, 300, 320, 340, 360, 380, 400, 420, 440, 460, 480 or 500 beats. Each possibility represents a separate embodiment of the invention. In some embodiments, the digitized cardiac signal comprises at least 0.5, 1, 1.5, 2, 2.5, 3, 3.5, 4, 4.5, 5, 5.5, 6, 7, 8, 9 or 10 minutes of cardiac signal. Each possibility represents a separate embodiment of the invention. In some embodiments, the cardiac signal is a continuous signal.

In some embodiments, the system is further configured to output a diagnosis. In some embodiments, the diagnosis is selected from: healthy heart function, impaired SAN function, imparted ANS input to the heart and impaired SAN function and impaired ANS input to the heart.

The present invention may be a system, a method, and/or a computer program product. The computer program product may include a computer readable storage medium (or media) having computer readable program instructions thereon for causing a processor to carry out aspects of the present invention.

In some embodiments, the computer program product is for evaluating heart function. In some embodiments, the computer program product comprises a non-transitory computer-readable storage medium having program code embodied therewith, the program code executable by at least one hardware processor to
  receive a digitized cardiac signal from the heart;
  compute a power spectral density (PSD) or multiscale entropy (MSE) of the digitized cardiac signal; and
  evaluate at least one of:
  a) sinoatrial node (SAN) function of the heart based on the PSD within a frequency range of 0.003 to 0.1 Hertz (Hz), wherein a PSD within the frequency range of 0.003 to 0.1 Hz below a predetermined threshold indicates impaired SAN function;
  b) SAN function of the heart based on the MSE within a scale range of 10 to 20, wherein an MSE within the scale range of 10 to 20 below a predetermined threshold indicates impaired SAN function;
  c) autonomic nervous system (ANS) input to the heart based on the PSD within a frequency above 0.1 Hz, wherein a PSD within the frequency range of above 0.1 Hz below a predetermined threshold indicates impaired ANS input to the heart; and
  d) ANS input to the heart based on the MSE within a scale range of 1 to 10, wherein an MSE within the scale range of 1 to 10 below a predetermined threshold indicates impaired ANS input to the heart.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

EXAMPLES

The following examples are meant to illustrate, but in no way to limit, the claimed invention. The following examples represent embodiments of the claimed invention.

Materials and Methods
The Sinoatrial Node

The sinoatrial (SA) node is the primary "pacemaker" of the heart. The SA node is a region, located in the right atrium, composed of specialized cardiac cells (SA node cells, or SANCs) which spontaneously generate action-potentials (APs) at almost regular intervals causing the heart to contract. FIG. 1, illustrates the anatomy of the heart, indicating the location of the Sino-Atrial node (SAN), AV node (AVN) and Purkinje fibers (PFN).

While other cardiac cells such as the AVN cells and Purkinje fibers are also known to produce spontaneous APs, the SANCs are considered the primary source of the heart rhythm because they have a faster intrinsic beating rate, suppressing the pacemaking of other cardiac fibers.

As opposed to non-pacemaking cardiomyocytes, SANCs exhibit diastolic depolarization (DD), a constant gradual increase in membrane potential during diastole which culminates when the membrane excitation threshold potential is reached, causing an AP to be fired. Following the AP, the cell membrane repolarizes, and again due to the constant diastolic depolarization the next AP is eventually triggered. The mechanisms behind SANC pacemaking have long been studied and various theories have been proposed as to which intracellular mechanisms carry the more prominent role.

Figure 2:
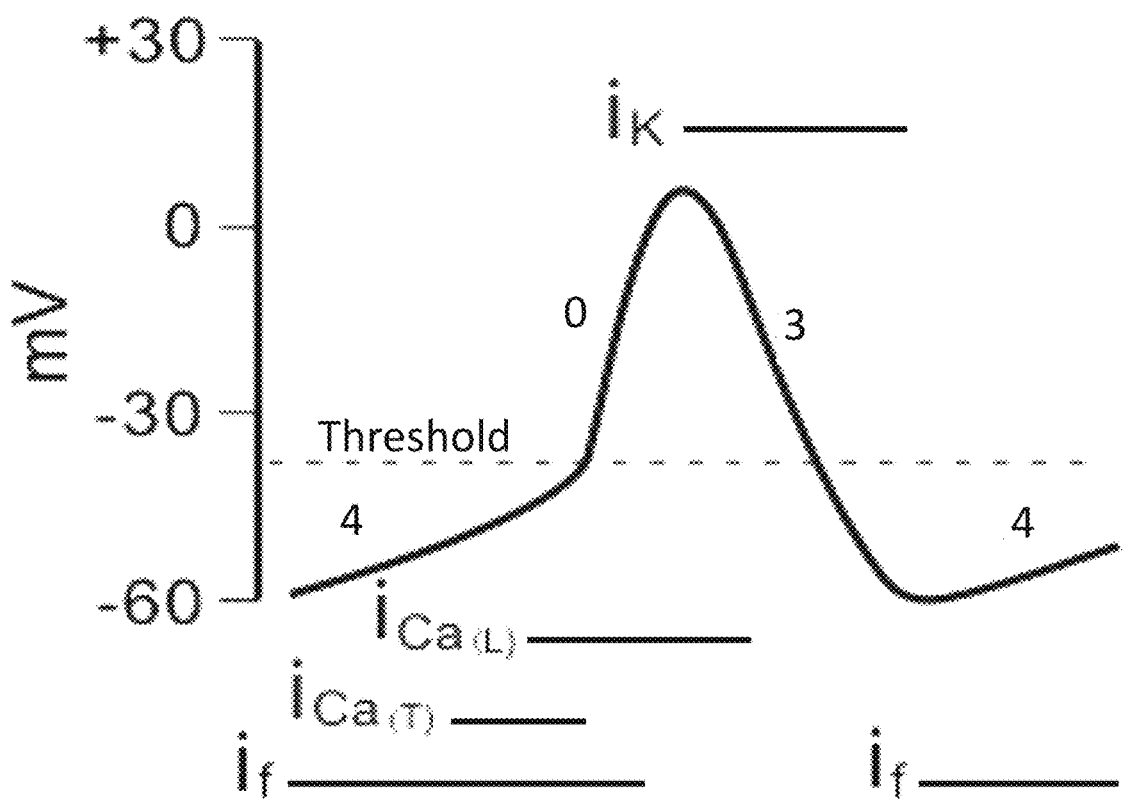
FIG. 2 illustrates schematic action potential in SANC, showing the development of the AP with the corresponding ion currents.

One long-standing theory is that the predominant mechanism behind SANC automaticity is the hyperpolarization-activated ("funny") current, $I_f$. This is a slow inward current of $Na^+$ and $K^+$, mediated through a voltage-dependent ion channel known as the f-channel. The f-channel is unique in that it is activated by membrane hyperpolarization. Therefore, during diastole the f-channels induce a steady stream of depolarizing ions into the SANC. This depolarization then causes activation of voltage-dependent calcium channels (L-type and T-type). Activation of these channels causes a rapid influx of $Ca^{2+}$ ($I_{Ca2+,L}$, $I_{Ca2+,T}$), which leads to depolarization threshold crossing and thus AP firing. FIG. 2, illustrates schematic AP in SANC, showing the development of the AP with the corresponding ion currents. The regions marked '4' correspond to the diastolic depolarization phase.

A more recent theory regarding SANC automaticity is that both sarcolemmal (myocyte membrane) ion channels and the SANC sarcoplasmic reticulum (SR) work together though $Ca^{2+}$ signaling to produce the periodic AP firing (detailed further below). In myocytes, the SR is a cell region that acts as a $Ca^{2+}$ store. $Ca^{2+}$ is released from the SR through Ryanodine channels found on the SR and pumped back in using an active transport known as the SERCA pump (Sarco-/Endoplasmic Reticulum Ca2+-ATPase). Recent evidence has shown that during SANC diastolic depolarization, there are localized spontaneous $Ca^{2+}$ releases (LCRs) from the SR. These LCRs where found be rhythmic, corresponding very closely to the heart-beat cycle length, and non-dependent on membrane depolarization (e.g. due to $I_f$). In addition, the role of $I_f$ as a leading contributor to DD has been disputed, as evidence suggests that the Na+/$Ca^{2+}$-exchanger (NCX) might be a more prominent contributing factor. The NCX generates a net inward current by exchanging one $Ca^{2+}$ ion (going out) with three $Na^+$ ions (coming in). During late diastole, when intracellular $Ca^{2+}$ concentration is on the rise due to LCR, the NCX contributes to the depolarization of the cell by generating inward current. This depolarization then activates voltage dependent $Ca^{2+}$ channels such as L-type and T-type channels, which drive the depolarization across the AP threshold. The NCX continues to generate inward current even at high membrane potentials right before and during AP. In comparison, the 'funny-current' channel produces inward current at a much lower amplitude during DD, and reverses direction following AP.

Figure 3:
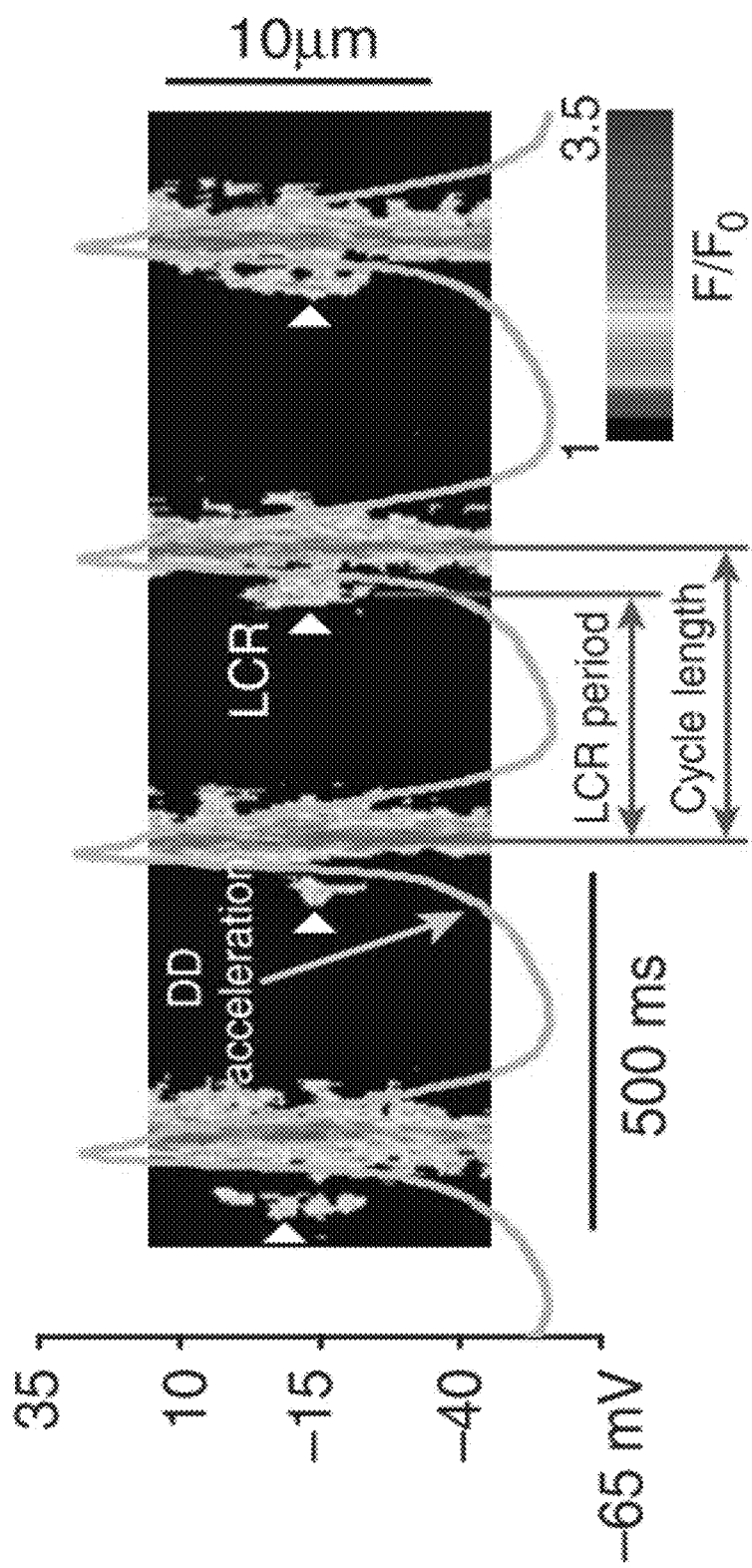
FIG. 3 shows confocal linescans of Ca2+ cycling in SANC (background) and the simultaneous recording of membrane potential (overlay), shown on the same time axis.

FIG. 3 shows confocal linescans of $[Ca^{2+}]$ in SANC (background) and the simultaneous recording of membrane potential (overlay), shown on the same time axis. This demonstrates how LCRs occur periodically just before AP firing occurs.

The control of heart rate and rhythm has been classically attributed to the autonomic nervous system (ANS). It is widely accepted that sympathetic neural stimulus of β-adrenergic receptors increase the heart rate while parasympathetic stimulus of cholinergic receptors decrease it. Both receptors are found on the membrane of pacemaker cells in the SAN.

Stimulation of β-receptors by Norepinephrine, a neurotransmitter released by the ANS sympathetic branch, causes activation of coupled G-proteins which then bind and activate Adenyl Cyclase (AC), a membrane enzyme that catalyzes the conversion of cellular ATP into cyclic-AMP (cAMP). Cyclic AMP then has two main effects:

First, it directly increases activation of the 'funny-current' channels found on the pacemaker cell membrane. This increased activation manifests in a steeper voltage curve during depolarization, and therefore increased AP firing rate.

Second, it activates Protein Kinase A (PKA) a key enzyme which causes phosphorylation of other proteins, some of which are:

Phospholamban (PLB), a protein that normally inhibits the function of the SERCA pump. Phosphorylation of PLB reduces it's inhibitory ability, thus increasing SERCA activity, so more $Ca^{2+}$ is pumped back into the SR. Increased SERCA activation therefore shortens recovery time following an AP, manifesting in increased heart-rate.

Ryanodine receptor (RyR) $Ca^{2+}$ channels. These channels exist on the SR in the sub-membrane space. Their function is to release $Ca^{2+}$ from the SR. Phosphorylation of RyR channels increases their activation, causing increased $Ca^{2+}$ release from the SR into the cell. $Ca^{2+}$ release from SR induces NCX-mediated depolarization, so phosphorylation of RyR also increases the heart rate.

L-type Ca2+ channels. These voltage-dependent $Ca^{2+}$ produce increased inward $Ca^{2+}$ current when phosphorylated. Because L-type $Ca^{2+}$ channels contribute to the slope of the DD curve, this again contributes to an increased heart rate.

Figure 4:
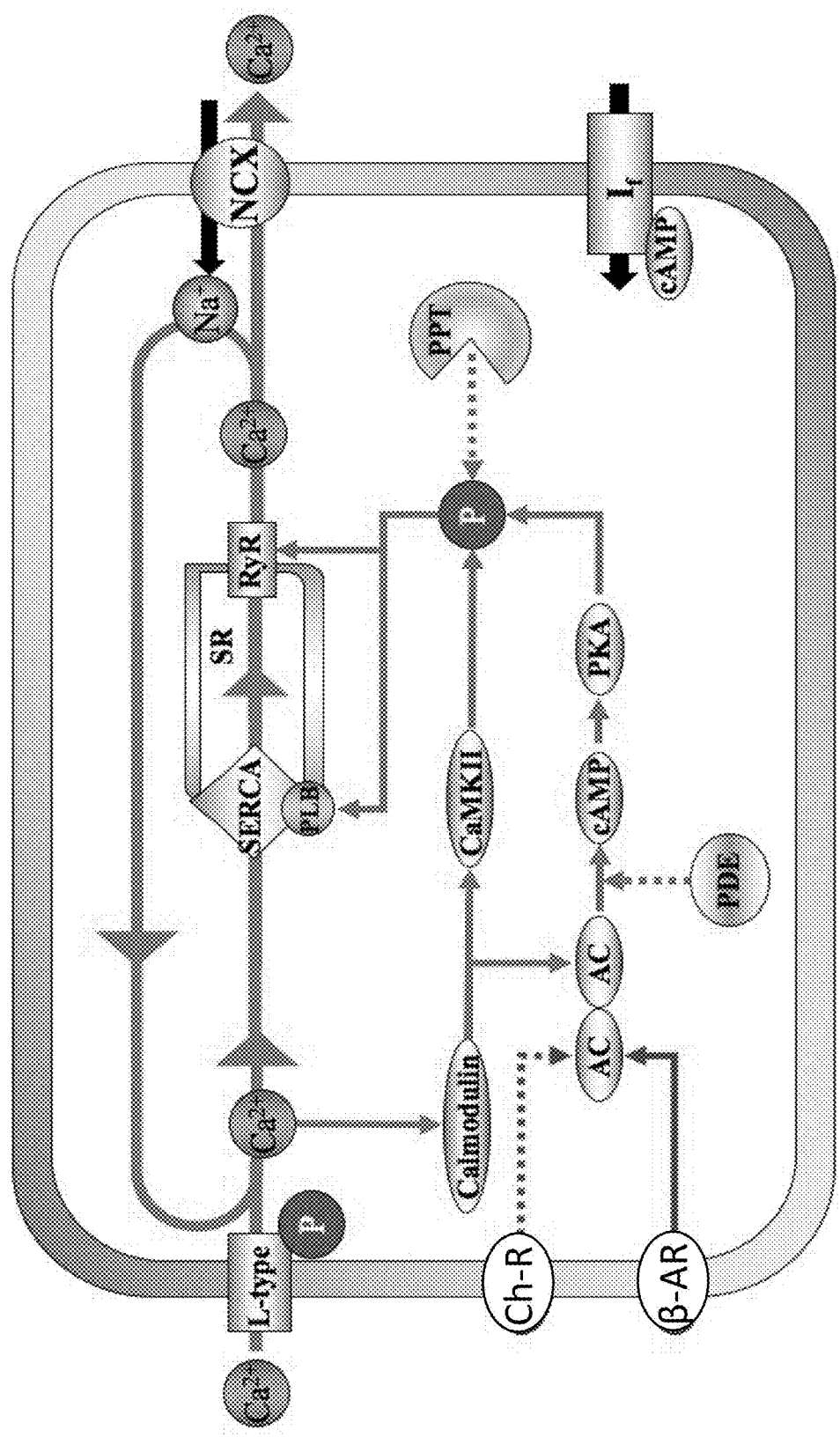
FIG. 4 is a schematic illustration of the various mechanisms affecting SANC AP firing rate and the interplay between them.

Thus, β-receptor stimulation by the ANS increases heart rate by affecting various cellular mechanisms, mainly through phosphorylation, but also via direct influence of $I_f$ (see also FIG. 4). In contrast, stimulation by Acetylcholine (ACh) of the muscarinic receptor by the parasympathetic nervous system has the opposite effect: reduction of cAMP which in turn reduces $I_f$ and PKA-dependent phosphorylation. However, even though the two branches of the ANS have opposite effects on the heart rate, normally both are in different states of activation. This simultaneous interaction results in complex non-additive interactions in the SANC which makes the ANS effect on the heart rate hard to predict.

Recent studies have shown that there is a non-linear connection between autonomic nerve stimulus and heat rate. The pacemaker system activity is thus not only a function of the ANS input, but rather the intrinsic properties of the SANC themselves also play a key role in determining the heart rate. In order to understand the determinants of heart rate, we must first understand how intrinsic clock-like mechanisms generate the APs of SANC.

According to the "coupled-clock theory" of SANC activation, AP firing in the SANC cells is governed by a complex system comprised of two intrinsic intercellular mechanisms ('clocks'), which affect each other via $Ca^{2+}$ signaling and phosphorylation cascades. The first is the $Ca^{2+}$ clock, controlled by the SR which periodically generates LCRs from ryanodine channels. The second is the membrane clock, comprised of sarcolemmal electrogenic molecules, the most prominent ones being the NCX, L-type calcium channel and funny-current channel. The two clocks work together to produce the periodic AP firing in SANC cells (FIG. 4). LCRs activate the NCX, depolarizing the cell by increasing the inward current $I_{NCX}$. When depolarization causes membrane potential to reach the L-type channel voltage threshold, these channels become activated causing a strong $Ca^{2+}$ influx. This in turn enhances $Ca^{2+}$-induced $Ca^{2+}$ releases from the SR. Increased $Ca^{2+}$ levels induce activation of PKA and $Ca^{2+}$/calmodulin-dependent protein kinase (CaMKII) through calmodulin. PKA and CaMKII signaling cascades phosphorylate, and therefore increase activation of, ryanodine channels, L-Type channels and phospholamban. Phosphorylation of phospholamban increases SERCA activity, causing the SR to refill with $Ca^{2+}$ after the AP has been fired. The SR is thus reset and the process can repeat itself.

To prevent the positive feedback loop of $Ca^{2+}$ release that would otherwise occur, several dampening factors, which are also triggered by high $Ca^{2+}$ levels, exist in SANC. The first is phosphodiesterase (PDE) activity which degrades cAMP production. Another dampening factor is phosphoprotein phosphatase (PPT), which directly limits phosphorylation of the key proteins discussed previously. Another factor restraining the coupled-clock system is voltage dependent negative feedback caused by ion channels such as the potassium channels which generate a repolarizing current ($I_k$) which limits $Ca^{2+}$ influx via $I_{Ca2+,L}$.

FIG. 4 is a schematic illustration of the various mechanisms affecting SANC AP firing rate and the interplay between them. ANS input via neurotransmitter receptors; Phosphorylation cascade; and cycling of $Ca^{2+}$ due to LCRs are all shown. Dashed lines indicate negative effect.

This process is further influenced by the autonomic nervous system, which controls heart rate indirectly via sympathetic and parasympathetic stimulation of SANC. As detailed above, sympathetic stimulation via β-adrenergic receptors activates PKA, which causes the same phosphorylation cascades as described above, leading to a higher LCR rate and therefore an increased heart rate. Cholinergic receptor stimulation has the opposite effect of decreasing the $Ca^{2+}$ balance through reduction of PKA-dependent phosphorylation of $Ca^{2+}$ cycling proteins. Thus, the ANS stimulation of the pacemaker cells works by influencing the same cellular mechanisms that govern the intrinsic pacemaker function, essentially controlling the degree of $Ca^{2+}$ cycling and protein phosphorylation.

Heart Rate and Heart Rate Variability

Figure 5:
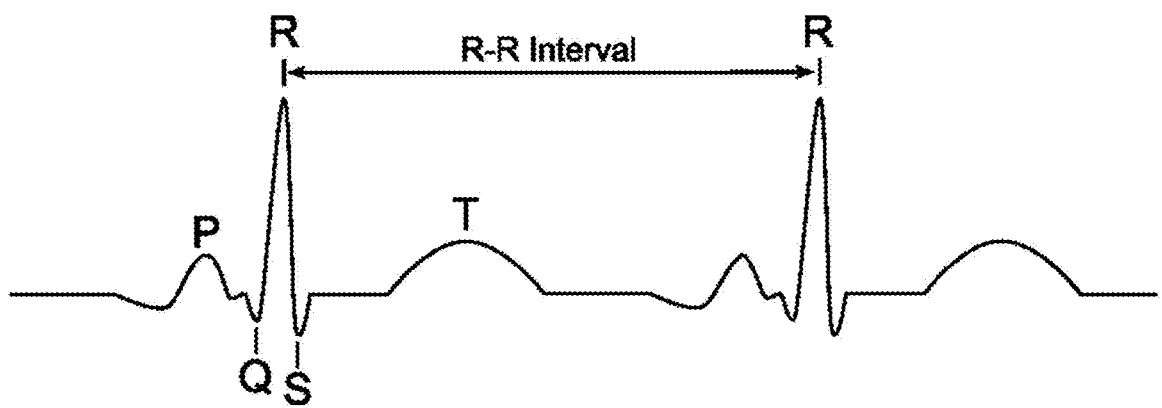
FIG. 5 shows the most prominent electrical events present in each heart beat and their ECG manifestations.

The heart rate is defined as the number of times a subject's heart beats per unit of time, usually measured as beats per minute (BPM). One way to obtain the heart rate is by using Electrocardiography (ECG), a method of recording the electrical activity of the heart by using electrodes placed on a subjects skin. The ECG shows the magnitude and direction of the total electrical activity of the heart (usually in volts) as a function of time. For every heart beat, the ECG trace shows a characteristic progression of the electrical activity of the heart. FIG. 5 shows the most prominent electrical events present in each heart beat and their ECG manifestations:

Atrial depolarization (P-wave). Corresponds to contraction of the atria, due to the electrical current originated at the SAN and directed towards the AVN.

Ventricular depolarization (QRS-complex). Corresponds to contraction of the ventricles. Visually, the QRS complex is more pronounced and "spiked" due to the larger muscle mass of the ventricles, and the fast conduction velocity of the His/Purkinje fibers.

Ventricular repolarization (T-wave), corresponding to repolarization and recovery of the ventricles.

From an ECG trace, the heart rate can be calculated by measuring the number of R-peaks per unit time. The time-difference between two adjacent R-peaks is called an RR-interval. Given a time series of N RR-intervals obtained from an ECG trace, $$\{t_i, RR_i\}_{i=0}^{N-1} \quad (1)$$

where $RR_i$ is the interval length in seconds recorded at time $t_i$, we can obtain an instantaneous heart rate signal in BPM units as $$\left\{t_i, \frac{60}{RR_i}\right\}_{i=0}^{N-1} \quad (2)$$

Figure 6A:
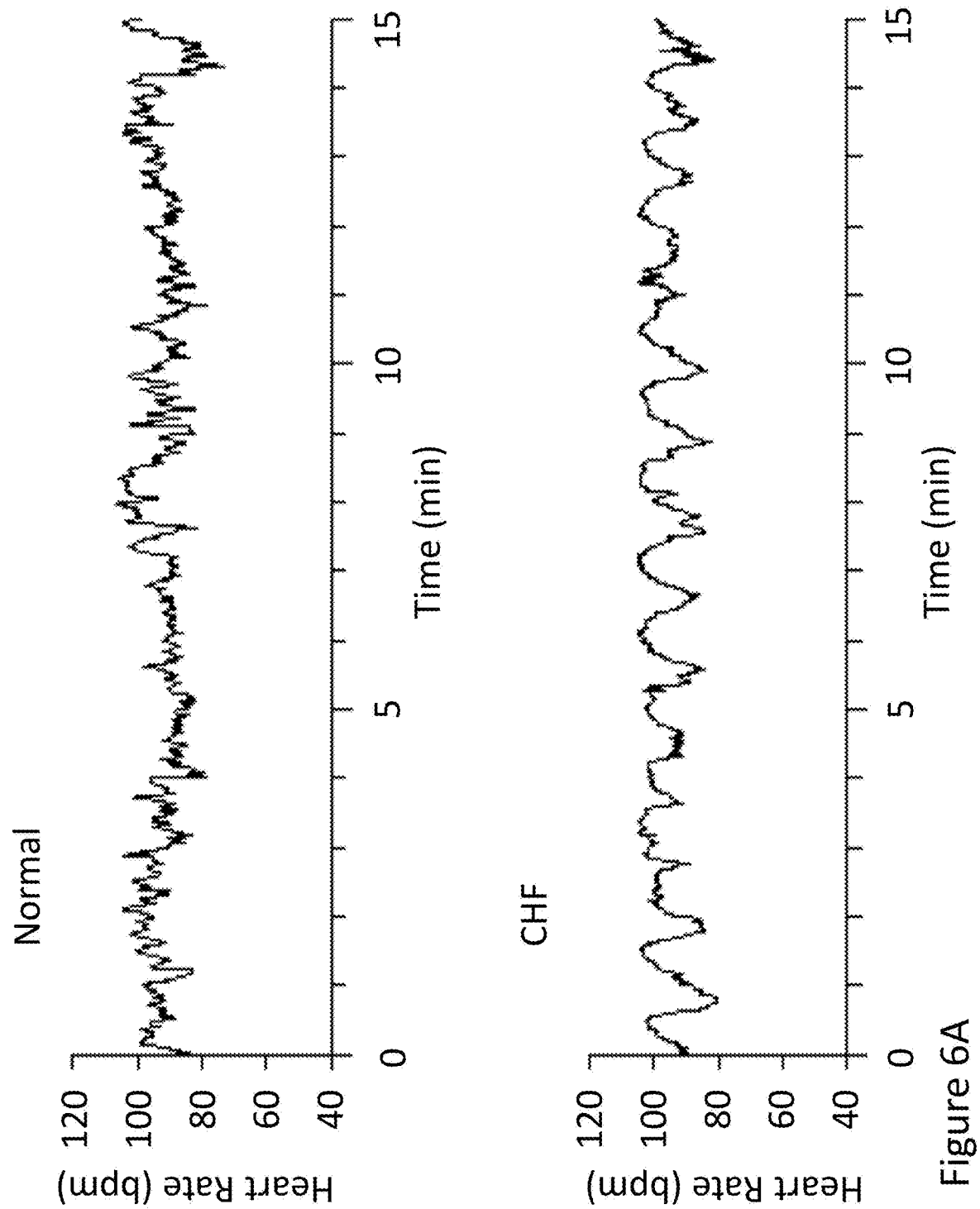
FIG. 6A shows a heart rate time series from a healthy subject and from a patient with severe congestive heart failure (CHF).

(see an example in FIG. 6A). Both these signals can be analyzed using various metrics and techniques.

Figure 6B:
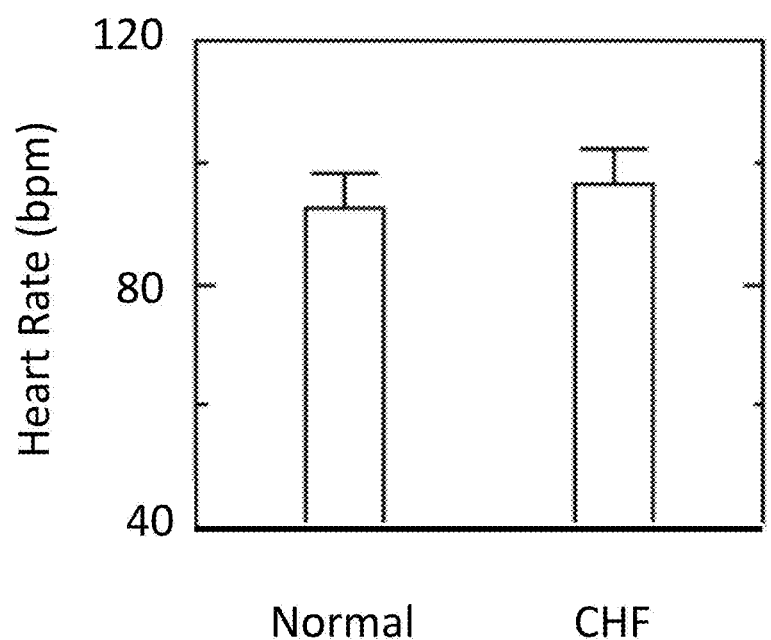
FIG. 6B shows the bean (top of each box) and standard deviation (line above each box) for both of the time series of FIG. 6A.

Surprisingly, even under resting conditions in healthy mammals, the ECG reveals a complex beat-to-beat variation of RR interval duration. In fact, contrary to most other physiological systems, which strive to attain homeostasis, the heart rate never achieves a steady-state due to the dynamic nature of the processes that control it (discussed above). This constant variation of the heart rate on a beat to beat basis is known as heart rate variability (HRV, for an intact in-vivo heart) or beat rate variability (BRV, for SAN tissue or cells), and has been widely studied, analyzed and quantified using various metrics. Loss of heart-rate variability (HRV) is known to be related to increased morbidity and mortality and can be caused by disease and aging. FIG. 6A shows an example of this phenomenon—heart rate time serieses from a healthy subject and from a patient with severe congestive heart failure (CHF). The healthy subject displays irregular dynamics and therefore much higher HRV. Widely different dynamics are seen despite very similar means and variances. FIG. 6B shows the mean (top of each box) and standard deviation (line above each box) for both of the time series of FIG. 6A. Contrary to intuition, to a certain extent the chaotic and irregular signal is the healthy one. However, the mechanisms that induce this reduction in unhealthy hearts are not clear; contributing factors of HRV loss vary per pathology and may lie in ANS function, intrinsic pacemaker mechanisms or both.

Figure 7A:
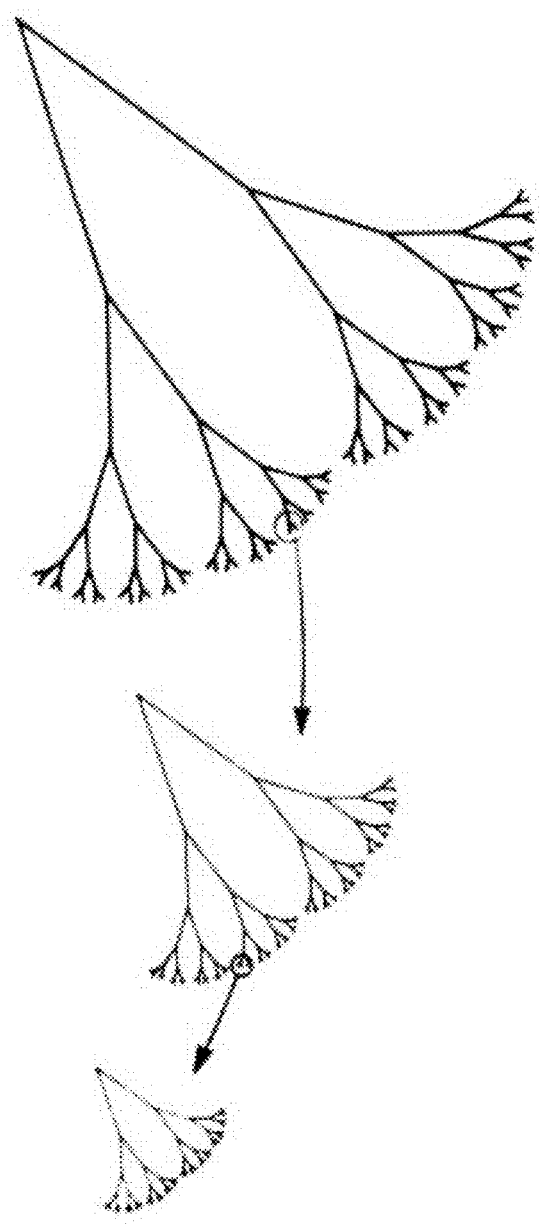
FIG. 7A shows an example of self-similarity in the spacial, temporal and frequency domains.
Figure 7A:
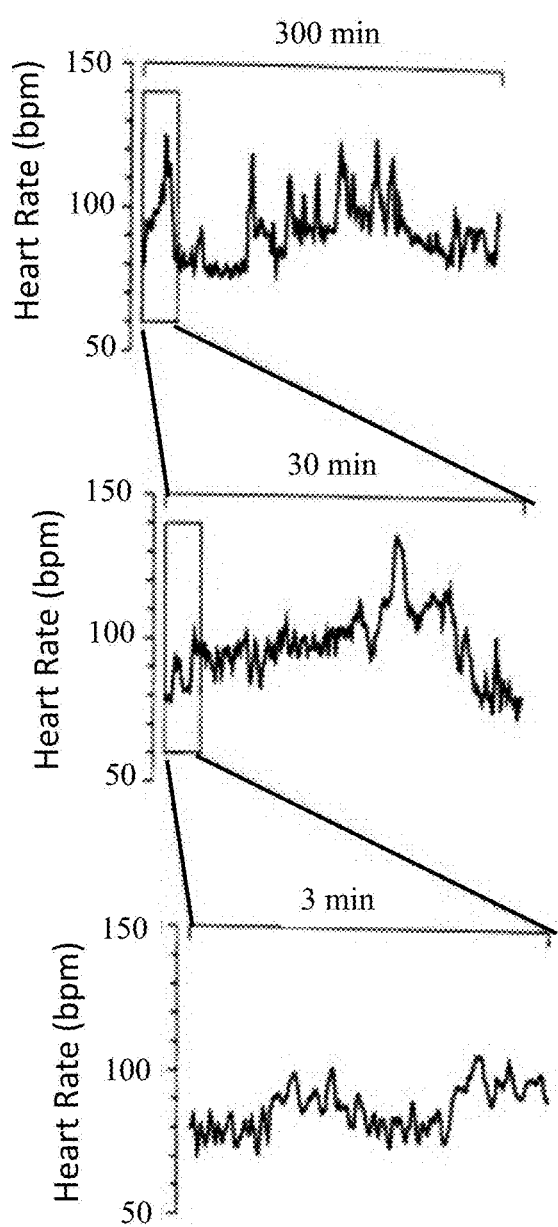

An interesting and important property of heart rate variability is that it exhibits non-linear fractal dynamics. The term 'fractal' is usually associated with the spacial and geometric self-similarity exhibited by various natural formations like coastlines, tree-branches and snow flakes. However, this concept can be readily extended to time-dependent processes. Instead of geometric self-similarity along spacial axes, a fractal temporal processes exhibits statistical self-similarity along it's time and value axes. Such a process therefore maintains its properties (in terms of probability distribution) when scaling or "zooming-in". FIG. 7A provides an example of self-similarity in the spacial, temporal and frequency domains. A tree like structure exhibiting spacial self-similarity is shown on the left, and a heart rate temporal process exhibiting statistical self-similarity is shown on the right.

Figure 7B:
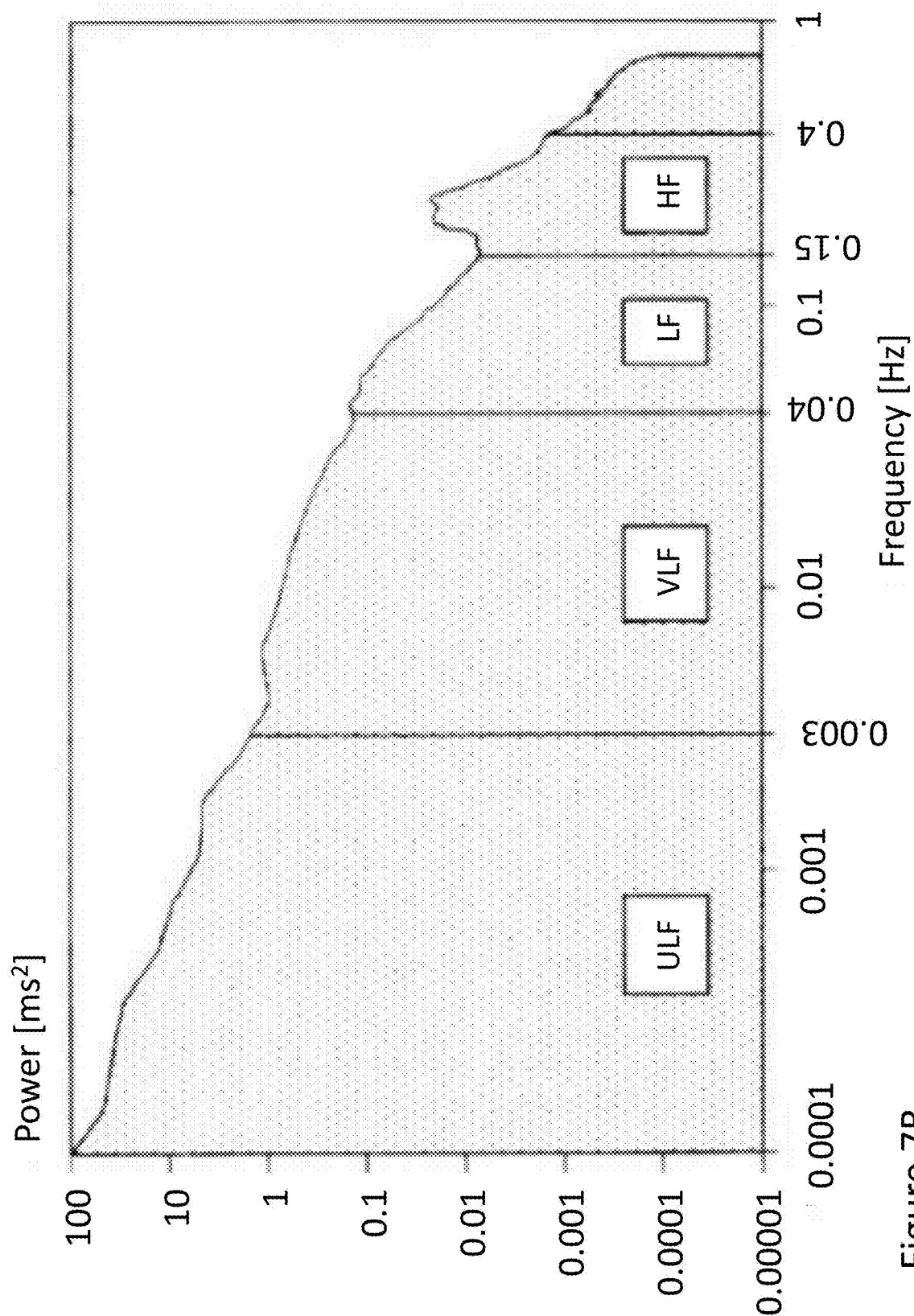
FIG. 7B illustrates spectral analysis of a 24-hour heart rate signal, plotted on a logarithmic scale.
Figure 8A:
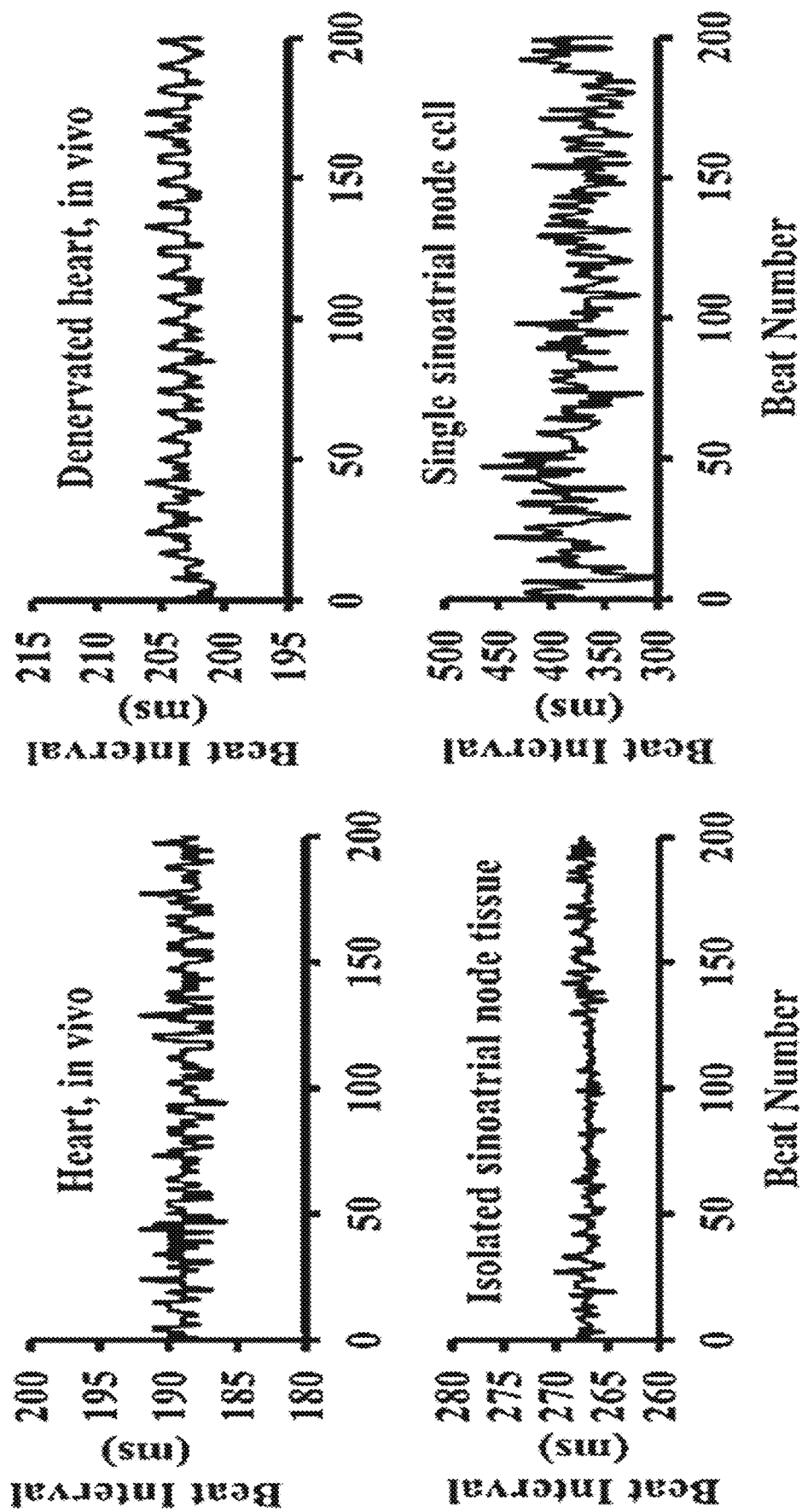
FIGS. 8A-B show beating intervals duration (8A) and distribution (8B) of rabbit SANC at different levels of integration, from a full beating heart to a single cell.
Figure 8B:
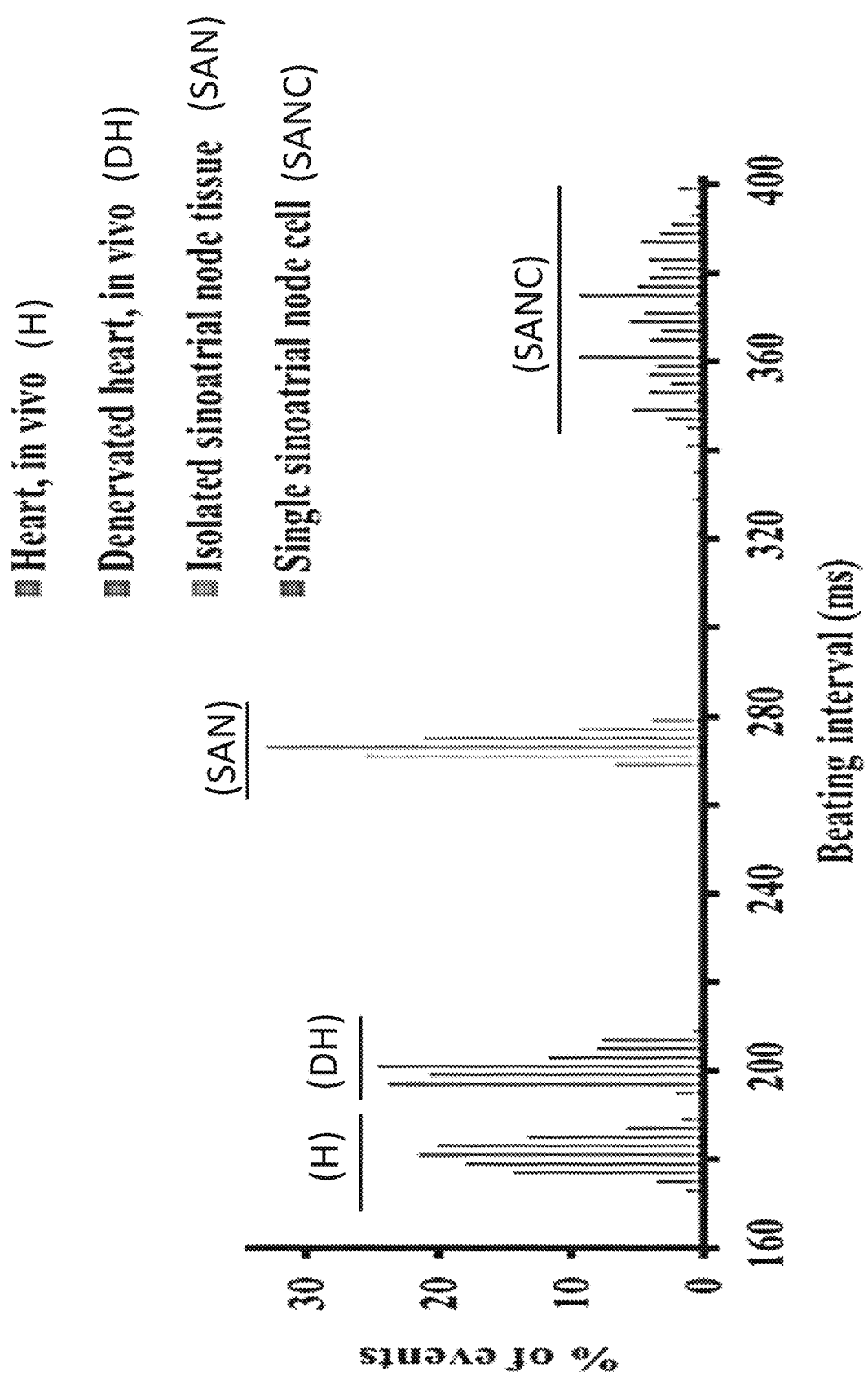

The self-similar, or fractal, nature of heart rate variability manifests in strong autocorrelations within the signal that decay slowly with time lag. In the frequency domain, the HRV of healthy individuals conforms to a power law-form; a broad-band spectrum with a long high-frequency "tail". When plotting the low-frequency range of the HRV spectrum on a log-log plot, an approximately linear relationship can be found between log-frequency and log-amplitude. This property is known as a power-law or $1/f$ distribution, as shown in FIG. 7B, which illustrates spectral analysis of a 24-hour heart rate signal, plotted on a logarithmic scale. In the Ultra- and Very-low frequency ranges (ULF and VLF), the spectrum is approximately linear, corresponding to a power-law distribution Computational Techniques and Experimental Results The following description details the computational techniques that may be used for evaluation of SAN and autonomic nervous system input function, and experimental results from canine models. Every technique used in the experiments described herein is part of the embodiments of the present invention.

1. Data Acquisition

The data sets used in the experiments were recorded in canines. We obtained two data sets: Sedentary (n=27 ECG records in the set) and Post-Exercise (n=20). The sedentary set contains data from healthy dogs that were not subjected to any exercise regimen, while the post-exercise data was recorded in dogs that were subjected to a 10- to 12-week exercise regimen prior to data collection. The exercise regimen only had an effect on the autonomic modulation of the heart, not on the SAN. This data set is therefore as HRV features of the SAN should not be subject to changes due to exercise.

2. ECG Segmentation

Figure 9A:
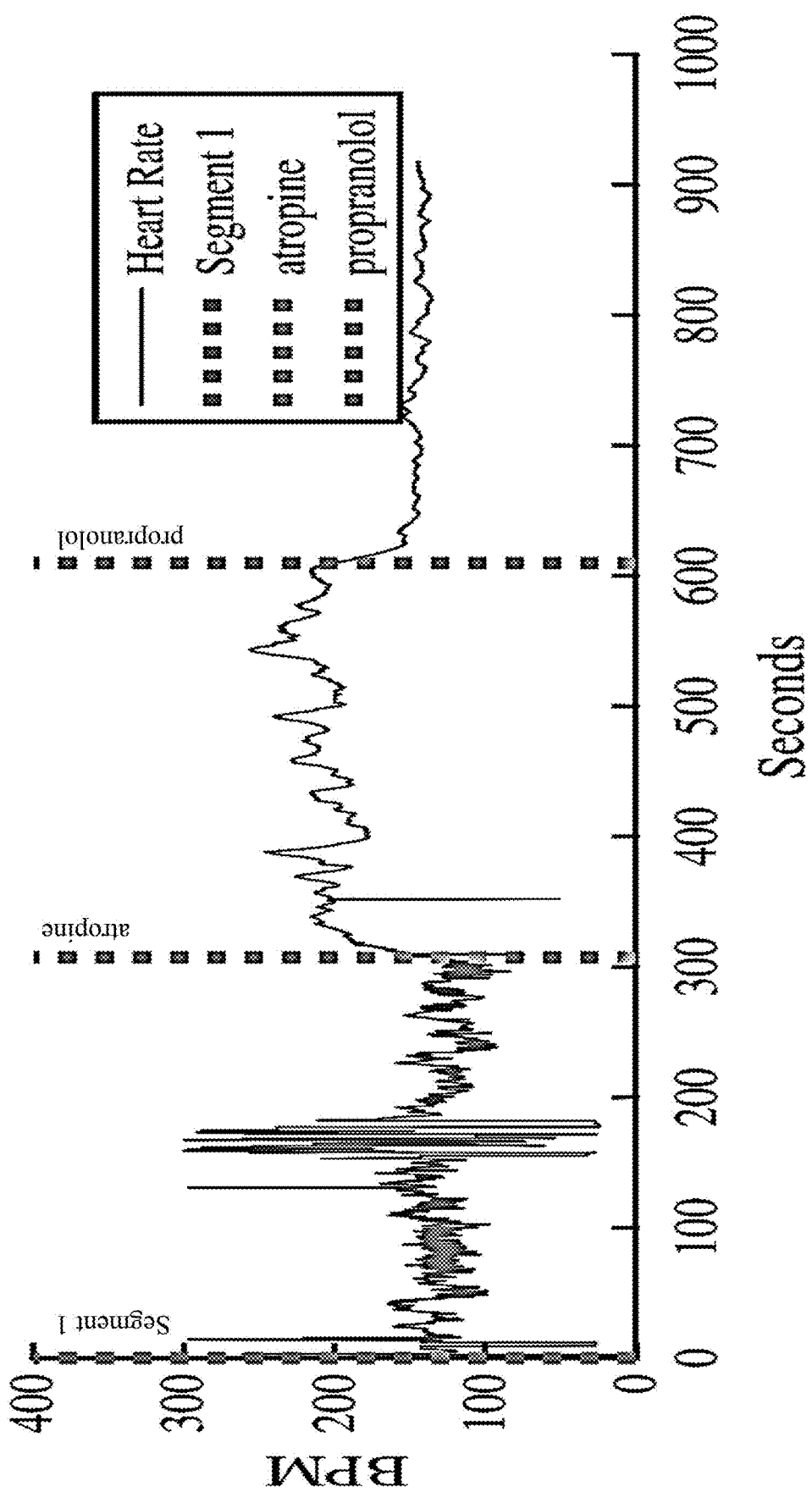
FIG. 9A for an example data record of canines, showing three segments.

The data records which we obtained each contained one continuous ECG and one continuous heart rate recording. Each record also contained manual annotations at the times in which a drug was administered, usually at least 5-minutes apart from each other. These annotations conceptually break the record up into multiple segments. In order to obtain data for this study, we needed to extract two ECG segments from each record: a basal segment (before any drugs were administered) and a double-blockade segment (after both atropine and propranolol were administered). By extracting the first segment from each record, then the third segment (after both drugs have been administered), we obtained a basal and double-blockade segment from each record. FIG. 9A depicts an example data record, showing three segments.

Figure 14:
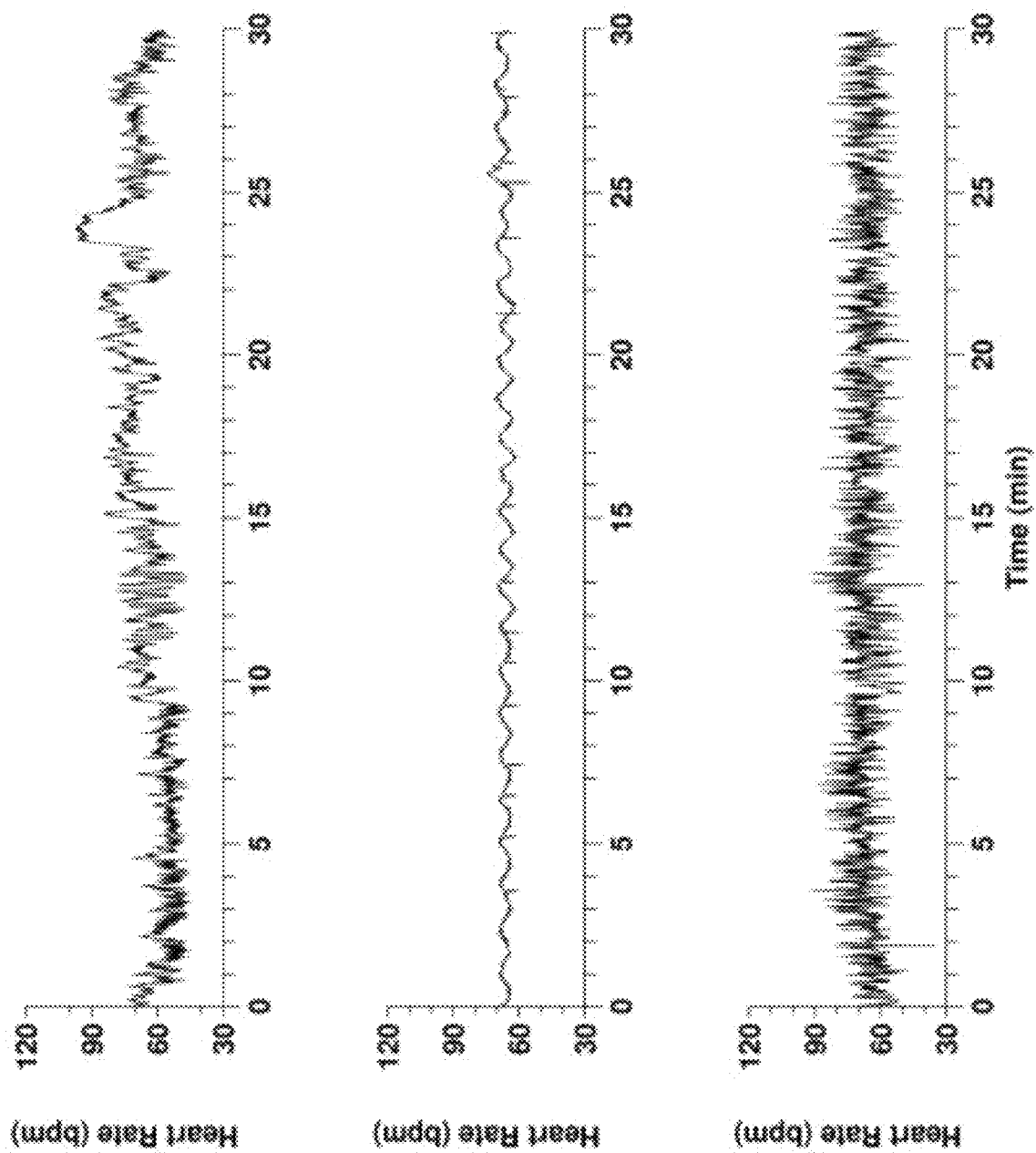
FIG. 14 shows examples of how pathology, through breakdown of fractal dynamic of the heart rate, can manifest as an either more or less complex interval time series.

FIG. 14 shows transient-removal for the denervated (last) segment. Showing the lowpass-filtered heart rate, the threshold value with it's 5% confidence intervals, and the final trimmed segment range.

Visual inspection of the records' data revealed that following each drug being administered, there was a short (up to 20-second) transient period until the HR reached a steady state again. These transient periods were removed from the segment before acquiring the segment's data.

Figure 9B:
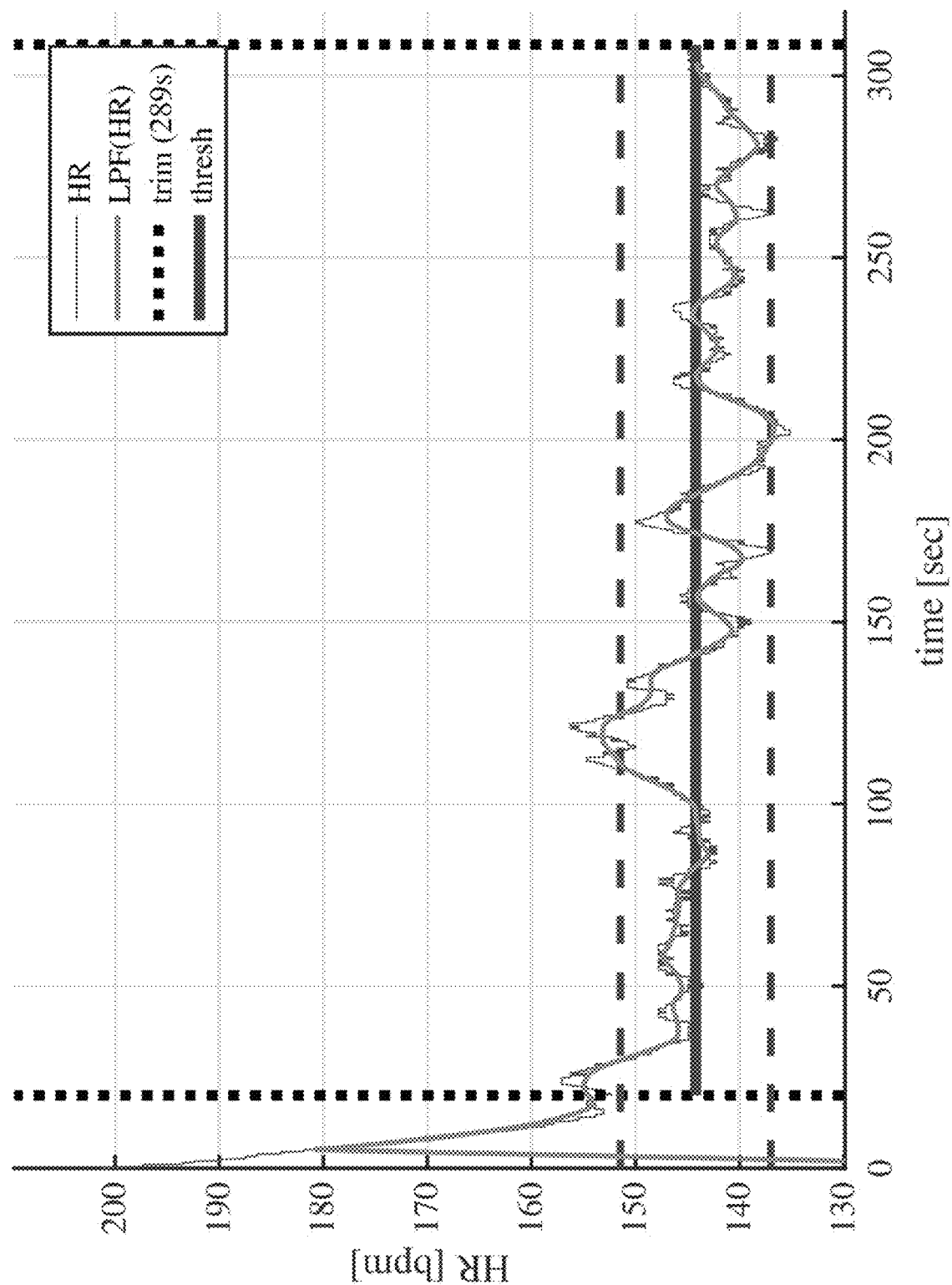
FIG. 9B visualizes a process of transients removal.

To remove the transient periods, the value of a 10-second sliding window lowpass filter was compared to a threshold taken as the mean value of the segment starting from 30 seconds after the start of the segment (this part of the segment was considered transient period-free). When the sliding window average was within 5% of the threshold, the transient period was considered over, and the rest of the segment was used. After transient period removal, each segment was trimmed at the end to standardize the duration of the segments to 5-minutes in cases that were longer. FIG. 9B visualizes this process. Only the HR channel is shown here, but the record also contains an ECG channel.

The segmentation process produced the four following groups of ECG records which were used in this study:
  Sedentary Basal (PreEx-BSL; n=27)
  Sedentary Denervated (PreEx-DBK; n=27)
  Post-Exercise Basal (PostEx-BSL; n=20)
  Post-Exercise Denervated (PostEx-DBK; n=20)

3. R-Peak Detection

In order to calculate heart-rate variability indexes from ECG signals, we must first identify the R-peaks of the QRS complexes that exist in the signal. The HRV can then be calculated from the beat-to-beat interval between each two peaks.

Various different algorithms for finding QRS complexes in ECG signals exist and their performance has been studied. The 'gqrs' detector, part of the PhysioNet WFDB toolkit, has been shown to be the best detector on several ECG waveform databases. In addition, it allows setting parameters to easily adapt it for non-human ECG. However, because the 'gqrs' algorithm actually detects the beginning of the entire QRS complex (and not the R-peaks), it's not ideal for HRV calculation, thus for beat-to-beat analysis the R-peak is arguably a more stable fiducial point than the QRS onset. Although beat-to-beat intervals can be calculated from the start of the QRS complex, the standard methods for calculation of the various existing HRV indexes rely on R-peak detection. In addition, using the intervals between QRS complexes may be less robust than using R-peaks since they are a much more pronounced feature in the signal. A custom detector, 'rqrs', was therefore created for this paper. The 'rqrs' detector is based on 'gqrs' but with an additional step: For each QRS complex detected by 'gqrs', it searches forwards in a small window from the start time of the detection. The maximal value in the window is then reported as an R-peak detection. The duration of the window was chosen to be about 80% of the average duration of one QRS complex (depending on species).

Figure 10:
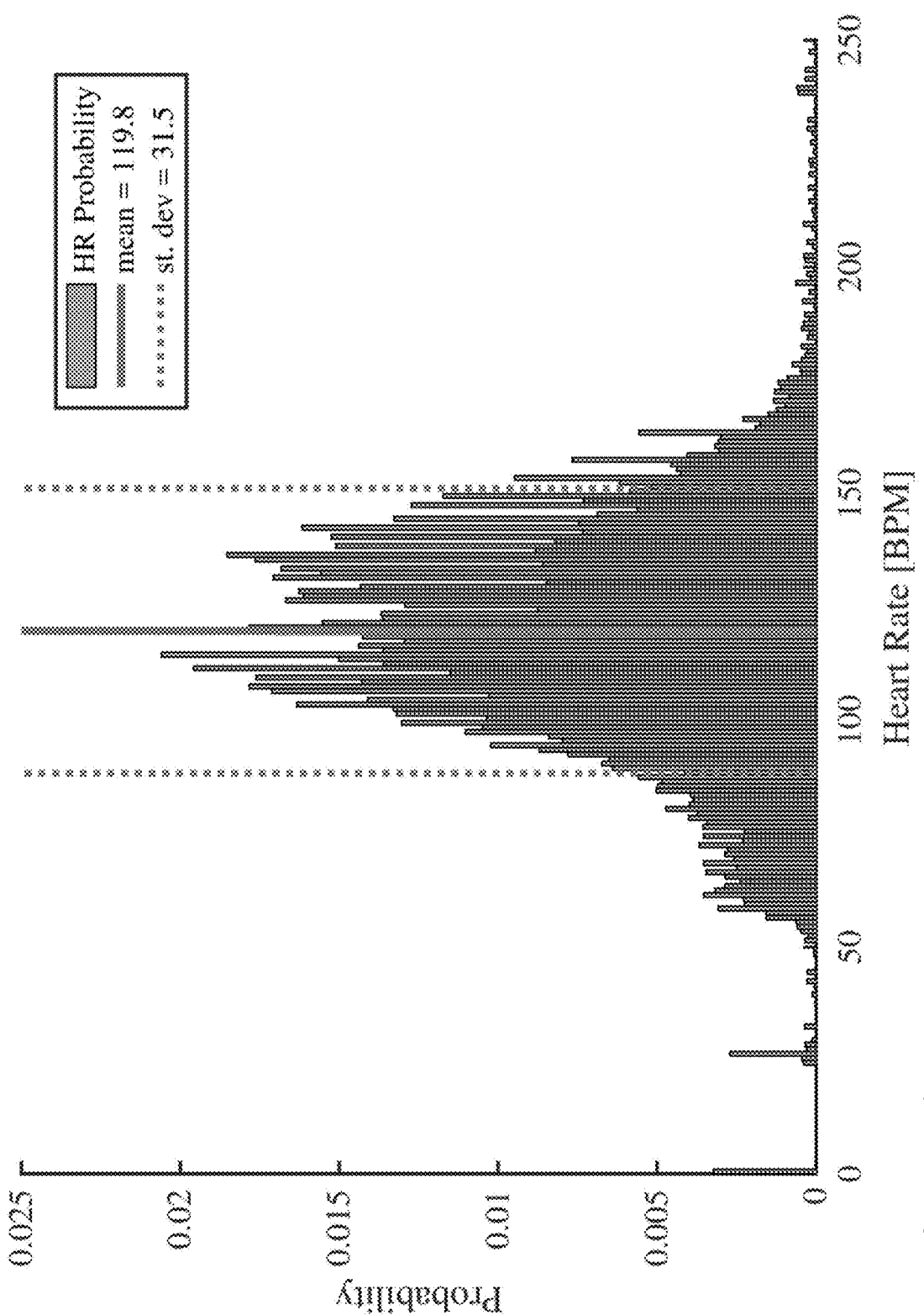
FIG. 10 shows the mean heart rate of the PreEx-BSL group.

In order to adapt the peak-detection algorithm to the canine data sets, some parameter modification was required. Table 1 lists the parameter values for the gqrs/rqrs algorithms that were used for peak detection on both human and canine ECGs. The mean heart rate of the PreEx-BSL group (shown in FIG. 10) was used as a baseline to configure the peak-detection algorithm.

TABLE 1

Peak detection parameters used to configure gqrs and rqrs for PhysioNet human data and the canine data used in this study. Other gqrs parameters, not specified here were left at their default value.

| Parameter | Description | Human | Canine | Units |
|---|---|---|---|---|
| HR | Mean heart-rate | 75 | 120 | [beats/min] |
| QS | Mean QRS duration | 0.07 | 0.05 | [sec] |
| QT | Typical QT interval duration | 0.35 | 0.16 | [sec] |

TABLE 1-continued

Peak detection parameters used to configure gqrs and rqrs for PhysioNet human data and the canine data used in this study. Other gqrs parameters, not specified here were left at their default value.

| | | Value | | |
|---|---|---|---|---|
| Parameter | Description | Human | Canine | Units |
| RRmin | Minimum RR interval duration | 0.28 | 0.3 | [sec] |
| RRmin | Maximum RR interval duration | 2.4 | 2.0 | [sec] |
| QRSa | Mean peak-to-peak amplitude | 750 | 1000000 | [µV] |
| QRSamin | Minimum peak-to-peak amplitude | 750 | 50000 | [µV] |
| winlen | rqrs forward-search window | 0.056 | 0.04 | [sec] |

To make sure 'rqrs' provides robust peak detections at least as accurate as 'gqrs', the algorithm was tested against the 2014 PhysioNet challenge updated training set. This set contains 200 ECG records, some of which are very challenging for detection algorithms due to noise and artifacts. This set was previously used to assess various detector algorithms, including 'gqrs', so it's performance is known on this set. All ECG records in the set are fully annotated (i.e. reference correct R-peak locations are provided) and the annotations were used to evaluate performance automatically.

To assess detection quality the following well-known statistical measures were used:

Sensitivity, Se. This is the fraction of events (R-peaks) that were detected.

$$Se = \frac{TP}{TP + FN}$$

Positive Predictive Value, PPV. This is the fraction of detections that were events (R-peaks).

$$PPV = \frac{TP}{TP + FP}$$

where,

TP (True positive): Number of detections that have a matching reference annotation.

FP (False positive): Number of detections that don't have a matching detection in the reference annotations (incorrect detections).

FN (False negative): Number of reference annotations that weren't matched with a detection (missed events).

As an overall detection quality measure, F1, was also used to allow comparison with previous works on this data set. The F1 measure is defined (in our case) as $$F1 = 2 \cdot \frac{PPV \cdot Se}{PPV + Se}.$$

This measure was proposed for comparing peak-detection algorithms due to it's ability to combine multiple fractional measures better than a simple average, by using a harmonic mean. In this case it's the harmonic mean of the sensitivity and positive-predictive value.

To assess a detector's performance, the detected beat locations were compared to the reference annotations for that record (which contain the real beat locations). The detection times were compared to the reference annotations using a 150 ms window around each detection (as standardized by ANSI/AAMI, 1998). For each detection, the closest reference annotation was found. If the closest annotation was within the aforementioned window around the detection, it was considered a correct detection, and the TP, FN and FP values were updated accordingly.

A comparison of the results of 'gqrs' and 'rqrs' on the PhysioNet 2014 challenge database can be seen in Table 2. For 'gqrs' we can see the expected results (almost identical to the results reported previously). The 'rqrs' algorithm performs similarly to 'gqrs', with a slightly better overall score, arguably due to the fact that it finds the R-peaks themselves, increasing the chance that a reference annotation will be within the comparison window around the detection.

TABLE 2

Performance comparison of gqrs and rqrs on the PhysioNet 2014 challenge database. The Gross values were calculated over all detections and annotations in the set, without averaging each record individually.

| | Mean | | Gross | | |
|---|---|---|---|---|---|
| | Se | PPV | Se | PPV | F1 |
| gqrs | 94.409 | 92.615 | 91.665 | 90.976 | 92.784 |
| rqrs | 93.809 | 93.624 | 93.845 | 93.026 | 93.434 |

In order to assess the performance of 'rqrs' on the canine data used in this study, the PreEx-BSL data set was manually annotated and the detector was compared to these annotations. The performance was assessed using the same method described for the human data, except that for the canine case a shorter window of length 90 ms was used around each detection when comparing with the annotations. This window size corresponds to roughly 60% of the standard window size defined for human data. It was chosen because the average heart rate in the PreEx-BSL set was observed to be about 120 BPM, roughly 60% higher than the average human heart rate of 75 BPM. The results are reported in Table 3. The almost-perfect detection performance on this set affirms that the detector parameters were properly configured for the canine data (see Table 1).

TABLE 3

Performance of the 'rqrs' detector on the manually-annotated PreEx-BSL set.

| | Mean | | Gross | | |
|---|---|---|---|---|---|
| | Se | PPV | Se | PPV | F1 |
| rqrs | 99.288 | 98.504 | 99.172 | 98.267 | 98.717 |

4. HRV Analysis Methods

Numerous methods exist to quantify heart rate variability by looking at the beat to beat intervals' length variations. The basic interval lengths can be obtained by measuring the time differences between R-peaks of the QRS complex in ECG recordings (RR intervals). However, by definition only beats resulting from normal SAN (i.e., not arrhythmic, paced, ventricular, etc.) should be used for HRV metric calculations. The intervals between such normal beats are referred to as NN intervals.

One particular type of beats we would like to reject are out-of-place premature beats knows as ectopic beats. These are quite common in ECG signals and in many cases originate from the AVN or pacemakers in the ventricles due to a blockage of the depolarization signal from the SAN. The rejection of ectopic beats is therefore important in order to isolate the contribution of the SAN to the HRV. In addition to ectopic beats, ECG signals generally contain various artifacts caused e.g. by movement of the subject or by the recording equipment. Such artifacts should ideally also be removed prior to any HRV analysis.

Generally, in order to obtain NN intervals, RR intervals are found using an ECG peak-detection algorithm and then a preprocessing step (either manual or automatic) is performed to filter out suspected ectopic beats and artifacts. In this case, we applied 'rqrs' for peak detection and an automatic preprocessing step to reduce the likelihood of ectopic beats.

It should be noted that ECG and HRV analysis methods, as described in the literature and respective studies, are usually designed for use with human ECG data. Because we obtained canine data, an attempt was made, where it was deemed relevant, to adapt each specific algorithm or data-analysis method used to a canine model. These adaptations are described for each method in the following sections.

4.1 RR Interval Preprocessing

An RR interval is the time difference between two adjacent R-peaks in an ECG signal. More specifically, given a series of N R-peak detection times $t_0, \ldots, t_{N-1}$, the corresponding RR interval time series is defined as $$RR(t_i) = t_{i+1} - t_i, \ i = 0, 1, \ldots, N-2 \quad (3)$$

Note that the RR interval series is defined at the R-peak detection times only, and each interval at a specific peak time is the time from that peak to the next.

We would like to find the subset of these intervals for which both beats comprising the interval are normal sinus beats. Since there is no way to know with absolute certainty whether an ECG peak originated in the SAN, it will suffice to at least greatly reduce the likelihood of having non-NN intervals in the preprocessed data. One way to do this is to improve the ECG peak-detector so that it detects less non-SAN peaks in the first place. Another approach is to analyze the RR-interval time series and discard intervals that are suspect based on some criteria. Arguably, looking at the intervals time-series provides more information based on which to decide whether it's likely an NN interval, because peak locations relative their adjacent peaks change considerably between NN and ectopic beats, typically by more than 20%.

As discussed in section 3 above, our peak detector is based on 'gqrs'. Its main limitation is that it can only shift detections in time; it doesn't add new detections or discard existing ones. Because 'gqrs' was shown to be a robust and well-performing algorithm, we decided against attempting to improve it further, and instead focused on the second approach of attempting to analyze the RR intervals to remove intervals suspected with not being NN. Multiple distinct preprocessing steps were implemented to remove suspected intervals.

Step 1: Range-based filtering. RR interval duration inversely relates to the instantaneous heart rate:

$$IHR(t) = \frac{60}{RR(t)}, \quad (4)$$

where RR(t) is an RR interval, in seconds, measured at time t and IHR(t) is the instantaneous heart rate in BPM at time t. This means that there are upper and lower bounds on the RR intervals that can be obtained from the physiological limits of the heart rate. For example, if we assume the instantaneous heart rate will be in the range of 40-187.5 BPM then the range of RR interval values must be 0.32-1.5 seconds and thus intervals not within this range can be discarded as non-NN. For our canine data sets, we rejected RR intervals outside the range of 0.3-1.2 seconds, which corresponds to a heart rate outside the range 50-200 BPM.

Step 2: Sliding-window averaging filter. In some cases the RR interval time series can contain intervals that are very short or very long when compared to their neighboring intervals, which can look like pronounced "spikes" when plotting the RR intervals. While beat-to-beat variability is what we're looking for, these spikes indicate a large change in RR interval duration between adjacent intervals or relative to neighboring interval values. This could, in turn, indicate that at least one of the beats in the interval was ectopic or perhaps even a false detection. To remove such intervals, a sliding-window filter is passed over the RR intervals time series. The average in the window is calculated without the sample in the center of the window. If the central sample's value exceeds (in absolute terms) the window average by some percentage, that sample is removed. We decided to use a window size of 21 samples (10 sample on each side of the central sample) and filtered out the sample if it's value exceeded 20% of the window's average. The threshold and window size were chosen to be identical to the values used by the PhysioNet HRV toolkit.

Step 3: Quotient filter. This filter removes intervals that vary by more than some percentage q from either the next of previous interval. It's similar in concept to the sliding window average filter, however it's much more local. For each interval, the filter looks at the ratio between it and the previous and next intervals. If this ratio exceeds a q percent change, the interval is discarded. More specifically, we'll define r=q/100 (so 0<r<1). The filter rejects the interval at time $t_i$, $RR(t_i)$, if any of the following conditions are true:

$$\frac{RR(t_i)}{RR(t_{i+1})} < 1 - r, \text{ or } \frac{RR(t_i)}{RR(t_{i+1})} > 1 + r \quad (5)$$

$$\frac{RR(t_{i+1})}{RR(t_i)} < 1 - r, \text{ or } \frac{RR(t_{i+1})}{RR(t_i)} > 1 + r \quad (6)$$

For human data, a value of q=20% was shown to work well for removing non-physiological intervals in data from heart-failure patient data. This filter is useful for removing strong local noise (very short or long intervals) due to it's aggressiveness. For our canine data, we used a value of q=80, which in practice removes very little intervals. The ones that are removed however were clearly anomalous; Upon visual inspection of the original ECG signal, such intervals were caused by either missed R-peaks (causing a very long interval) or by noise artifacts being detected as R-peaks (causing very short intervals).

Figure 11A:
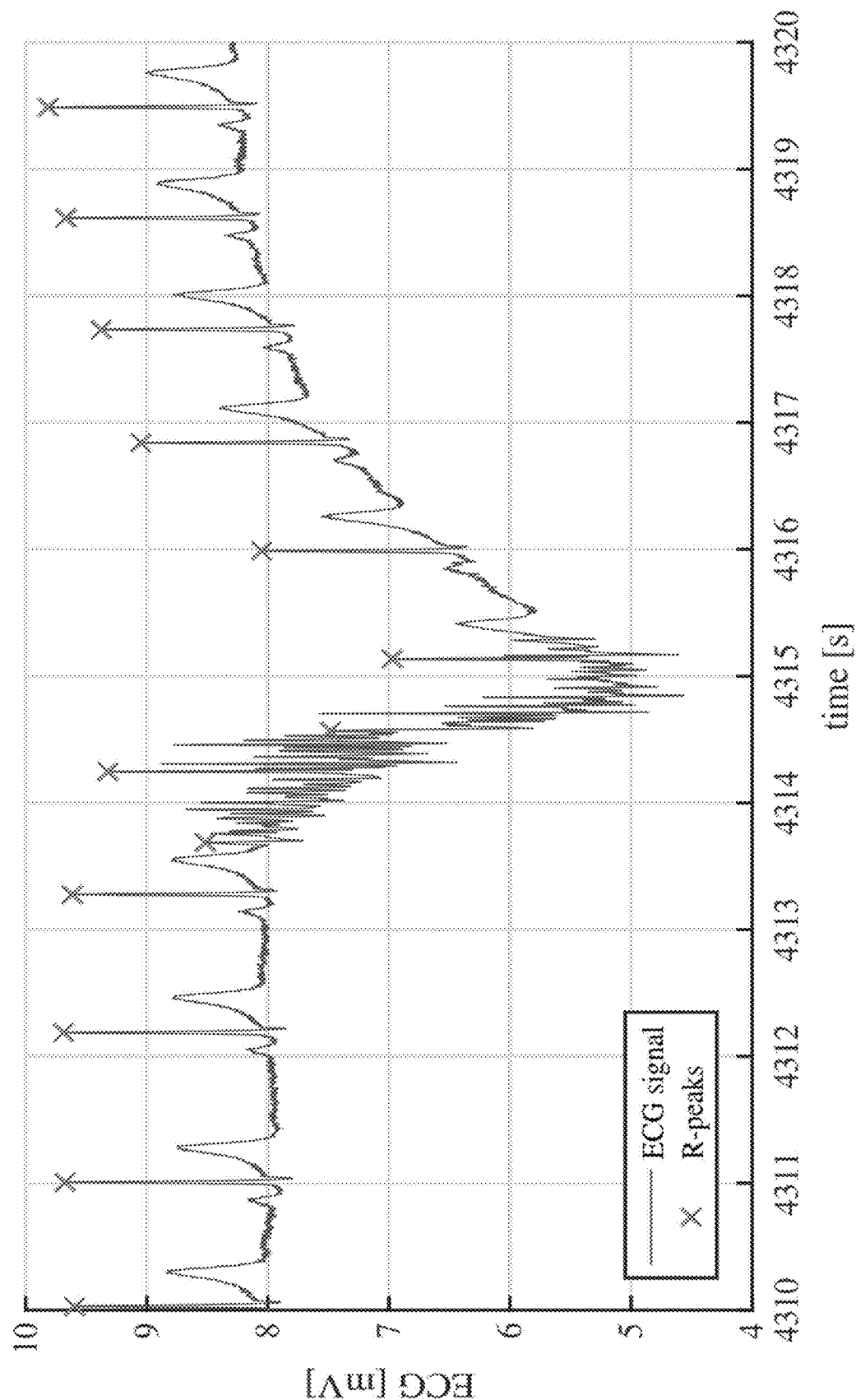
FIG. 11A is a short ECG segment showing R-peaks.
Figure 11B:
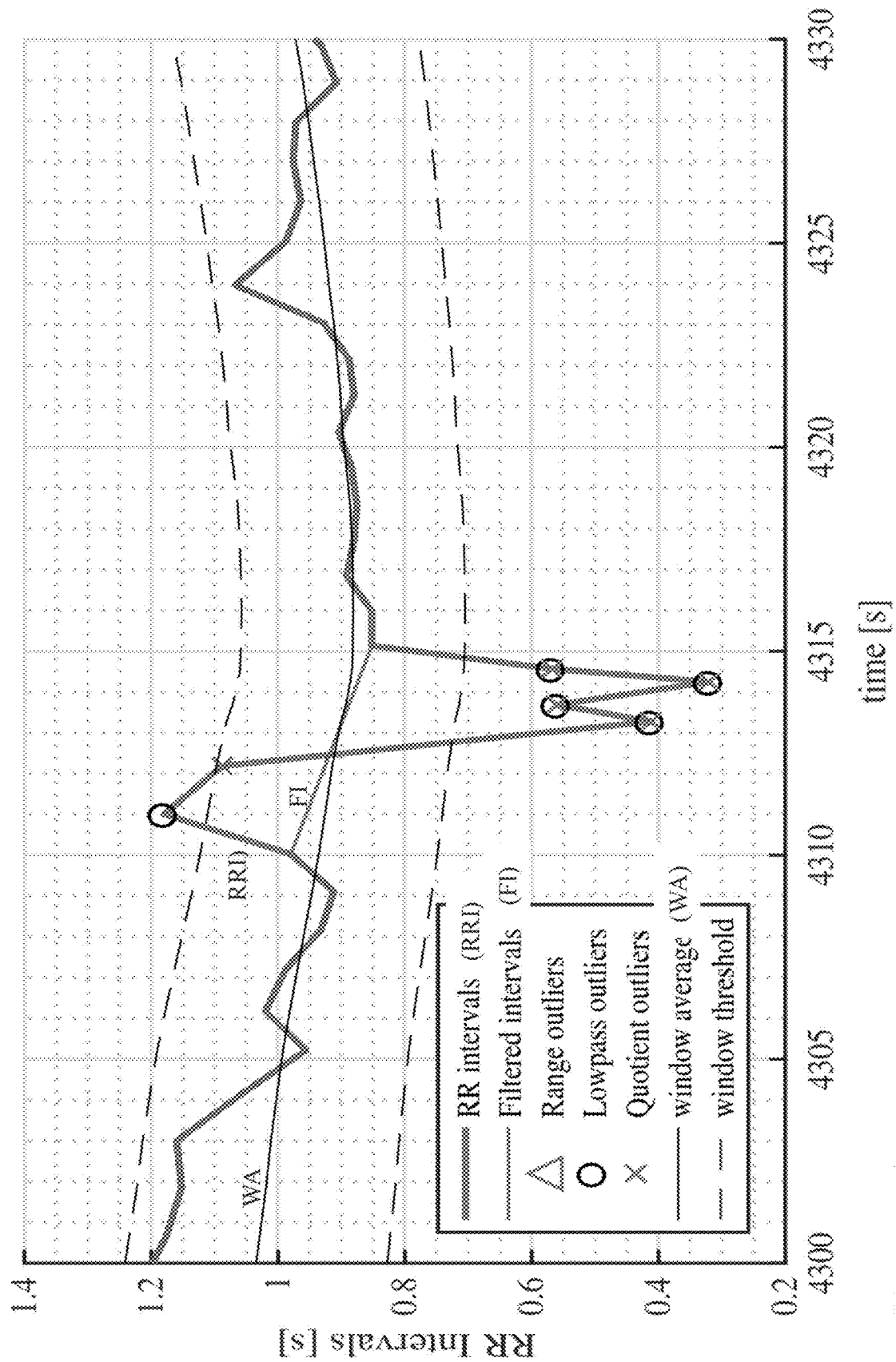
FIG. 11B shows RR intervals time series before and after filtering, showing the intervals that were flagged for removal and by which filter.

FIGS. 11A and 11B show a short segment of ECG that contains a noisy region, the corresponding RR interval time series in that segment with suspected non-NN intervals, and the resulting filtered intervals. The ECG signal used was fantasia/fly06 from the PhysioNet Fantasia database. FIG. 11A is a short ECG segment showing R-peaks. Visual inspection shows that there is a relatively long interval starting at 4311 sec, and a noisy region in 4313-4316 sec.

FIG. 11B shows RR intervals time series before and after filtering, showing the intervals that were flagged for removal and by which filter. We can see a series of four very short intervals starting at 4313 sec, which correspond to the noisy region. In addition, we can see the quotient filter rejection of the interval at 4312, due to the large change relative to the next interval. Also, we can see the sliding window filter rejection of the interval at 4311 due to it being more than 20% longer than the average in its neighborhood.

4.2 Time Domain Metrics

The most straightforward HRV analysis methods rely on linear time-domain statistics. For i=0, ..., N−1, we'll denote $t_i$ as the beat times and $NN(t_i)$ as the NN-interval beginning at time $t_i$. The following well-known metrics were used.

SDNN: The standard deviation of all NN intervals.

$$SDNN = \sqrt{\frac{1}{N-1}\sum_{i=0}^{N-1}(NN(t_i) - \overline{NN})^2}, \quad (7)$$

where $\overline{NN}$ is the mean NN interval time.

RMSSD: Root mean square of successive differences (SD) of NN intervals.

$$RMSSD = \sqrt{\frac{1}{N-1}\sum_{i=1}^{N-1}(NN(t_i) - NN(t_{i-1}))^2}. \quad (8)$$

pNN50: The percentage of NN intervals which differ by at least 50 ms from their preceding interval:

$$pNN50 = \frac{1}{N-1}\sum_{i=1}^{N-1} I_i^{50}, \quad (9)$$

where $I_i^{50}$ is the indicator $$I_i^{50} = \begin{cases} 1, & |NN(t_i) - NN(t_{i-1})| > 50 \text{ [ms]} \\ 0, & \text{else} \end{cases}.$$

Adaptation for Canine Data

The SDNN and RMSSD metrics require no modification for use with canine ECG data, because they're purely statistical. In contrast, the pNN50 measure uses a fixed criteria for variability, based on a threshold that was found to work well for human ECG data (50 ms). However, this measure is not suitable for measuring HRV in canine data due to the higher average heart rate present in dogs. A higher average heart rate translates to shorter RR-intervals, so a low pNN50 can be expected even for a canine signal with relatively high HRV. To adapt the pNN50 measure, we'll generalize it to pNNα where α is a species-dependent threshold difference between two adjacent NN intervals (so for humans, $α_H$=50 [ms]). We'll start by looking at the ratio of $α_H$ to the average NN interval length in humans. Given an average heart rate $\overline{R}$ [BPM], we can say that the average NN-interval length, in seconds, is $$NN = 1 \Big/ \frac{R\left[\frac{\text{Beats}}{\text{min}}\right]}{60\left[\frac{\text{sec}}{\text{min}}\right]} = \frac{60}{\overline{R}} \text{ [sec]} \quad (10)$$

which is the inverse of the number of beats per second. Therefore, assuming an average heart rate of $\overline{R}_H$=75 [BPM], the human average NN interval length is $$\overline{NN}_H = \frac{60}{\overline{R}_H} = \frac{60}{75} = 0.8 \text{ [sec]}, \quad (11)$$

and for our canine data we have $\overline{R}_C$=120 [BPM], therefore $\overline{NN}_C$=0.5 [sec]. Now, the ratio of the threshold interval difference (α) to the average NN interval length is $$\frac{α_H}{\overline{NN}_H} = \frac{50 \text{ [ms]}}{0.8 \text{ [sec]}} = 0.0625. \quad (12)$$

Finally, to find a comparable threshold difference for the canine data, we'll require the same ratio to hold:

$$\frac{α_C}{\overline{NN}_C} = 0.0625 \Rightarrow α_C = 31.25 \text{[ms]}. \quad (13)$$

4.3 Poincaré Plots

Poincaré plots are a method of visualizing the relationship between consecutive intervals, in which $RR_{n+1}$ is scatter-plotted as a function of $RR_n$. This makes it a state-space representation of the RR interval signal showing all states (combinations of values) of consecutive intervals that occurred. Usually a Poincaré plot of an RR-interval signal presents as a point-cloud around the line of identity. The most common metrics used to analyze Poincaré plots are SD1, the standard deviation of points along the line perpendicular to the line of identity (LOI) and SD2, which is the standard deviation of points along the LOI. Visually, SD1 is a measure of the width of the point cloud while SD2 is a measure of it's length. Using these measures an ellipse is usually fitted to the points, allowing for visual qualitative inspection and also for ectopic beat detection (intervals outside the ellipse are suspected as ectopic). It has been previously shown that SD1 and SD2 are measure of short- and long-term variability in the RR intervals (respectively), and also that the shape of the plot is related to the spectral power in the low and high frequency ranges.

Figure 12:
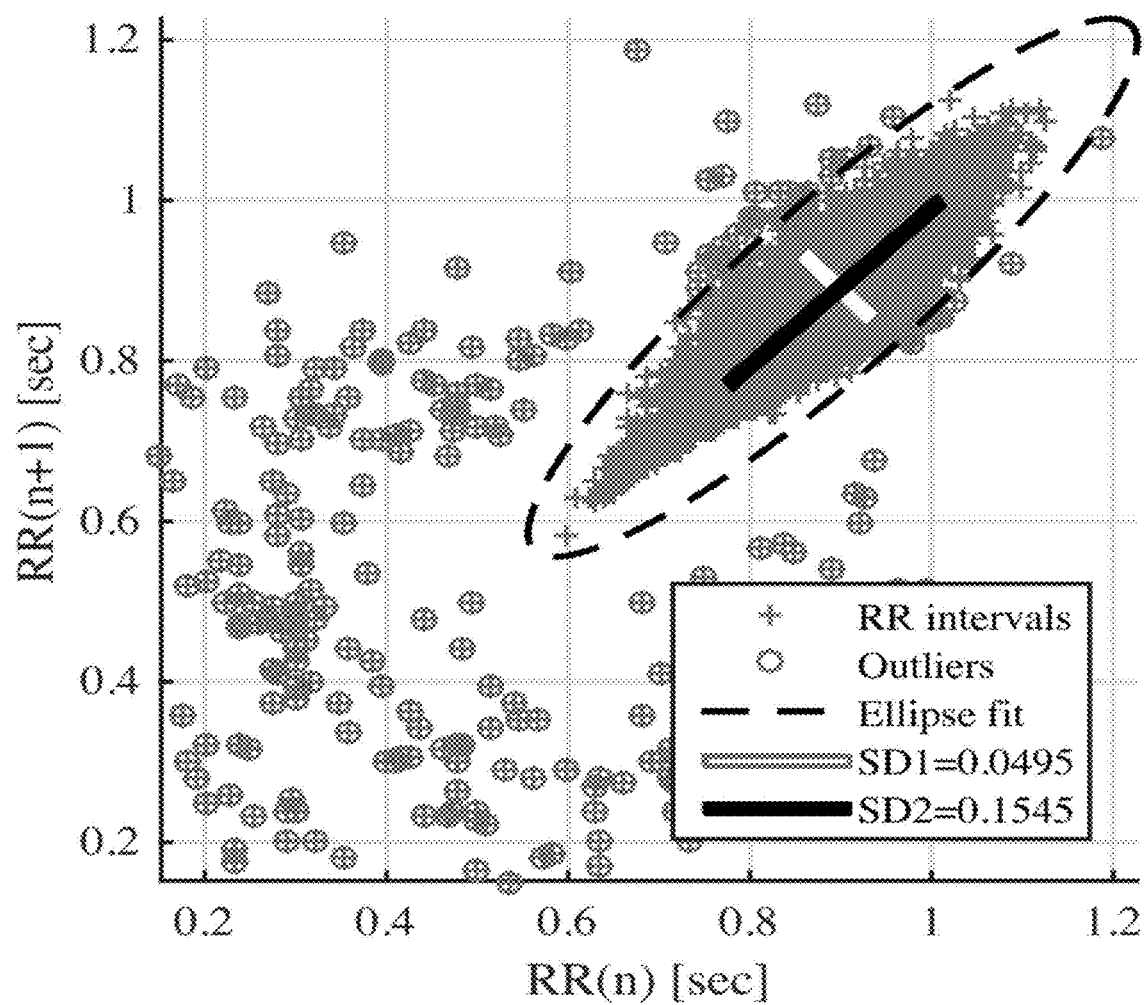
FIG. 12 is a Poincaré plot showing a visual representation of the standard metrics SD1 and SD2.

FIG. 12 is a Poincaré plot showing a visual representation of the standard metrics SD1 and SD2. In addition, an ellipse was fitted to two standard deviations using these metrics, in order to show intervals suspected as being ectopic.

4.4 Frequency Domain Metrics

Another HRV analysis approach is to visualize the NN intervals in the frequency domain. This allows us to estimate the frequency content of the NN intervals, i.e. the contribution of each frequency component to the signal's power. To do this, we need to estimate the power spectral density of the NN intervals time series $$\{t_i, NN(t_i)\}_{i=0}^{N-1} \quad (14)$$

which is essentially a finite realization of a random process. Various methods exist for spectral estimation of random processes, methods which can be broadly categorized as parametric and non-parametric. Parametric methods rely on a predetermined model of the process producing the samples, usually an autoregressive moving average (ARMA) model. The model parameters are estimated from the sampled data, and then the spectrum can be calculated with arbitrary precision based on the model. Non-parametric methods compute the spectrum directly usually using Fourier-based analysis of the data itself and are more severely limited by the quantity and quality of the data.

A major non-parametric spectral analysis technique is to use a periodogram to estimate the spectrum of a random process. The periodogram $\hat{S}_X[k]$ of a time-series x[n] of length N sampled at $f_s$ Hz is defined as the squared magnitude of the Discrete Fourier Transform (DFT) of the signal:

$$\hat{S}_X[k] = \frac{1}{N}|X[k]|^2 = \frac{1}{N}\left|\sum_{n=0}^{N-1} x[n]e^{-j2\pi kn/N}\right|^2 \quad (15)$$

where k is a discrete frequency index such that the corresponding physical frequency in Hz is $$f(k) = k \cdot \frac{f_s}{N}, k = 0, 1 \ldots, \frac{N}{2} - 1. \quad (16)$$

We're only considering N/2 values of k because we're dealing with real-valued input signals. The periodogram, while simple, is not a consistent estimator for the PSD—it does not converge to the actual PSD as the number of samples increases. In addition it suffers from spectral leakage due to rectangular windowing in the time domain, which is equivalent to a frequency domain convolution with a sinc function. A more robust version of the periodogram, which suffers less from these drawbacks is the Welch periodogram, defined as:

$$\hat{S}_X[k] = \frac{1}{L}\sum_{l=0}^{L-1}\left\{\frac{1}{N}\left|\sum_{n=0}^{N-1} w[n]x[n+0.5lN]e^{-j2\pi kn/N}\right|^2\right\} \quad (17)$$

To calculate Welch's periodogram the input signal is split into L overlapping segments, each of length N. Each segment is multiplied by a window function w[n] and it's DFT is calculated. The DFT of all segments is then averaged. Note that the 0.5lN term creates a 50% overlap between segments. Welch's method sacrifices spectral resolution for smoothness obtained by averaging multiple shorter DFTs and reduces spectral leakage by using a non-rectangular window function.

Parametric spectral estimates are based on modeling of random processes. The idea is to assume the signal is the output of a causal and stable linear digital filter B(z) driven by a white noise input process v[n] with variance $\sigma_v^2$. The random process can then be represented by the filter parameters and the variance of the white noise. The most commonly-used parametric model is the autoregressive (AR) model, because it allows for relatively simple calculation of model parameters based directly on the sample autocorrelations of the data sequence itself (Yule-Walker method). AR models have been commonly employed for spectral estimation of RR interval time series. An AR model assumes the signal is a linear combination of p of it's previous values, i.e. it is of the form.

$$x[n]=v[n]-a_1x[n-1]-a_2x[n-2]-\ldots a_px[n-p] \quad (18)$$

which is the difference equation corresponding to an all-pole digital filter of order p with a transfer function $$B(z) = \frac{1}{1+a_1z^{-1}+a_2z^{-2}+\ldots+a_pz^{-p}}. \quad (19)$$

For such a filter, the PSD can be computed directly from the transfer function:

$$S_X(\omega)=\sigma_v^2|B(z=e^{j\omega})|^2 \quad (20)$$

This allows analytical calculation of the PSD at any precision.

An important assumption of spectral estimation techniques for random processes is the stationarity of the process. This means that the statistical properties of the signal (mean, variance and higher-order moments) should be time-invariant. In practice it's satisfactory to consider wide-sense stationary signals where only the mean and variance are constant with time. This follows from the Wiener-Kinchine theorem which states that wide-sense stationarity is a sufficient requirement for computing the power-spectral density $S_X(f)$ of a stochastic process x(t) from the Fourier-transform of it's autocorrelation $R_X(\tau)$:

$$S_X(f)=\int_{-\infty}^{\infty} R_X(\tau)e^{-j2\pi f\tau}d\tau \quad (21)$$

The use of 5-minute data segments recorded at rest has therefore become the standard for HRV analysis in the frequency domain because it is assumed that the statistical properties of the interval time series are sufficiently stationary in these short segments. However, longer or shorter recordings are also within the scope of present embodiments. For example, recordings having a length of 1-2 minutes, 2-3 minutes, 3-4 minutes, 4-5 minutes, 5-6 minutes, 6-7 minutes, 7-8 minutes, 8-9 minutes, 9-10 minutes, or more, may be used.

In addition to the stationarity assumption, most spectral estimation techniques assume a uniformly sampled time series input. In our case, the NN interval series is by definition not sampled uniformly. To obtain a non-parametric spectrum estimation of the NN interval time series without the need for resampling, the Lomb-Scargle periodogram has been previously used. This method is well-known, and is derived by solving a Least-Squares optimization problem of fitting an series of sinusoids the given data. The Lomb-Scargle periodogram was shown to provide favorable results on NN interval data. For other spectral estimation techniques, resampling to a constant sampling frequency is required. Cubic spline interpolation was previously shown to work well for resampling NN interval data.

Spectral analysis of the NN intervals reveals that periodic components are present in the interval series at frequencies below the heart rate. In healthy individuals, the frequency content of the interval lengths in a 5-minute recording is typically analyzed in three main frequency bands (ranges):

The high frequency (HF) band, 0.15 to 0.4 Hz. Characteristically, a HF peak can be found in this band around 0.25-0.3 Hz. The power in the HF band is attributed to vagal (parasympathetic) stimulation of the heart and the HF peak has been shown to correspond to the parasympathetic modulation at a frequency synchronous with the breathing rate, a phenomenon known as respiratory sinus arrhythmia (RSA).

The low frequency (LF) band, 0.04 to 0.15 Hz. A characteristic peak can usually be found at 0.1 Hz. Widespread consensus has yet to be reached regarding the physiological correlate for the power in this band. While some authors argue that this band is mainly influenced by sympathetic stimulation of the heart, this has been frequently challenged. Another physiological interpretation for this band is that it reflects the baroreceptor reflex frequency response.

The very-low frequency (VLF) band, 0.0033 to 0.04 Hz. Although this band accounts for most of the spectral power, it has yet to be fully understood and is usually ignored when citing HRV measures, even though loss of VLF power has been associated with many causes of mortality, more so than LF and HF power loss. While some researchers speculated that this band is related to parahormonal factors like thermoregulation and the renin-angiotensin system, newer works studying afferent neurons in the heart have shown evidence that the VLF power is in fact an intrinsic property of the heart itself.

The actual frequency-based metrics used to measure HRV are the absolute power present in the spectrum in each of the aforementioned frequency bands (measured in $ms^2$), the ratio of each of these to the total power in the entire range and the ratio of LF/HF power.

It should be noted that as with any type of frequency analysis, certain factors limit our ability to correctly and accurately estimate the power spectrum in the frequency range of interest. The first is the sampling frequency of the time series, which limits the maximal frequency we can correctly resolve. According to the Nyquist-Shannon sampling theorem, a sampling frequency of $f_s$ Hz would allow us to correctly measure the power in frequencies no higher than $f_s/2$ Hz. This frequency is known as the Nyquist rate and sampling at a lower rate would produce distortions in the higher frequencies, a phenomenon known as aliasing. In the case of an RR interval time series we have an irregularly sampled signal. We could either resample it at a frequency that would allow us to (at a minimum) resolve the end of the HF band or we could use the Lomb method instead. In the latter case the effective sampling interval is an average which depends on the total number of beats (For every N beats there are N−1 intervals) N in the recording:

$$\Delta t_{avg} = \frac{T}{N-1} \quad (22)$$

where T is the duration of the recording. By applying the sampling theorem we can see that the number of beats in the recording determines the maximal resolvable frequency:

$$f_{max} = \frac{\Delta f_{avg}}{2} = \frac{1}{2\Delta t_{avg}} = \frac{N-1}{2T}. \quad (23)$$

Usually we know the maximal frequency of interest and the duration of each segment in advance. Therefore we can impose a lower bound on N:

$$N_{min} = 2Tf_{max} + 1 \quad (24)$$

Consequently, while the Lomb method eliminates the need for resampling and thus prevents the artifacts associated with it, the risk of aliasing is higher with this method because the maximal frequency we can resolve without aliasing greatly depends on the average heart rate in the recording. Extra care must therefore be taken to make sure the Nyquist criterion is met in each analyzed segment.

Another factor affecting the accuracy of spectral estimation is the frequency resolution, which affects the minimal frequency we can resolve. From equation 16 we can see that in the case of a DFT, the frequency resolution $\Delta f$ would be $$\Delta f = \frac{f_s}{N} = \frac{1}{NT_s} = \frac{1}{T}. \quad (25)$$

Thus, the minimum resolvable frequency is inversely proportional to the total duration of the data segment being analyzed. A parametric spectrum estimate can provide better frequency resolution for short segments as it's not directly dependent on the data segment length. However, for parametric methods, the model order p will need to increase with the sampling frequency in order to resolve low frequencies. This has been studied, but can also be intuitively understood since as the sampling frequency increases, the same number of samples p correspond to a shorter duration.

Figure 13:
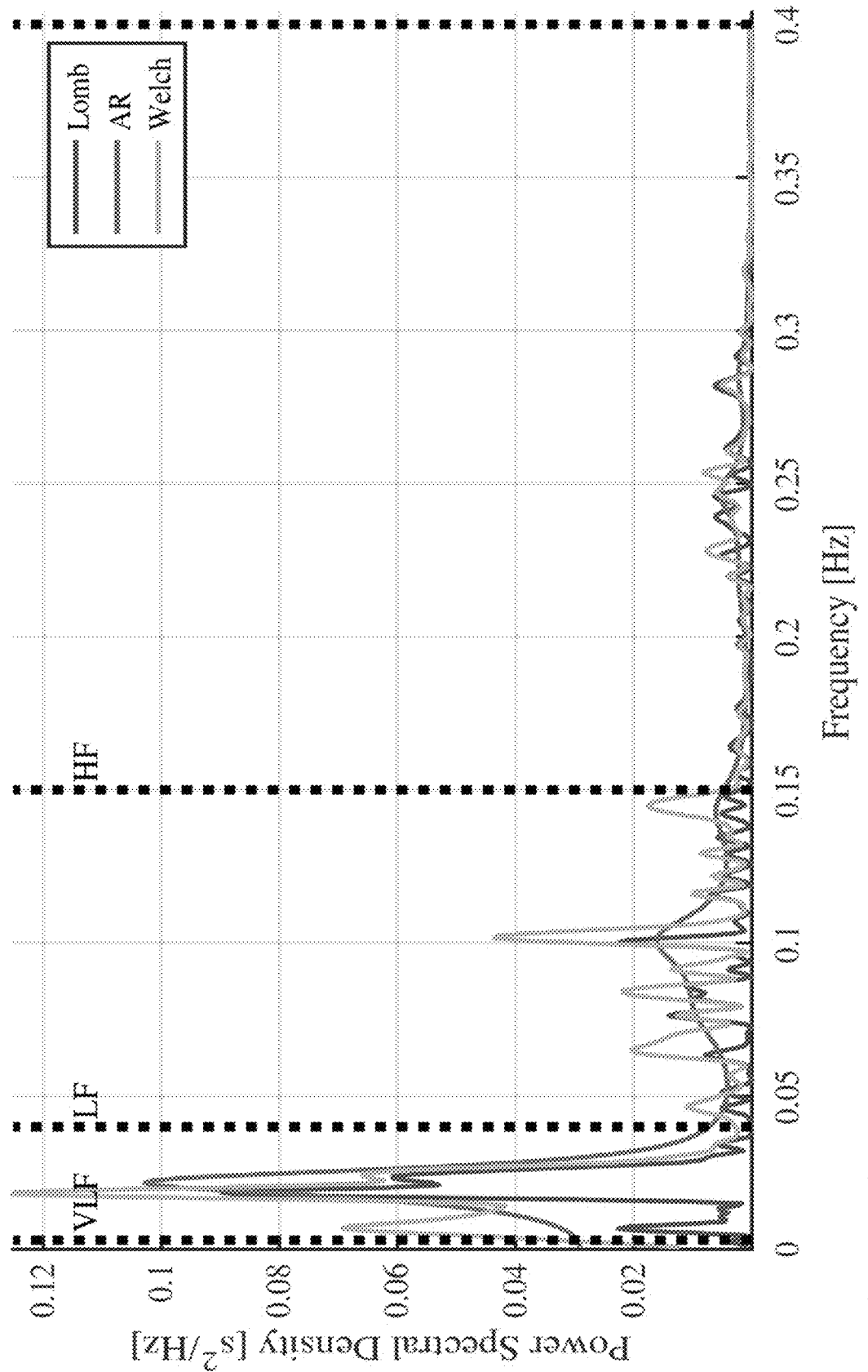
FIG. 13 shows methods for spectral estimation, applied to ECG data from PhysioNet, as well as the frequency ranges used to calculate the frequency domain metrics.

For this disclosure we used three methods of spectral estimation: Autoregressive modeling, Welch's periodogram and the Lomb-Scargle periodogram. For the AR and Welch methods, a cubic spline was fitted to the data and it was resampled at a frequency 2.25 times greater than the end of the HF band in order to comply with the Nyquist criterion. All spectral analysis of the canine data was performed on segments approximately 5-minutes long that were segmented to remove transients and improve stationarity (see the section "ECG Segmentation" above). An AR model of order 24 was fitted to the segment using the Yule-Walker method in order to obtain a parametric spectrum estimation. The Welch method was configured for 5-minute segments with 50% overlap (however in practice there is only one segment in each canine data record). FIG. 13 shows the aforementioned methods for spectral estimation, applied to ECG data from PhysioNet, as well as the frequency ranges used to calculate the frequency domain metrics. To verify correctness of implementation, the PhysioNet HRV toolkit was used to independently calculate the same metrics, and results were compared. In this figure, the expected spectral peaks at 0.1 and 0.25 Hz are visible in all three methods, however the AR method provides a smoother and therefore simpler estimate of the spectrum.

Adaptation for Canine Data

The frequency domain methods can be used as-is on canine data sets. However due to the significantly higher heart rate found in the canines, the frequency bands must be adapted. See the Frequency Domain Metrics section for the adaptation method we used. The following frequency bands were calculated for the canine data set: VLF 0.0048-0.064 Hz; LF 0.064-0.24 Hz; HF 0.24-0.64 Hz.

4.5 Fractal Methods

A major drawback of common time and frequency-domain methods is that they assume stationarity of the data (i.e. that its statistical properties don't change with time). However, this is rarely the case with cardiac RR intervals which are known to be comprised of seemingly erratic and chaotic fluctuations including (and especially) in the case of healthy individuals. As discussed in the Heart Rate and Heart Rate Variability section, the RR interval time series in healthy subjects exhibits self-similar characteristics. The term "self-similar" is usually used to describe fractal phenomena and indeed, the RR interval time series exhibits fractal characteristics which break down under conditions of disease and aging. This breakdown can manifest either with more order (signal becomes less chaotic, more predictable) or with less order (signal becomes more chaotic, behaves like uncorrelated noise).

FIG. 14 provides one such example. Top: RR interval time series of a healthy individual, characterized by non-stationary complexity, with multiple visually disparate segments.

Middle: A subject with severe congestive heart failure, exhibiting abnormally excessive regularity and periodicity. Bottom: A subject with atrial fibrillation, manifesting in highly irregular intervals resembling uncorrelated noise. These examples show how pathology, through breakdown of fractal dynamic of the heart rate, can manifest as an either more or less complex interval time series.

The two main properties of fractal objects is that they are composed of multiple sub units resembling the whole (self-similarity) and that they have a non-integer (fractional) dimension. Fractal objects are highly related to power-laws. A famous example of this was given by B. B. Mandelbrot regarding the measurement of the length of coastlines. Measuring a coastline is usually performed in multiples of unit 'ruler' length G: $L(G)=N \cdot G$ where G is selected to be small enough to that no meaningful features are shorter. Surprisingly, it was empirically discovered that the shorter the ruler length, the longer the coast and moreover a power-law relationship emerges when plotting the measured length of the coast L(G) as a function of the ruler-length: $L(G)=f \cdot G^{1-d}$, $d \geq 1$. When plotting this relationship on a double-log scale a linear trend exists, with a slope of $1-d$. The constant d is called the 'fractal dimension' of the object. The features of the coastlines, as many other shapes in the natural world, have an irregularity to them that is can be difficult to quantify. Mandelbrot showed that these objects can be measured and categorized in terms of their fractal dimension. An interesting and important property of power-laws is scale invariance. Consider the function $f(x)=a \cdot x^{-k}$. When scaling the argument by a constant c, the value of the function is also scaled proportionally to that constant: $f(cx)=a \cdot (cx)^{-k}=c^{-k} a \cdot x^{-k}=c^{-k} \cdot f(x)$. This means that power-laws of different scales are all equivalent up to constant factors. This scale-invariance is what gives fractal objects their self-similar characteristics.

In case of a time dependent process, self-similarity means that the process retains it's statistical properties when rescaling to different time scales: statistical scale-invariance. Mathematically, a process y(t) is said to be self-similar with scaling exponent $\alpha$ if it has a probability distribution identical to itself after rescaling by a factor of r on the x-axis and of $r^\alpha$ on the y-axis:

$$y(t) \equiv r^\alpha y\left(\frac{t}{r}\right), \qquad (26)$$

where ≡ denotes the probability distribution of both sides is identical. Note that contrary to the spatial case, here we need two different scaling factors because the x- and y-axes correspond to different physical variables. For example, if r>1 we can think of this scaling as zooming-in: the x-axis is magnified by r while the y-axis is magnified by $r^\alpha$.

The parameter $\alpha$ is one possible measure of the complexity of the time series, similar to the concept of the fractal dimension. The challenge is estimating it from a given time-series. One method for estimating $\alpha$ directly from time-series data is called Detrended Fluctuation Analysis (DFA). This method has been previously used on RR interval times series while showing great promise for classification of pathological data. In practice, when working with real-world signals, there is obviously an upper and lower bound to the scale factor r (since the signals are bounded) and our ability to estimate the statistical properties accurately is limited. To overcome the first problem, real-world data is first integrated to obtain an unbounded signal. To overcome the second, the integrated signal is then broken down into windows of n samples, and the statistical properties of the signal is estimated separately in each window using some metric, then averaged. Denote this metric as the average fluctuation, F(n). Given a signal y[k] of length N, the DFA algorithm defines F(n) as the RMS difference between each sample y[k], and the linear trend in that sample's box $y_n[k]$:

$$F(n)=\sqrt{\frac{1}{N}\sum_{k=0}^{N-1}(y[k]-y_n[k])^2}. \qquad (27)$$

Figure 15A:
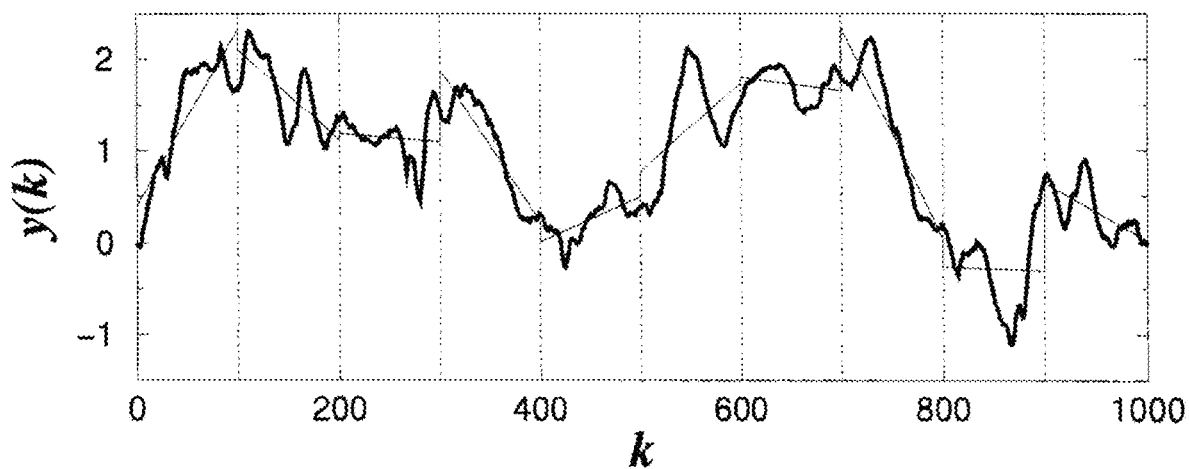
FIG. 15A shows a boxing process and the local trend that is subtracted in each box.
Figure 15B:
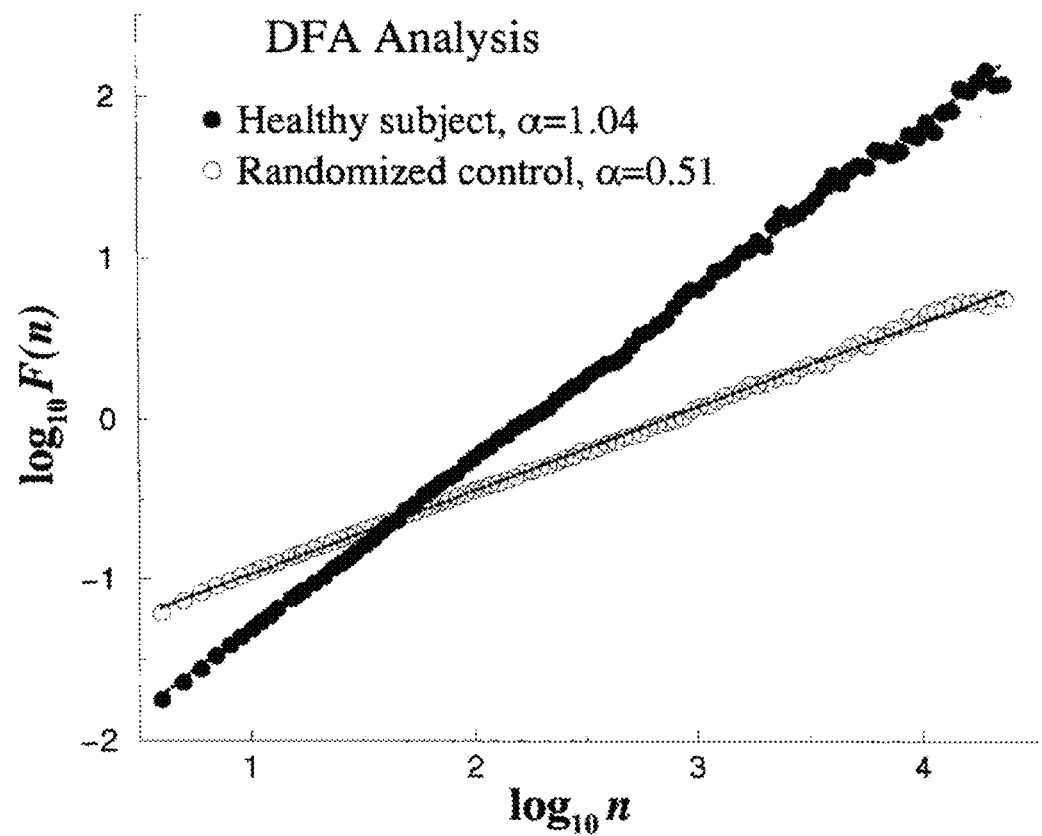
FIG. 15B is a log-log plot and linear regression for estimation of the self similarity parameter α.

FIG. 15A shows the boxing process and the local trend that is subtracted in each box. The figure shows an example signal y[k] broken into 10 boxes of length n=100. The piecewise-continuous line is the box-local linear trend, $y_n[k]$. The process of splitting the signal into boxes of length n and calculating F(n) is repeated for all possible values of n (1 to N). The outcome of this process is that the x-axis scale parameter r is mapped to the size of the windows that we look at the signal through, and the y-axis scale parameter $r^\alpha$ is mapped to the average fluctuation at that window size. Plotting F(n) as a function of n can therefore be thought of as plotting $r^\alpha$ vs. r—a power-law graph. The self similarity parameter, $\alpha$, is therefore estimated by linear regression of the slope on a log-log plot of F(n) vs. n[18]. This can be seen in FIG. 15B, which is a log-log plot and linear regression for estimation of $\alpha$.

Interestingly, the value of $\alpha$ estimated from a signal can be used to classify it's autocorrelation function and also it's power-spectrum. For a white-noise process, in which each sample is completely uncorrelated with any other, $\alpha$ will have a value of 0.5. Thus, processes with alpha very close to 0.5 behave as random uncorrelated noise—we can expect their autocorrelation function to be approximately zero for non-zero lags and their power-spectral density to be approximately flat. Signals with $0.5<\alpha \leq 1$ have an autocorrelation function which obeys a power-law behavior: $R(\tau) \propto \tau^{-\gamma}$. Since the power-spectrum is given by taking the Fourier-transform of the autocorrelation, the spectrum also exhibits power-law scaling and in fact $S(f) \propto f^{-\beta}$ where $\beta=2\alpha-1$. Two additional important cases are $\alpha=\beta 1$, corresponding to $1/f$ or pink noise, often a characteristic of physiological processes, and $\alpha=3/2, \beta=2$ which corresponds to brownian noise, the integral of white noise.

It has been found that the power spectrum of healthy heartbeat intervals obeys a power-law form with a $1/f$ type distribution ($\beta=1$). This type of power distribution was also previously known to be the most ubiquitous when it comes to physiological and natural data. A $1/f$ distribution can be thought of as a middle ground between the uncorrelated randomness of white noise ($\beta=0$) and the more regular, smoother, features of brownian noise ($\beta=2$). However, in when considering the complexity or information content in the signal, $1/f$ noise was previously shown to be the most complex. The $\beta$ scaling exponent can be estimated from the power-spectral density of a time series. Herein we estimated it based on a PSD derived from an AR model of order 24, by taking the slope of a line fitted with linear regression to the log-log PSD over the VLF frequency band. The DFA algorithm was implemented based on Chung-Kang Peng et al., Mosaic organization of DNA nucleotides, Physical Review, 1994, herein incorporated by reference in its entirety, and the PhysioNet implementation. Note that the major drawback of directly estimating $\beta$ is that spectral estimates assume stationarity of the input, while the DFA method requires no such assumption.

Adaptation for Canine Data

The fractal methods require no adaption. However, when using a PSD-based estimate of β, the appropriate VLF frequency band must be chosen for the canine data.

4.6 Entropy-Based Methods

The entropy of a stochastic signal, is a measure of the average amount of information it contains. For a discrete random variable X with a probability measure P(X) the entropy is defined as $$H(X) = \mathbb{E}[-\log(P(X))] = -\Sigma_{i=1}^{N} P(X=x_i) \log(P(X=x_i)) \quad (28)$$

where $x_i$, i=1, ..., N are the N discrete values that X can take. A stochastic process is a sequence of random variables $X_1, \ldots, X_n$ sampled at sequential points in time. In case of digital signals, $X_i$ are discrete and all take on the same set of possible values (e.g. 0-255). Generally the value of each sample depends on all previous samples, and therefore a joint probability $P(X_1, \ldots, X_n)$ is used. The entropy of a stochastic process with n time samples is therefore:

$$H_n = H(X_1, \ldots, X_n) = \mathbb{E}[-\log(P(X_1, \ldots, X_n))] \quad (29)$$

$$= -\Sigma_{i_1=1}^{N} \ldots \Sigma_{i_n=1}^{N} P(X_1 = x_{i_1}, \ldots, X_n = x_{i_n}) \log(P(X_1 = x_{i_1}, \ldots, X_n = x_{i_n})) \quad (30)$$

Entropy increases with the amount of irregularity in a signal; predictable signals (e.g. a periodic waveform) have very low entropy, while completely random signals such as white noise have high entropy. This stems directly from the definition, because events with a low probability will produce higher values of entropy. It can be shown that the maximal possible entropy occurs for a uniformly distributed random variable and, in the case of a stochastic process, for an uncorrelated random process taking on uniformly distributed values at each point in time.

As discussed in the Fractal Methods section above, pathology of the heart usually reduces the fractal dynamics present in the heart rate, therefore diminishing the complex long-range correlations found in the healthy heart rate. Because there is a relationship between a signal's complexity, influenced by pathology, and it's irregularity (measured by entropy), various methods based on the concept of entropy have been proposed for studying the complexity of biological signals. A prominent entropy-based complexity measure is Sample Entropy, which measures the irregularity of a signal by looking at probability that two similar sequences of length m in the signal are also similar for length m+1. More formally, given a time series u[n], n=1, ..., N, define a sequence of length-m vectors starting at each sample, $$u_m(i) = \{u[i], u[i+1], \ldots, u[i+m]\}, i=1, 2, \ldots, N-m \quad (31)$$

and denote $$n_i^m(r) = |\{d(u_m(i), u_m(j)) \leq r : i \neq j, 1 \leq i, j \leq N-m\}| \quad (32)$$

which is the number of vectors within distance r of $u_m(i)$ with respect to the distance measure $$d(u, v) = \max_i |u[i] - v[i]| \quad (33)$$

which is the $l_\infty$-norm. These vectors are template matches of length m. Note that i only goes up to N−m so that templates of length m+1 can also be defined at each start index i, and that the requirement i≠j for $n_i^m(r)$ prevents counting a template as a match for itself. The r parameter is usually chosen as a small percentage of the signal's standard deviation. The probability of a match existing for a template starting at index i can be estimated by $$p_i^m(r) = \frac{1}{N-m-1} n_i^m(r) \quad (34)$$

because there are N−m−1 total possible matches when excluding self matches (i≠j). The total probability that two sequences of length m in the signal will match is therefore $$p^m(r) = \frac{1}{N-m} \Sigma_{i=1}^{N-m} p_i^m(r) \quad (35)$$

since there are N−m template start points. Given the above definitions, the Sample Entropy of u[t] is defined as $$SampEn(m, r) = -\ln \frac{p^{m+1}(r)}{p^m(r)} \quad (36)$$

$$= -\ln \frac{\Sigma_{i=1}^{N-m} n_i^{m+1}(r)}{\Sigma_{i=1}^{N-m} n_i^m(r)}. \quad (37)$$

The Sample Entropy measure is therefore an estimate of the conditional probability that a sequence in the signal of length m+1 will match a template, given that the first m samples match. Note that as with any entropy measure, Sample Entropy is maximal for uncorrelated random noise, because in such a case m matching samples does not provide any information regarding the sample m+1. Inversely, for a highly predictable and correlated signal (e.g. slow oscillations) the Sample Entropy will be low.

Figure 16:
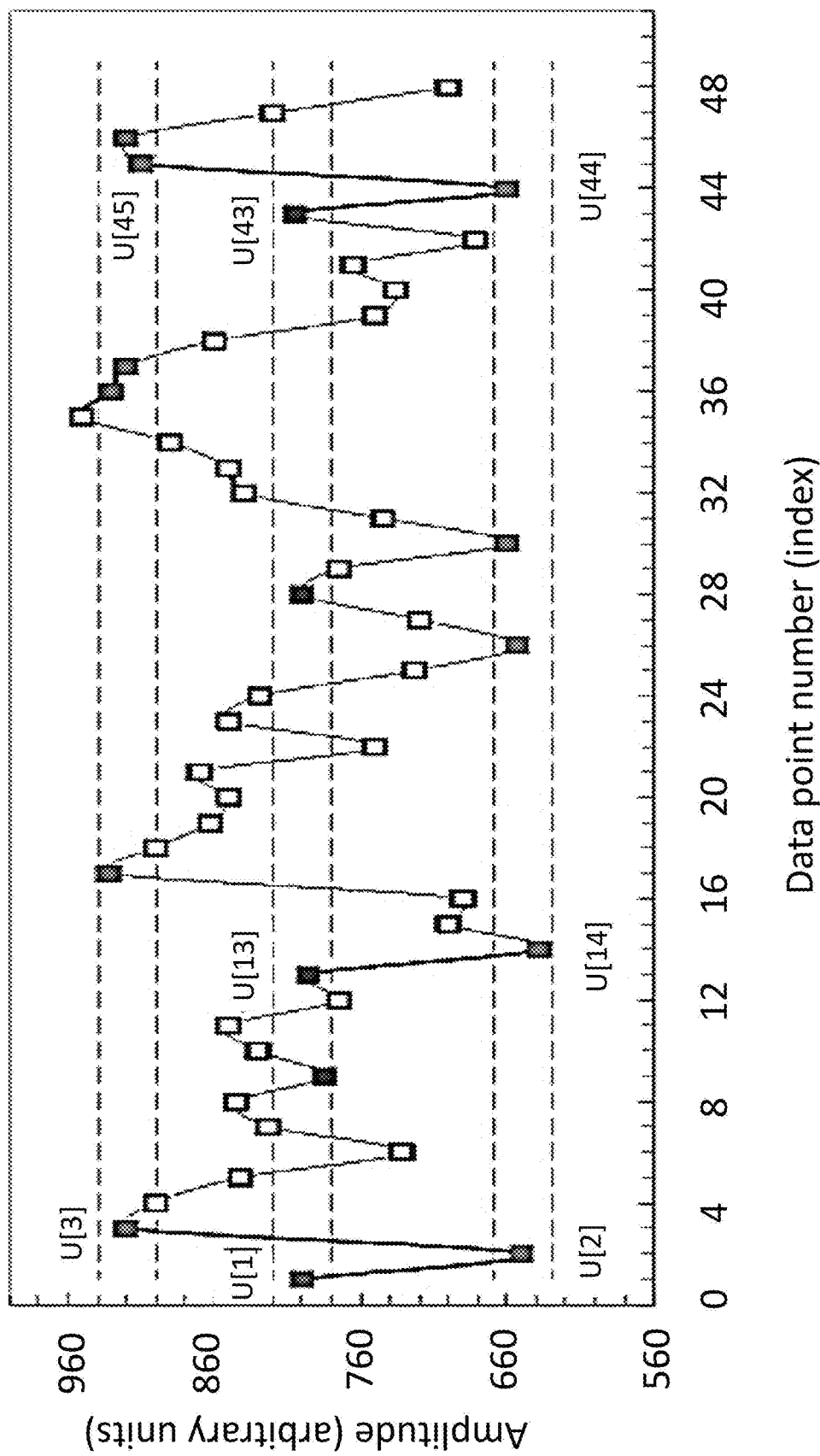
FIG. 16 shows an example of template matching performed by the Sample Entropy algorithm for m=2.

FIG. 16 shows an example of template matching performed by the Sample Entropy algorithm for m=2. The first m+1 samples are used as a template and the dashed lines represent an error interval of width r around each of the template samples. We can see that a partial match of length m exists at samples 13-14, and a complete match of length m+1 exists at samples 43-45. The matching process is performed for each possible template in the signal, and the total number of m-length and m+1-length matches are counted.

The main drawback of entropy-based methods is that they measure irregularity, not complexity. Complexity depends on the degree of information content in the signal. While complex signals can be highly irregular, irregular signals are not necessarily complex (e.g. uncorrelated noise). This presents a major limitation for using entropy methods as a complexity measure of physiological data because, as discussed previously (see, e.g., FIG. 14), pathology and aging states cause loss of fractal complexity which can manifest in either less-random or more-random interval time series. A possible reason for this limitation is that these measures analyze only the shortest time scale existing in the signal (two adjacent samples), while the complexity of physiological signal comes from their fractal dynamics, which produce long-range correlations on multiple time scales. To quantify complexity of physiological data, we ideally need a measure which will be low for both cases of complexity loss and take multiple time scales into account.

Multiscale Entropy (MSE) is a complexity measure based on Sample Entropy, which aims to overcome the limitations of Sample Entropy as a complexity measure for physiological data. To calculate the MSE of a signal x[n] of length N we first define a "coarse-grained" signal $x^\tau[n]$ where $\tau=1, \ldots, M$ represents a time scale, and $M \ll N$:

$$x^\tau[n] = \frac{1}{\tau} \sum_{i=(n-1)\tau+1}^{n\tau} x[i], \quad 1 \leq n \leq \frac{N}{\tau}. \tag{38}$$

This signal is simply the average of τ adjacent samples in non-overlapping windows of the original signal. After generating $x^\tau[n]$ for multiple scales, the Sample Entropy is calculated for each of them and plotted as a function of the scale τ, producing the MSE curve. This curve is examined to determine the complexity of a signal instead of generating just a single value as the complexity measure. Note that τ=1 gives us $x^\tau[n]=x[n]$ and therefore the MSE value at the first scale is equal to the Sample Entropy of x[n].

Figure 17A:
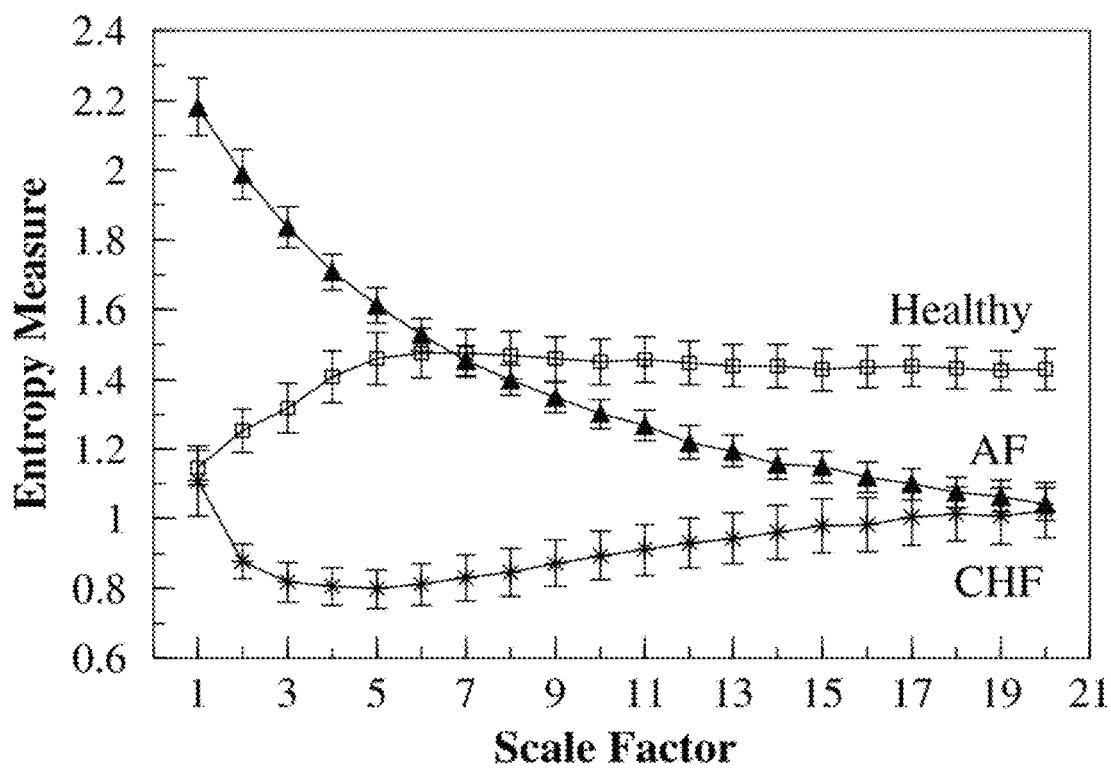
FIG. 17A shows MSE curves for white noise and 1/ƒ noise, showing both theoretical values and empirical values from computer generated signals.
Figure 17B:
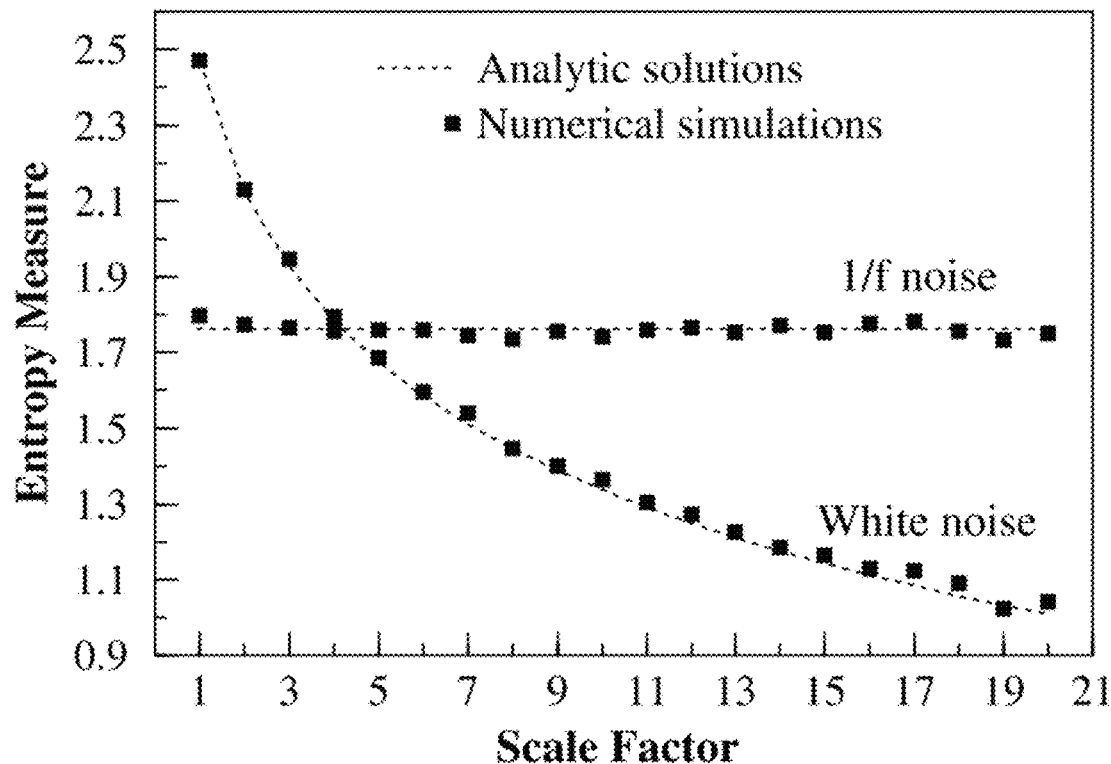
FIG. 17B shows MSE curves for different pathology states.

FIGS. 17A and 17B show multiscale entropy curves. A signal is considered more complex than another if it's entropy is higher for the majority of time scales. A monotonic decrease in entropy with scale indicates a signal only contains information on the smallest scale.

FIG. 17A shows MSE curves for white noise and 1/f noise, showing both theoretical values and empirical values from computer generated signals. These curves show that as expected the 1/f process has a greater complexity even though white noise is more irregular (has a much higher entropy value at scale 1).

FIG. 17B shows MSE curves for different pathology states. We can see how both atrial fibrillation and congestive heart failure states exhibit reduced complexity, even though AF causes a highly irregular heart rate while the effect of CHF is opposite. This can also be seen in FIG. 14.

Results
HRV Transition Before and After Autonomic Denervation

Figure 18A:
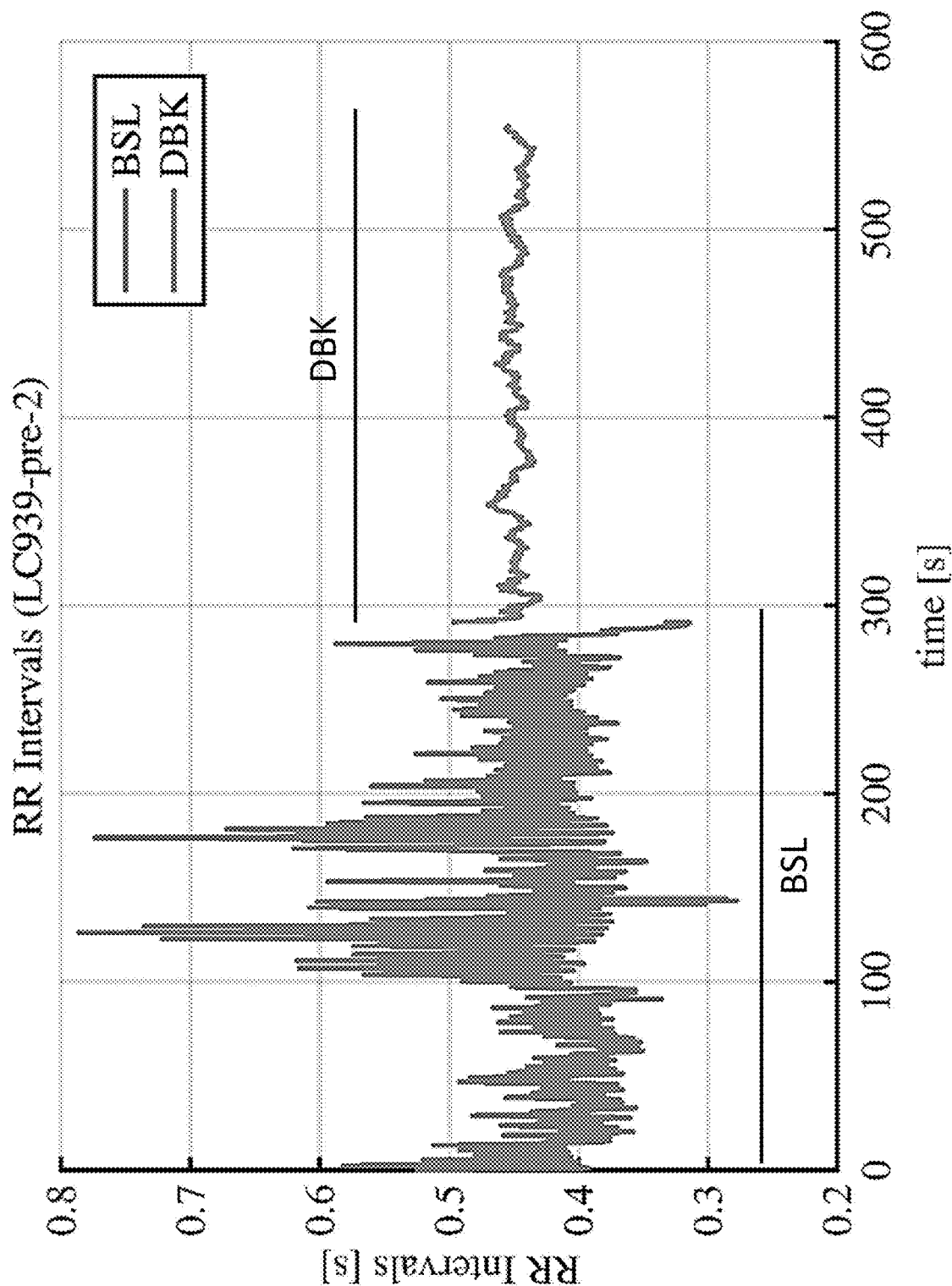
FIG. 18A illustrates representative examples of beating interval series in the canine before (BSL) and after (DBK) autonomic denervation.
Figure 18B:
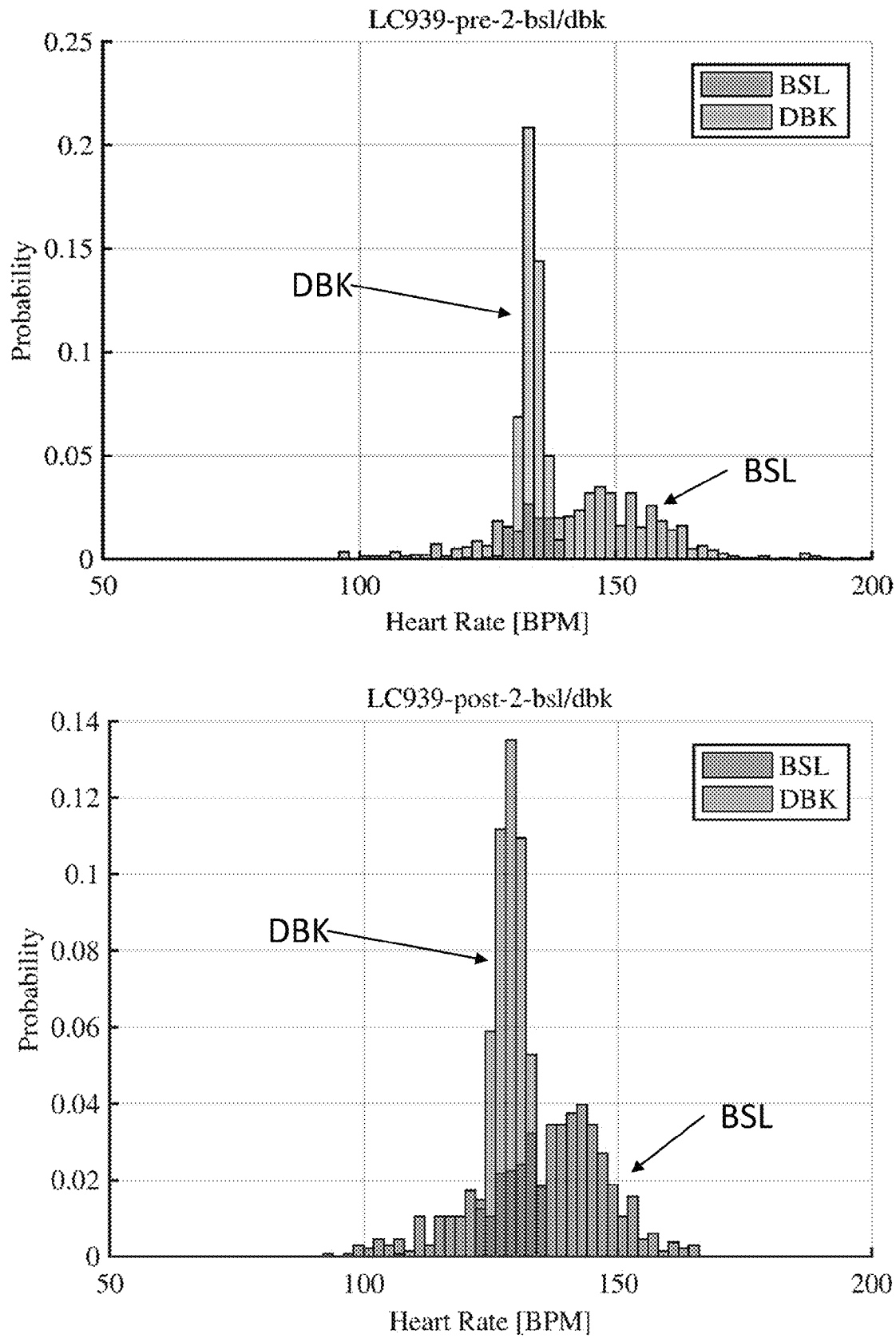
FIG. 18B illustrates representative examples of beating interval histograms before and after autonomic denervation of untrained dogs (top histogram) and trained doges (bottom histogram).
Figure 18C:
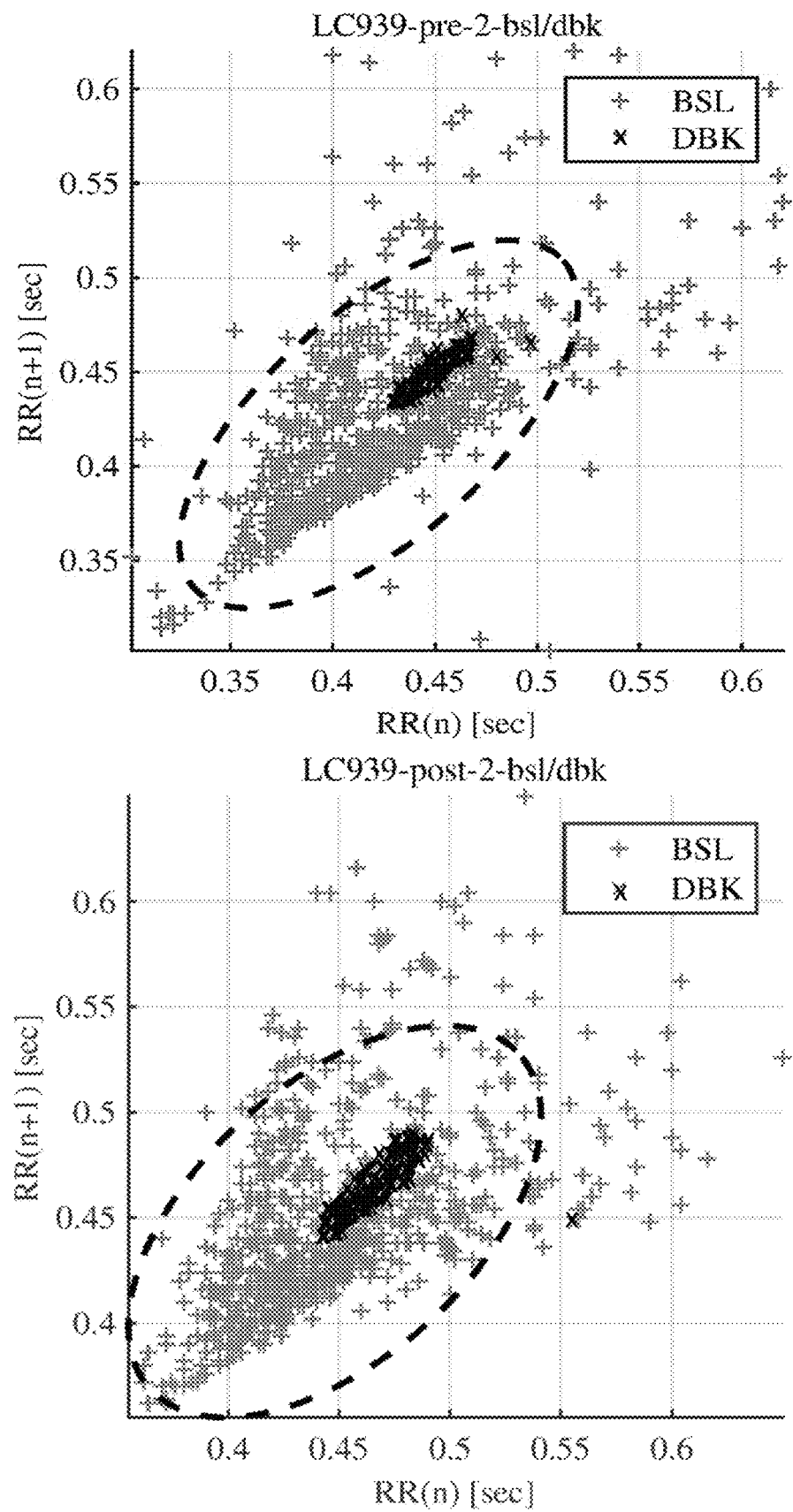
FIG. 18C shows Poincaré plots for before and after autonomic denervation, in which each beating cycle length is plotted against its predecessor to quantify the correlation between consecutive heart beating intervals of untrained (top graph) and trained (bottom graph) dogs.

FIG. 18A illustrates representative examples of beating interval series in the canine before (BSL) and after (DBK) autonomic denervation. The average beating interval increases from 541.6±20 to 628.2±17 ms after autonomic denervation. FIG. 18B illustrate representative examples of beating interval histograms before and after autonomic denervation, in non-exercised and exercised dogs (Top and bottom graphs, respectively). Note that the variability of beating intervals is reduced after autonomic denervation. The reduction in HRV after autonomic denervation can easily be appreciated in Poincaré plots, in which each beating cycle length is plotted against its predecessor to quantify the correlation between consecutive heart beating intervals (FIG. 18C). Denervation decreases the scattering pattern of the points in the Poincaré plot. On average SD1 and SD2 decreased from 53±7 and 89±7 to 5±1 and 29±3 before and after denervation, respectively.

For the exercised dogs, the average beating interval increases from 566.6±15 to 598±17 ms before and after autonomic denervation. Similar trends of HRV were found for the exercise and control dogs (FIG. 18B).

The Pacemaker and the Nervous System Contribute Differently to the Frequency Regimes.

We next examined if under denervation mode when only the pacemaker signals are dominant there is a shift in the frequency domain and if there are certain frequencies when only the pacemaker system or the nervous system is dominate. The representative example in FIG. 19A suggest that the denervation of the heart in vivo tends to decrease high frequency (HF)/total power (from 61±2 to 29±4, before and after denervation, respectively) and thus an increase in low frequency (LF) relative to HF (from 0.7±0.1 to 4.5±10.8, before and after denervation, respectively) was found. Moreover, there is an increase in the very low frequency (VLF)/total power under denervation mode. For the exercise dogs, similar trends were documented.

Figure 19B:
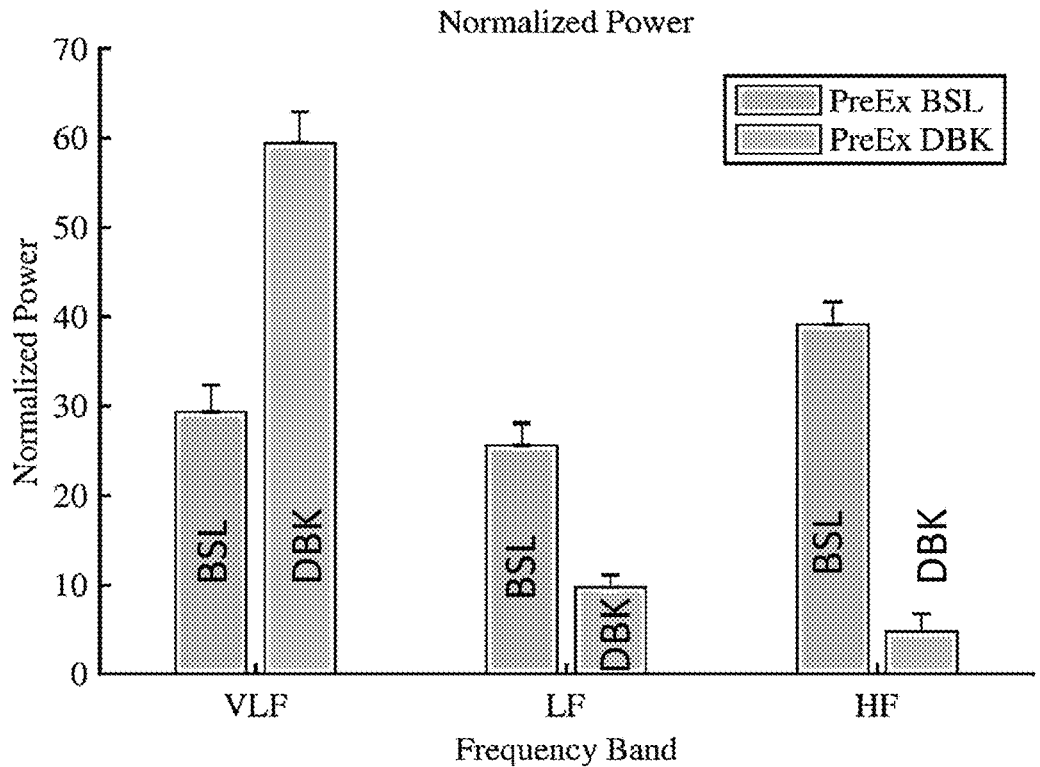
FIG. 19B shows normalized PSD as a function of frequency band, before and after autonomic denervation of trained dogs.

FIG. 19B shows a graph of normalized power in the very low frequency (VLF), low frequency (LF), and high frequency (HF) bands. The SAN contributes to VLF while the ANS contribute to LF and HF.

Figure 19C:
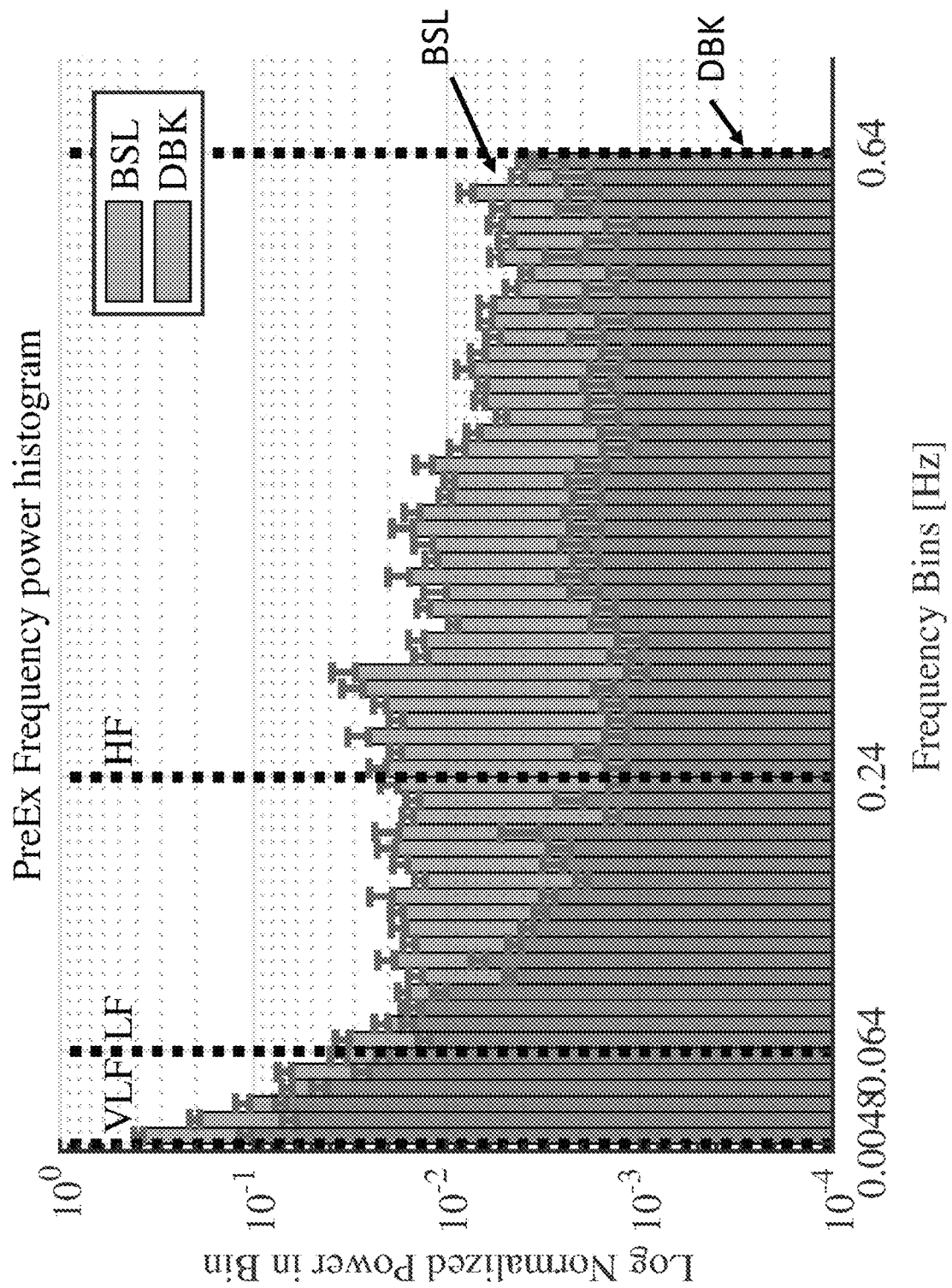
FIG. 19C shows log normalized power in a bin as a function of frequency bins, before and after autonomic denervation.

FIG. 19C shows a graph of normalized power in different bins over the spectrum. Note that the SAN contributes to VLF and specifically to the band between 0.003 to 0.1 Hz. The Pacemaker System Behaves as a Pseudo-Brownian noise.

Figure 20A:
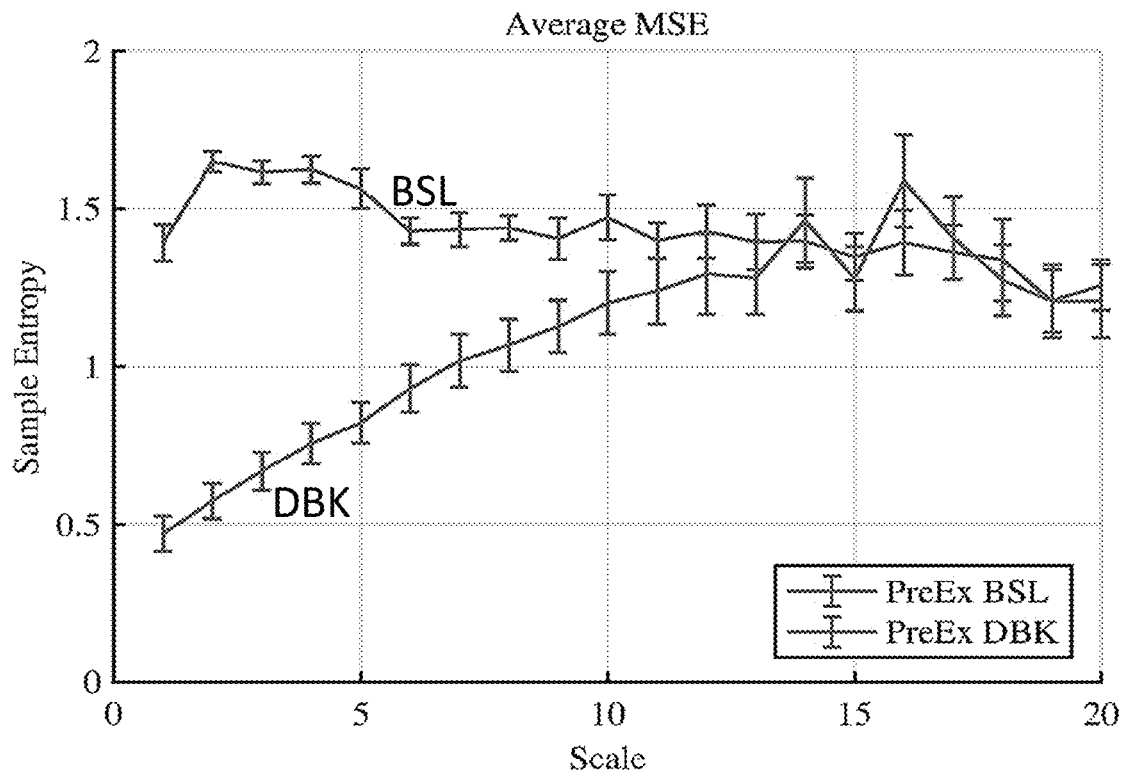
FIG. 20A shows that after autonomic denervation, the low scales entropy are lower.

Measurements of system entropy define the degree of order among beating intervals. Moreover, the trend in the system entropy can help to characterize the system behavior. FIG. 20A shows that after autonomic denervation, the first scale entropy (ApEn) is lower. Thus, the system order decreases after denervation, similar to the trends found here for the linear HRV analysis. FIG. 20A shows that under in vivo conditions the system behaves as "1/f noise" (e.g., pink noise). When only the pacemaker system affects the HRV the system behaves as a "1/f² noise" (e.g., Brownian noise).

Figure 20B:
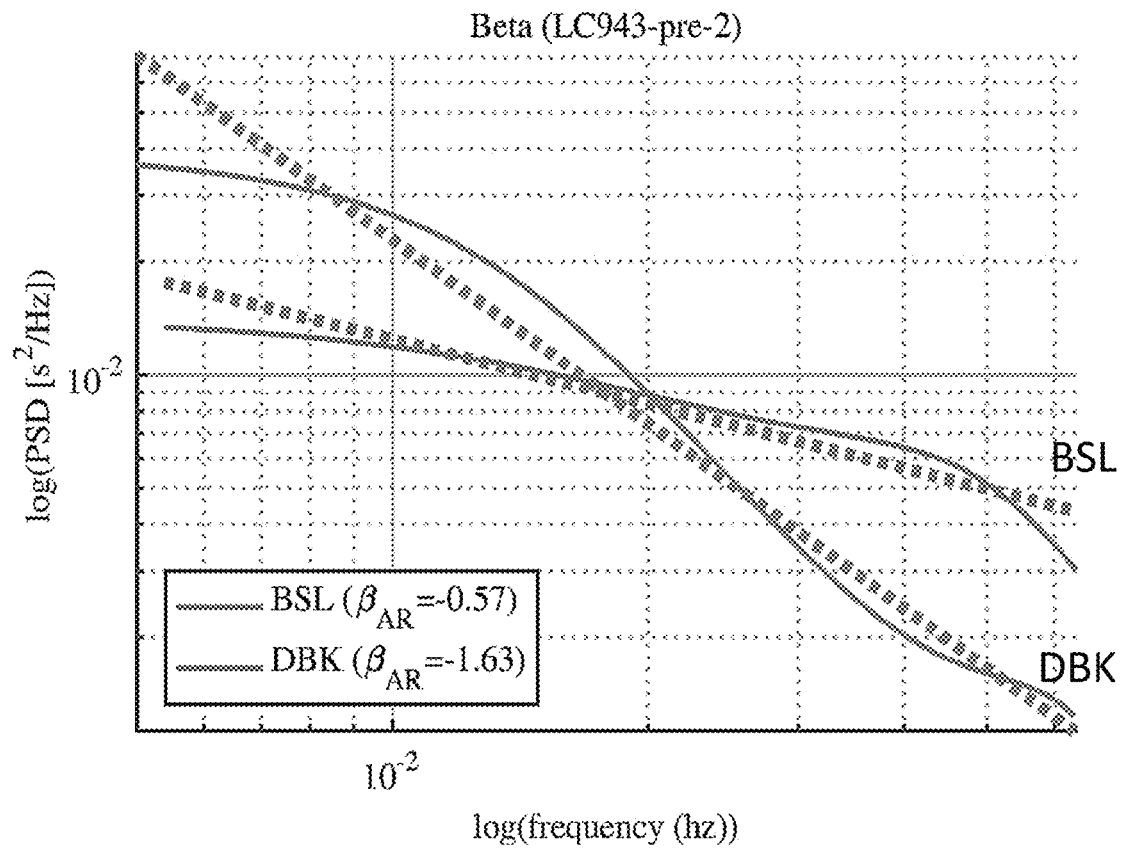
FIG. 20B shows that the slope of a linear function relating log frequency to log power spectrum density is the fractal scaling exponent β.
Figure 20C:
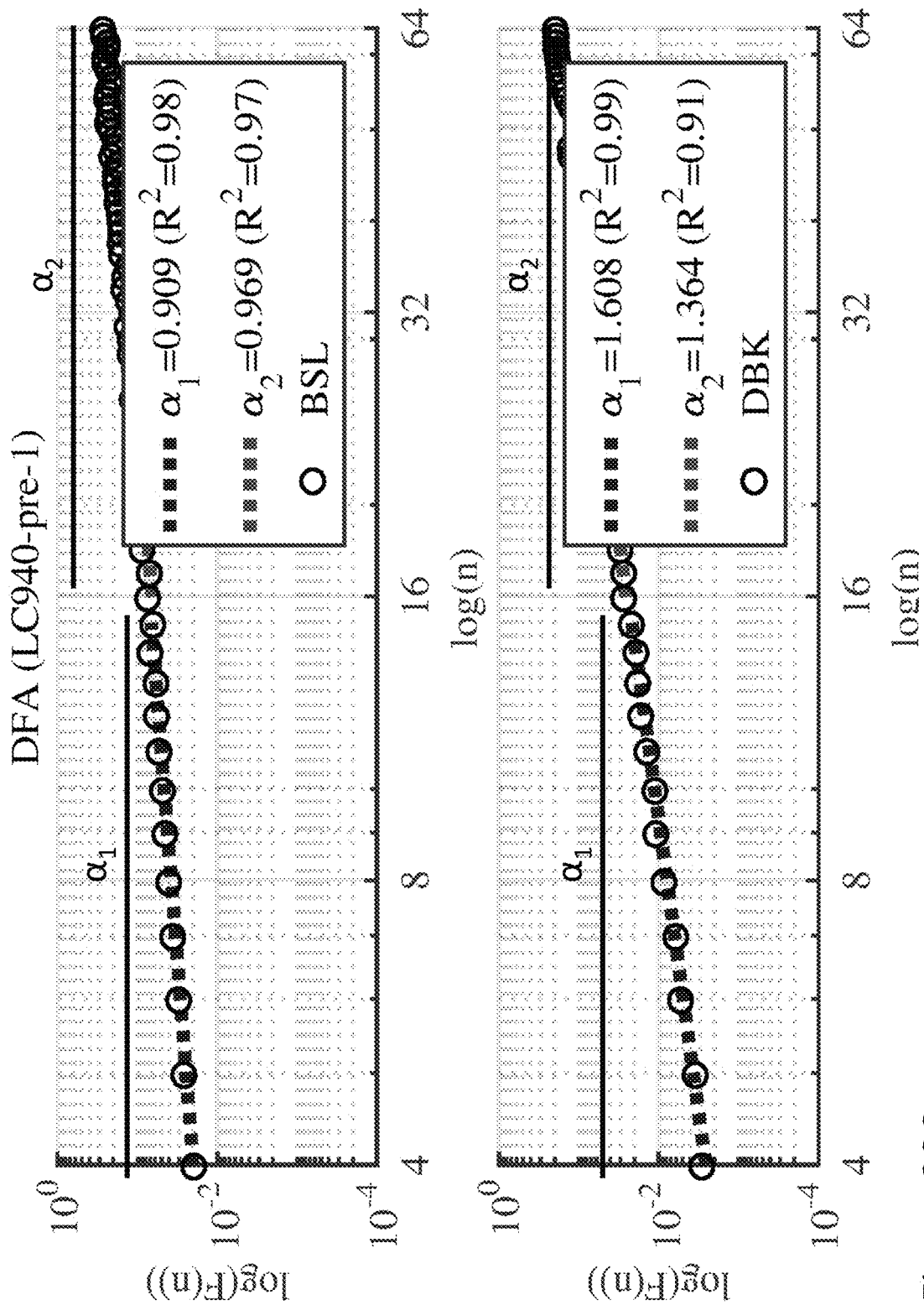
FIG. 20C shows that self-similarity exists under in vivo conditions and in the pacemaker level.

To confirm our conclusion that the pacemaker system behaves as pseudo-Brownian noise, we performed power-law analyses and detrended fluctuation analysis (DFA). The slope of a linear function relating log frequency to log power spectrum density is the fractal scaling exponent β (FIG. 20B). Fractal-like complexity among the heart beating intervals is present under in vivo conditions and in the pacemaker level (FIG. 20B). β increases after autonomic denervation from −0.8±0.1 to −1.2±0.1. DFA characterizes the degree of correlation among timescales embedded in the heart beating intervals. Self-similarity exists under in vivo conditions and in the pacemaker level (FIG. 20C). Both α1 and α2 increases after autonomic denervation. Both the power-law and DFA analyses show that under in vivo conditions the system behave as "1/f noise" and the pacemaker system behave as a "1/f²  noise". For the exercise dogs, similar trends were documented for all three methods.

Figure 21A:
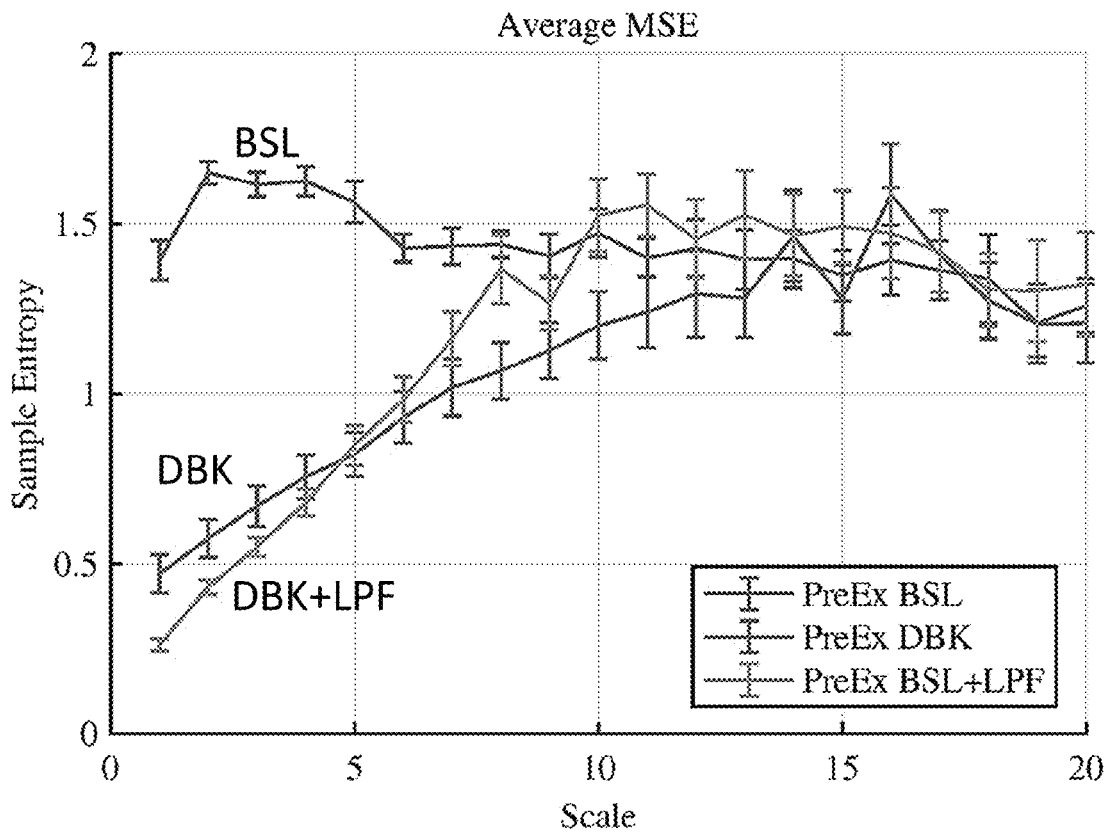
FIG. 21A shows that filtering the low pass frequencies from the in vivo data provided MSE behavior that is similar to the pacemaker system.
Figure 21B:
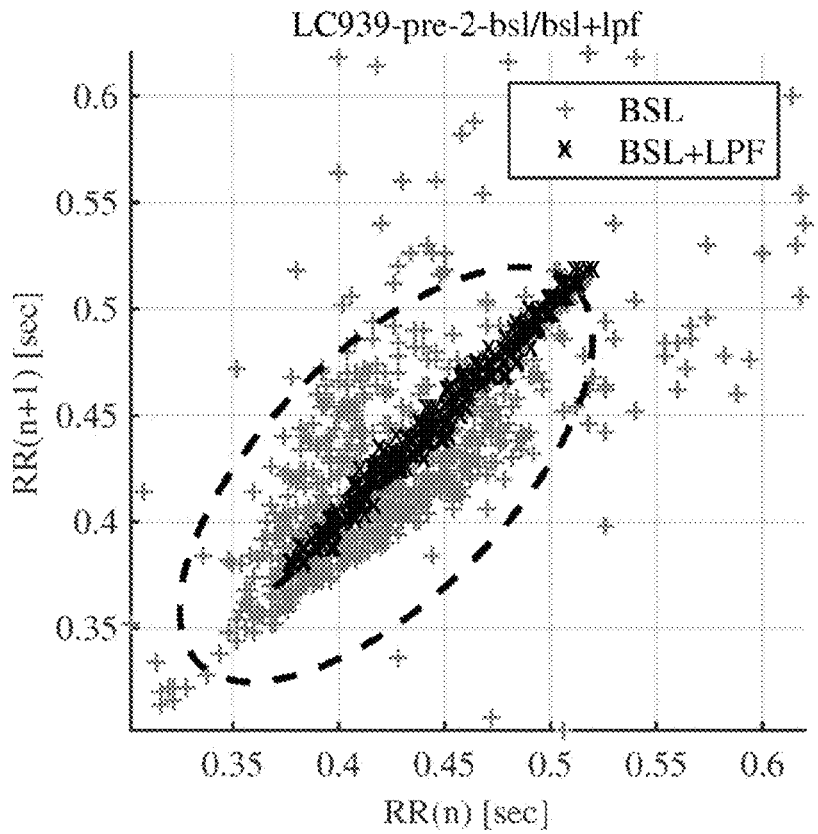
FIG. 21B shows that filtering the low frequencies decreases the scattering of the Poincaré plot reaching a behavior similar to pacemaker system.

Finally, to further provide evidence that the pacemaker system behaves as "1/f² noise" and thus contributes at lower frequencies we filtered the in vivo data with low pass filter. FIG. 21A shows that filtering the low pass frequencies from the in vivo data provided MSE behavior that is similar to the pacemaker system. FIG. 21B shows that filtering the low frequencies decreases the scattering of the Poincaré plot reaching a behavior similar to pacemaker system.

The Autonomic Nervous s System Behaves as a Pseudo White Noise.

Figure 22A:
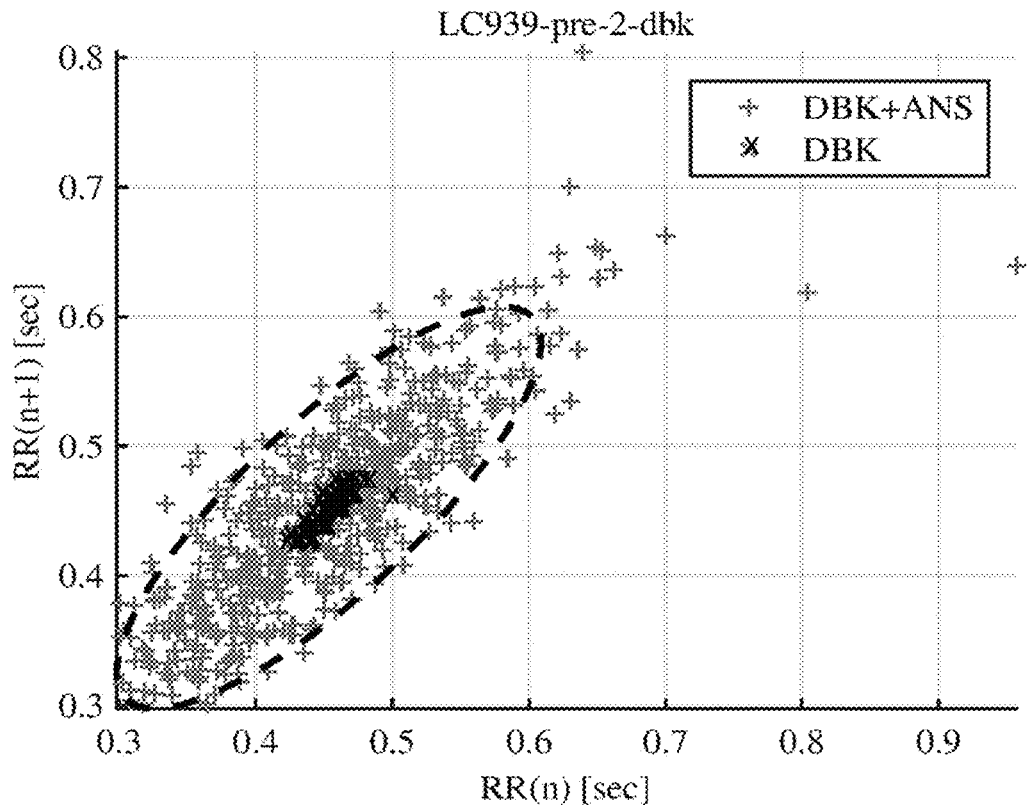
FIG. 22A shows that adding a white noise to the autonomic denervation signal provided MSE pattern that is similar to the in vivo data before denervation.
Figure 22B:
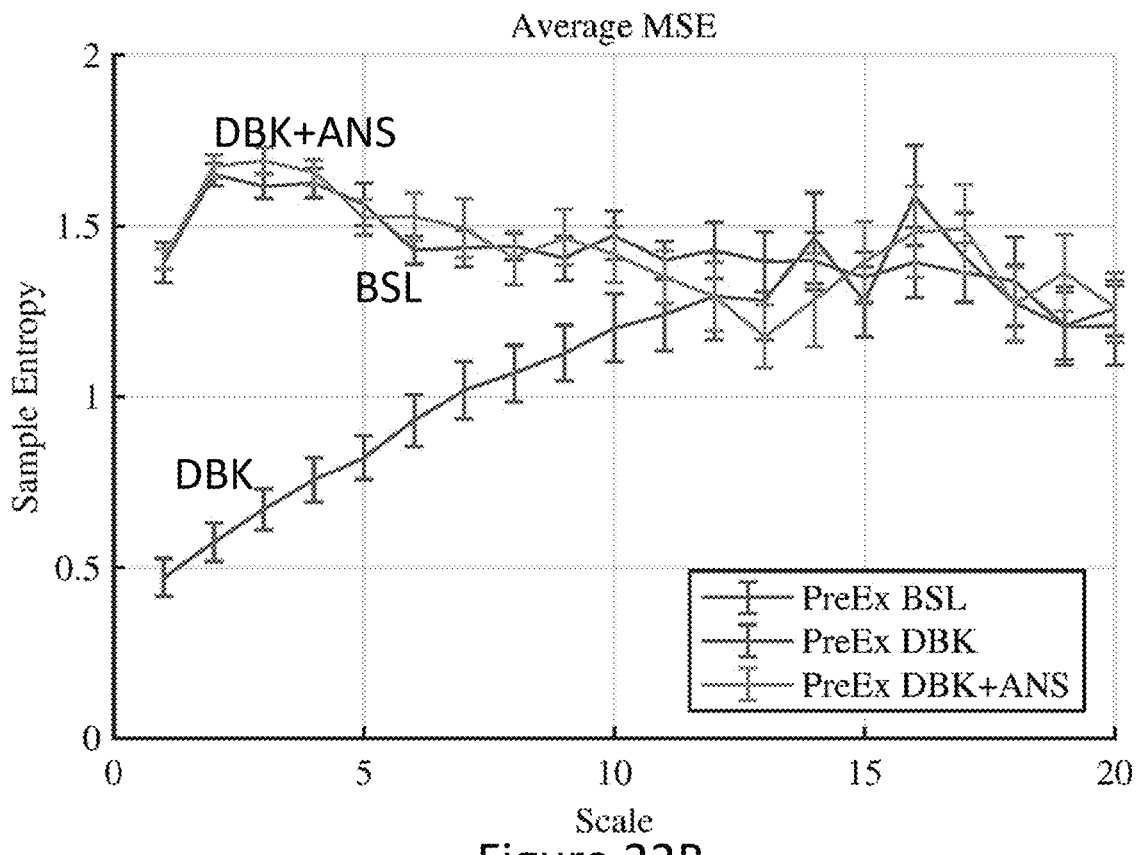
FIG. 22B shows that adding white noise to autonomic denervation signal restore the Poincaré plot to the one of in vivo.

Because the in vivo system behaves as "1/f noise" and includes influence of both the pacemaker system and the nervous system and because the pacemaker system behaves as "1/f² noise", one can assume from the MSE pattern that the nervous system contribution to the in vivo level behaves as a pseudo white noise. To prove this concept, we added white noise to the autonomic denervation signal. FIG. 22A shows that adding a white noise to the autonomic denervation signal provided an MSE pattern that is similar to the in vivo data before denervation. FIG. 22B shows that adding white noise to autonomic denervation signal restores the Poincaré plot to an enervated in vivo one.

What is claimed is:

1. A method for diagnosing heart function, the method comprising:
   receiving a digitized cardiac signal from said heart;
   computing a power spectral density (PSD) or computing multiscale entropy (MSE) of said digitized cardiac signal;
   evaluating at least one of:
   a) sinoatrial node (SAN) function of said heart based on said PSD within a frequency range of 0.003 to 0.1 Hertz (Hz), wherein a PSD within said frequency range of 0.003 to 0.1 Hz below a predetermined threshold indicates impaired SAN function;
   b) SAN function of said heart based on said MSE within a scale range of 10 to 20, wherein an MSE within said scale range of 10 to 20 below a predetermined threshold indicates impaired SAN function;
   c) autonomic nervous system (ANS) input to said heart based on said PSD within a frequency above 0.1 Hz, wherein a PSD within said frequency range of above 0.1 Hz below a predetermined threshold indicates impaired ANS input to said heart; and
   d) ANS input to said heart based on said MSE within a scale range of 1 to 10, wherein an MSE within said scale range of 1 to 10 below a predetermined threshold indicates impaired ANS input to said heart;
   thereby evaluating heart function;
   diagnosing the heart based on the evaluated heart function; and
   outputting diagnosis selected from: healthy heart function, impaired SAN function, impaired ANS input to the heart, and impaired SAN function and impaired ANS input to the heart, wherein presenting the diagnosis is on a computing device.

2. The method according to claim 1, wherein said digitized cardiac signal comprises temporal data of more than one heart beat.

3. The method according to claim 1, wherein the digitized cardiac signal is an electrocardiogram (ECG) signal.

4. The method according to claim 1, wherein said heart is from a subject at risk of developing, or suffering from, heart disease.

5. The method according to claim 4, further comprising at least one of:
   administering to said subject a SAN medication when said evaluating indicates impaired SAN function, and
   administering to said subject an ANS medication when said evaluating indicates impaired ANS function.

6. The method according to claim 5, wherein said SAN medication is selected from a phosphodiesterase inhibitor, and a calcium blocker.

7. The method according to claim 6, wherein said phosphodiesterase inhibitor is selected from 3-isobutyl-1-methylxanthine (IBMX) and sildenafil.

8. The method according to claim 5, wherein said ANS medication is a beta blocker.

9. The method according to claim 1, wherein said frequency above 0.1 Hz is 0.1 to 0.4 Hz.

10. The method according to claim 1, wherein said computing a PSD or an MSE comprises calculating heart rate variability (HRV) in said digitized cardiac signal.

11. The method according to claim 10, wherein said calculating HRV comprises filtering out ectopic heart beats.

12. The method according to claim 1, wherein said heart function is SAN function, and said method comprises evaluating (a), (b) or both.

13. The method according to claim 1, wherein said heart function is ANS input to said heart, and said method comprises evaluating (c), (d) or both.

14. A system configured to:
    acquire a digitized cardiac signal;
    compute a power spectral density (PSD) or multiscale entropy (MSE) of the digitized cardiac signal;
    evaluate at least one of:
    a) sinoatrial node (SAN) function of said heart based on said PSD within a frequency range of 0.003 to 0.1 Hertz (Hz), wherein a PSD within said frequency range of 0.003 to 0.1 Hz below a predetermined threshold indicates impaired SAN function;
    b) SAN function of said heart based on said MSE within a scale range of 10 to 20, wherein an MSE within said scale range of 10 to 20 below a predetermined threshold indicates impaired SAN function;
    c) autonomic nervous system (ANS) input to said heart based on said PSD within a frequency above 0.1 Hz, wherein a PSD within said frequency range of above 0.1 Hz below a predetermined threshold indicates impaired ANS input to said heart; and
    d) ANS input to said heart based on said MSE within a scale range of 1 to 10, wherein an MSE within said scale range of 1 to 10 below a predetermined threshold indicates impaired ANS input to said heart;
    diagnose the heart based on the evaluated heart function;
    output diagnosis selected from: healthy heart function, impaired SAN function, impaired ANS input to the heart, and impaired SAN function and impaired ANS input to the heart.

15. The system according to claim 14, comprising an electrocardiograph or heart rate monitor configured to acquire a digitized cardiac signal.

16. The system according to claim 14, wherein said digitized cardiac signal comprises temporal beat-to-beat heart data.

17. The system according to claim 14, wherein said computing a PSD or an MSE comprises calculating heart rate variability (HRV) in said digitized cardiac signal.

18. The system according to claim 17, wherein said calculating HRV comprises filtering out ectopic heart beats.

19. A computer program product for diagnosing heart function, the computer program product comprising a non-transitory computer-readable storage medium having program code embodied therewith, the program code executable by at least one hardware processor to receive a digitized cardiac signal from said heart;
    compute a power spectral density (PSD) or multiscale entropy (MSE) of said digitized cardiac signal;
    evaluate at least one of:
    a) sinoatrial node (SAN) function of said heart based on said PSD within a frequency range of 0.003 to 0.1 Hertz (Hz), wherein a PSD within said frequency range of 0.003 to 0.1 Hz below a predetermined threshold indicates impaired SAN function;
    b) SAN function of said heart based on said MSE within a scale range of 10 to 20, wherein an MSE within said scale range of 10 to 20 below a predetermined threshold indicates impaired SAN function;
    c) autonomic nervous system (ANS) input to said heart based on said PSD within a frequency above 0.1 Hz, wherein a PSD within said frequency range of above 0.1 Hz below a predetermined threshold indicates impaired ANS input to said heart; and
    d) ANS input to said heart based on said MSE within a scale range of 1 to 10, wherein an MSE within said scale range of 1 to 10 below a predetermined threshold indicates impaired ANS input to said heart;
diagnose the heart based on the evaluated heart function; and
output diagnosis selected from: healthy heart function, impaired SAN function, impaired ANS input to the heart, and impaired SAN function and impaired ANS input to the heart.

* * * * *